United States Patent
Ding et al.

(10) Patent No.: US 9,221,798 B2
(45) Date of Patent: Dec. 29, 2015

(54) 4-SUBSTITUTED-(3-SUBSTITUTED-1H-PYRAZOLE-5-AMINO)-PYRIMIDINE DERIVATIVES HAVING ACTIVITY OF INHIBITING PROTEIN KINASE AND USE THEREOF

(75) Inventors: Yili Ding, Shanghai (CN); Xuan Yang, Shanghai (CN); Qingyan Yan, Shanghai (CN); Hua Bai, Zhejiang (CN); Lifeng Cai, Shanghai (CN); Kenneth Smith, Shanghai (CN); Jian Chai, Zhejiang (CN)

(73) Assignee: Zhejian Hisun Pharmaceutical Co., Ltd., Zhejiang (CN)

( * ) Notice: Subject to any disclaimer, the term of this patent is extended or adjusted under 35 U.S.C. 154(b) by 0 days.

(21) Appl. No.: 14/342,656

(22) PCT Filed: Sep. 5, 2011

(86) PCT No.: PCT/CN2011/001499
§ 371 (c)(1),
(2), (4) Date: May 16, 2014

(87) PCT Pub. No.: WO2013/033862
PCT Pub. Date: Mar. 14, 2013

(65) Prior Publication Data
US 2014/0378488 A1  Dec. 25, 2014

(51) Int. Cl.
*C07D 401/14* (2006.01)
*C07D 403/12* (2006.01)
*A61K 31/4155* (2006.01)
*C07D 403/14* (2006.01)
*C07D 405/14* (2006.01)
*C07D 409/14* (2006.01)

(52) U.S. Cl.
CPC .......... *C07D 403/12* (2013.01); *A61K 31/4155* (2013.01); *C07D 401/14* (2013.01); *C07D 403/14* (2013.01); *C07D 405/14* (2013.01); *C07D 409/14* (2013.01)

(58) Field of Classification Search
CPC .. C07D 231/38; C07D 401/14; C07D 403/12; A61K 31/4155
USPC .......................................... 544/324; 514/275
See application file for complete search history.

(56) References Cited

U.S. PATENT DOCUMENTS

| 2008/0004302 | A1* | 1/2008 | Theoclitou et al. ........... 514/275 |
| 2008/0269266 | A1* | 10/2008 | Nowak et al. ................ 514/273 |
| 2009/0215759 | A1* | 8/2009 | Baumann et al. .......... 514/227.8 |

FOREIGN PATENT DOCUMENTS

| CN | 101346371 A | 1/2009 |
| CN | 101501030 A | 8/2009 |
| CN | 101857589 A | * 10/2010 |
| WO | WO 2009/056886 | * 5/2009 |

OTHER PUBLICATIONS

Ji et al., English Translation of CN 101857589 A (Oct. 13, 2010).*
Rivkin et al., CAPLUS Abstract 152:396992 (2010).*
Rivkin et al., Piperazinyl pyrimidine derivatives as potent gamma-secretase modulators, Bioorganic & Medicinal Chemistry Letters, 20(3), pp. 1269-1271 (2010).*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-101 O, 1995.*
International Search Report and Written Opinion of PCT Application No. PCT/CN2011/001499, dated Jun. 14, 2012.

* cited by examiner

*Primary Examiner* — Deepak Rao

(57) ABSTRACT

Provided are derivatives substituted by urea associated with 4-substituted-(3-substituted-1H-pyrazole-5-amino)-pyrimidine-2-amino of formula (I), wherein these compounds may selectively regulate or inhibit an information transmission process controlled by natural or variant tyrosine kinase. Also provided are preparation methods and uses of the compounds.

28 Claims, No Drawings

4-SUBSTITUTED-(3-SUBSTITUTED-1H-PYRAZOLE-5-AMINO)-PYRIMIDINE DERIVATIVES HAVING ACTIVITY OF INHIBITING PROTEIN KINASE AND USE THEREOF

CROSS REFERENCE TO RELATED APPLICATIONS

This application claims priority to International Publication Number WO 2013/033862, filed on Sep. 5, 2011, the disclosure of which is hereby expressly incorporated by reference in its entirety.

FIELD OF THE INVENTION

The invention relates to derivatives substituted by urea associated with 4-substituted-(3-substituted-1H-pyrazole-5-amino)-pyrimidine-2-amino, wherein these compounds can selectively regulate or inhibit an information transmission process controlled by natural or mutant tyrosine kinase. These transmission processes are associated with certain human and animal disease states, such as cell proliferation, metabolism, degeneration and anaphylaxis.

BACKGROUND OF THE INVENTION

Protein kinases represent a major class of proteins, which play an important role in the growth and function of cells. These protein kinases include receptor kinases, such as PDGF-R, trkB, FGFR3, B-RAF, KDR; non-receptor kinases, such as Abl, BCR-Ablm Lck, Bmx and c-src; serine kinases and threonine kinases, such as c-RAF, sgk, MAP kinase (for example, MKK4, MKK6, etc.), SAPK2α and SAPK2β. Abnormal behaviors of kinases are observed in many diseases caused by abnormal proliferation of benign and malignant cells, as well as many diseases caused by abnormal activation of immune system and nervous system. The compounds of the present invention can inhibit the activities of one or more protein kinases, thereby they can treat many disease states associated with the protein kinases.

SUMMARY OF THE INVENTION

The present invention provides a compound represented as the following general formula I, or a pharmaceutical acceptable salt thereof, a hydrate thereof, a solvate thereof:

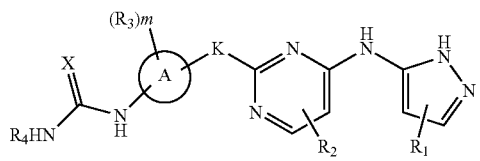

I wherein:
K is NH, O, S, SO, $SO_2$, $CH_2$, C=O or absent, preferably select from NH, O, S, $CH_2$ or absent, and preferably NH or absent; A is aryl, heterocycloalkyl, cycloalkyl or heteroaryl, preferably aryl or heteroaryl, further preferably phenyl, naphthyl or pyrazolyl, and most preferably phenyl;
m is an integer of 0 to 4;
X is O, S;
$R_1$ is hydrogen, halogen, —CN, —NO, —$NO_2$, —$NR_9R_{10}$, —$OR_{11}$, —$CO_2R_{12}$, —$SR_{13}$, —$COR_{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
$R_1$ may be selected from alkyl unsubstituted or substituted by $R_{32}$, heteroalkyl unsubstituted or substituted by $R_{32}$, cycloalkyl unsubstituted or substituted by $R_{32}$, heterocycloalkyl unsubstituted or substituted by $R_{32}$, aryl unsubstituted or substituted by $R_{32}$, heteroaryl unsubstituted or substituted by $R_{32}$;
Preferably, $R_1$ is C1-C10 alkyl unsubstituted or substituted by $R_{32}$, 2-10 membered heteroalkyl unsubstituted or substituted by $R_{32}$, C3-C8 cycloalkyl unsubstituted or substituted by $R_{32}$, 3-8 membered heterocycloalkyl unsubstituted or substituted by $R_{32}$; further preferably, $R_1$ is C1-C5 alkyl unsubstituted or substituted by $R_{32}$, 2-5 membered heteroalkyl unsubstituted or substituted by $R_{32}$, C3-C6 cycloalkyl unsubstituted or substituted by $R_{32}$, 5- or 6-membered heterocycloalkyl unsubstituted or substituted by $R_{32}$; further preferably, $R_1$ is unsubstituted C1-C5 alkyl, unsubstituted C3-C6 cycloalkyl, 5- or 6-membered heterocycloalkyl unsubstituted or substituted by $R_{32}$, such as unsubstituted C1-C5 alkyl, unsubstituted thienyl, C1-C4 substituted thienyl;
Lastly, preferably, $R_1$ is unsubstituted C1-C5 alkyl, further preferably methyl;
$R_{32}$ is halogen, —CN, —$CF_3$, —OH, —$NH_2$, —$SO_2$, —$CO_2H$, alkyl unsubstituted or substituted by $R_{33}$, heteroalkyl unsubstituted or substituted by $R_{33}$, cycloalkyl unsubstituted or substituted by $R_{33}$, heterocycloalkyl unsubstituted or substituted by $R_{33}$, aryl unsubstituted or substituted by $R_{33}$, heteroaryl unsubstituted or substituted by $R_{33}$;
$R_9$, $R_{10}$, $R_{11}$, $R_{12}$, $R_{13}$ and $R_{14}$ are independently of each other selected from hydrogen, alkyl unsubstituted or substituted by $R_{34}$, heteroalkyl unsubstituted or substituted by $R_{34}$, cycloalkyl unsubstituted or substituted by $R_{34}$, heterocycloalkyl unsubstituted or substituted by $R_{34}$, aryl unsubstituted or substituted by $R_{34}$, heteroaryl unsubstituted or substituted by $R_{34}$;
each $R_{34}$ is independently selected from halogen, —CN, —$CF_3$, —OH, —$NH_2$, —$SO_2$, —$CO_2H$, alkyl unsubstituted or substituted by $R_{35}$, heteroalkyl unsubstituted or substituted by $R_{35}$, cycloalkyl unsubstituted or substituted by $R_{35}$, heterocycloalkyl unsubstituted or substituted by $R_{35}$, aryl unsubstituted or substituted by $R_{35}$, heteroaryl unsubstituted or substituted by $R_{35}$;
$R_{33}$ and $R_{35}$ are independently of each other selected from halogen, —CN, —$CF_3$, —OH, —$NH_2$, —$SO_2$, —$CO_2H$, unsubstituted alkyl, unsubstituted heteroalkyl, unsubstituted cycloalkyl, unsubstituted heterocycloalkyl, unsubstituted aryl, or unsubstituted heteroaryl;
$R_2$ is amino, alkylamino, arylamino, heteroarylamino, thioalkyl, sulfoxide, sulfone, sulfamoyl, mercapto, halogen, alkoxy, alkanoyl, alkoxycarbonyl, C1-C6 alkyl, C2-C6 alkenyl, cycloalkyl, C2-C6 alkynyl, C5-C7 cycloalkenyl, aryl, heterocyclic aryl, heteroaryl, C1-C6 trifluoroalkyl, cyano, wherein each of the substituents is independently of each other substituted by any of 0 to 3 groups selected from halogen, amino, hydroxy, mercapto, nitro or cyano; preferably, $R_2$ is amino, alkylamino, arylamino, heteroarylamino, mercapto, halogen, alkoxy, C1-C6 alkyl, C2-C6 alkenyl, cycloalkyl, aryl, heteroaryl, C1-C6 trifluoroalkyl, wherein each of the substituents is independently of each other substituted by any of 0 to 3 groups selected from halogen, amino, hydroxy, mercapto, nitro or cyano; further preferably, $R_2$ is halogen, alkoxy, C1-C6 alkyl, C1-C6 trifluoroalkyl;
$R_2$ may be selected from fluoro, chloro, bromo, methyl, ethyl, trifluoromethyl, trifluoroethyl, trifluoropropyl, and $R_2$ is preferably fluoro, chloro, trifluoromethyl, methyl;

$R_3$ is selected from the following substituents:

(i) aryloxy, amino, —NH-alkyl, —N—$(R_9)(R_{10})$, —NH-aryl, —N-(aryl)$_2$, —NHCOR$_9$, —CO$_2$H, —CO$_2$-alkyl, —CO$_2$-aryl, —CONH—R$_9$, —CON—$(R_9)(R_{10})$, —CONH-alkyl, —CON-(alkyl)$_2$, —SO$_3$H, —CF$_3$, —CO—R$_9$ or —CO-aryl, wherein the groups of alkyl, aryl, aryl-substituted alkyl and heteroaryl ring group are each respectively further substituted by 0 to 3 groups which are preferably selected from halogen, NO$_2$, CN, OH, methoxy, NH$_2$, CO$_2$H, N—$(R_9)(R_{10})$, CONH$_2$, CHF$_2$ and CF$_3$; or (ii) hydrogen, halogen, —CN, —NO, —NO$_2$, —SO$_2$NHR$_9$, CF$_2$H, —OR$_{11}$, —SR$_{13}$, CH$_2$CN, CH$_2$CH$_2$OH, NHCOCH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In some embodiments, the groups of alkyl, aryl, alkyl-substituted aryl and heteroaryl ring group may be further substituted by 0 to 3 groups which are independently selected from halogen, NO$_2$, CN, OH, methoxy, NH$_2$, CO$_2$H, N—$(R_9)(R_{10})$, CONH$_2$ and CF$_3$;

$R_3$ is preferably selected from alkyl unsubstituted or substituted by $R_{25}$, heteroalkyl unsubstituted or substituted by $R_{25}$, cycloalkyl unsubstituted or substituted by $R_{25}$, heterocycloalkyl unsubstituted or substituted by $R_{25}$, aryl unsubstituted or substituted by $R_{25}$, or heteroaryl unsubstituted or substituted by $R_{25}$; $R_3$ may be selected from C1-C10 alkyl, C2-C10 substituted or unsubstituted heteroalkyl;

$R_3$ is further preferably methyl, ethyl, propyl, n-butyl, and preferably methyl;

$R_{25}$ is halogen, —CN, —CF$_3$, —OH, —NH$_2$, —SO$_2$, —COOH, —NO, —SH, —NO$_2$, oxo group, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R_4$ is hydrogen, alkyl, heteroalkyl, substituted alkyl, cycloalkyl, aryl, heteroaryl, cycloalkyl, heterocycloalkyl, arylalkyl, heteroarylalkyl, or COR$_5$, wherein the groups of cycloalkyl, aryl, heteroaryl, cycloalkyl-substituted alkyl, heterocycloalkyl, arylalkyl, or heteroarylalkyl are independently of each other substituted by 0 to 3 groups which are selected from alkyl, halogen, CN, NO$_2$, NH$_2$, NHR$_5$, N(R$_5$)$_2$, SR$_5$, heteroalkyl, alkoxy, hydroxy, heteroalkoxy, CHF$_2$, CF$_3$, OCF$_3$, OCF$_2$H; $R_4$ is preferably hydrogen, aryl, heteroaryl, cycloalkyl, heterocycloalkyl, arylalkyl, heteroarylalkyl, wherein the groups of aryl, heteroaryl, heterocycloalkyl, arylalkyl, heteroarylalkyl are independently of each other substituted by 0 to 3 groups selected from alkyl, halogen, CN, NO$_2$, NH$_2$, heteroalkyl, alkoxy, hydroxy, heteroalkoxy, CHF$_2$, CF$_3$, OCF$_3$, OCF$_2$H; further preferably, $R_4$ is aryl which is substituted by 0 to 3 groups selected from alkyl, halogen, CN, NO$_2$, CHF$_2$, CF$_3$, OCF$_3$, OCF$_2$H;

$R_4$ is preferably phenyl which is substituted by 0 to 3 groups selected from halogen, CF$_3$; and $R_4$ is preferably 3-trifluoromethyl-4-chlorophenyl;

$R_5$ is alkyl, heteroalkyl, substituted alkyl, cycloalkyl, aryl, heteroaryl, cycloalkyl, heterocycloalkyl, arylalkyl, heteroarylalkyl, wherein the groups of cycloalkyl, aryl, heteroaryl, cycloalkyl-substituted alkyl, heterocycloalkyl, arylalkyl, or heteroarylalkyl are independently of each other substituted by 1 to 3 groups which are preferably selected from aryl, halogen, heteroalkyl, alkoxy, heteroalkoxy.

DETAILED DESCRIPTION OF THE INVENTION

The following is a detailed description about some terms used in the present invention.

As described above, the present invention discloses derivatives substituted by urea associated with 4-substituted-(3-substituted-1H-pyrazole-5-amino)-pyrimidine-2-amino. These compounds may be used in vivo or in vitro to regulate or inhibit the activity of capsaicin receptor.

As for the compounds of the present invention, the standard nomenclature is adopted. When the compound has a chiral center, unless otherwise specified, all optical isomers of the compound and mixtures thereof would fall within the protection scope of the present invention. In addition, a compound containing carbon-carbon double bond(s) may have the Z or E configuration(s), unless otherwise specified, all of the isomers would fall within the protection scope of the present invention as well. When the compound has its tautomer and the compound is not limited to being a certain isomer, it can be considered that all of the isomers of the compound are included in the present invention. When some compounds according to the present invention are described by using certain general formulae (e.g., X, Ar), it is considered that the compounds include all of the variable forms thereof. Unless otherwise specified, each of the variable forms is independently of each other selected from a certain range.

As for the present invention, a pharmaceutically acceptable form comprises a pharmaceutically acceptable salt, hydrate, complex formed with solvent(s), crystal form, polymorph, chelate, non-covalent combination, ester and prodrug form thereof, etc. pharmaceutically acceptable salt refers to a salt of an acid form or a base form. Professionally, it is considered that a pharmaceutically acceptable salt is non-toxic, non-irritant, devoid of anaphylaxis or other side-effect to tissues of humans or animals. Such salts include inorganic salts or organic salts of a basic group such as amino, and also include inorganic salts or organic salts of an acidic group such as carboxylic acid. The pharmaceutically acceptable salt includes, but is not limited to, hydrochloride, phosphate, hydrobromide, malate, glycollate, fumarate, sulfate, sulfonate, formate, toluenesulfonate, methylsulfonate, benzenesulfonate, ethyldisulfonate, 2-hydroxyethyl sulfonate, nitrate, benzoate, 2-acetoxybenzoate, citrate, tartrate, lactate, stearate, salicylate, glutamate, ascorbate, methylene pamoate, succinate, maleate, propionates, hydroxymaleate, hydroiodide, benzeneacetate, alkanoate, such as HOOC—$(CH_2)_n$—COOH, wherein n is an integer of 0 to 4. Pharmaceutically acceptable cations include, but are not limited to, sodium ion, potassium ion, calcium ion, aluminum ion, lithium ion and ammonium ion. Such pharmaceutically acceptable salts of an acid or a base may be synthesized from the parent compounds of the acid or base by conventional chemical methods. The salts are obtained by reacting the acid or base in free form of the compound with a certain equivalent of suitable base or acid in water or an organic solvent or their mixture. Typically, the preferred non-water medium is ethylether, ethyl acetate, acetone, ethanol, isopropanol and acetonitrile.

The structure of a "prodrug" is not consistent with the compound according to the present invention. After a prodrug is administrated to a patient, the prodrug can be converted in vivo into the compound included in the general formula. Prodrugs can be derivatives formed with amino, hydroxy or mercapto groups, and these derivatives can be converted back into the amino, hydroxyl or mercapto groups within the organism. For example, the hydroxy and amino groups of the compounds provided by the present invention cam produce corresponding acetylation, formylation, or benzoylation derivatives.

The term "alkyl" refers to straight chain or branched chain saturated aliphatic hydrocarbon. It includes C1-C8 alkyl, C1-C6 alkyl, C1-C4 alkyl, such as methyl, ethyl, propyl, isopropyl, n-butyl, isobutyl, tert-butyl, pentyl, 2-pentyl, isopentyl, neopentyl, hexyl, 2-hexyl, 3-hexyl and 3-methylhexyl. The term "C0-C4 alkyl" refers to a single covalent bond or an alkyl consisting of 1, 2, 3 or 4 carbon atoms. The term "C0-C6 alkyl" refers to a single covalent bond (C0) or C1-C6 alkyl. The term "C0-C8 alkyl" refers to a single covalent bond (C0) or C1-C8 alkyl. In some embodiments, one substituted alkyl is specified. For example, the term "cyano C1-C4 alkyl" refers to a C1-C4 alkyl which may be substituted by at least one cyano group.

The term "alkylene" refers to a divalent alkyl, i.e., a group represented by —(CHR)$_n$—, wherein R is H or alkyl.

The term "alkenyl" refers to straight chain or branched chain alkenyl. The alkenyl functional group includes C2-C8 alkenyl, C2-C6 alkenyl and C2-C4 alkenyl, which respectively contain 2 to 8, 2 to 6 and 2 to 4 carbon atoms, such as vinyl, allyl, isopropenyl. The term "alkynyl" refers to straight chain or branched chain alkynyl, which contains one or more unsaturated carbon-carbon bond and at least one carbon-carbon triple bond. The alkynyl includes C2-C8 alkynyl, C2-C6 alkynyl group, C2-C4 alkynyl, which respectively contain 2 to 8, 2 to 6 and 2 to 4 carbon atoms.

The term "cycloalkyl" refers to saturated cyclic groups totally consisting of carbon atoms (3 to 7), such as cyclopropyl, cyclopentyl and cyclohexyl. Any one of the carbon atoms on the ring may be substituted by any specified substituent. For example, these substituents may be halogen, cyano, C1-C8 alkyl, C1-C8 alkoxy, C2-C8 alkanoyl.

The term "alkoxy" refers to a group wherein the alkyl is linked to the oxygen atom, i.e. a group represented by "alkyl-O-". The alkoxy includes C1-C6 alkoxy and C1-C4 alkoxy, which respectively contain 1 to 6 and 1 to 4 carbon atoms. For example, the alkoxy may be methoxy, ethoxy, propoxy, isopropoxy, n-butoxy, sec-butoxy, tert-butoxy, n-pentoxy, 2-pentoxy, 3-pentoxy, isopentoxy, neopentoxy, n-hexyloxy, 2-hexyloxy, 3-hexyloxy, and 3-methyl-pentoxy.

The term "thiohydrocarbyl" refers to a group wherein the alkyl is linked to the sulfur atom, i.e. a group represented by "hydrocarbyl-S-", including "alkyl-S-", "alkenyl-S-", "alkynyl-S-".

The term "alkylsulfonyl" refers to a group represented by the general formula "—(SO$_2$)-alkyl", wherein the sulfur atom is directly linked to the substituted group. The alkylsulfonyl includes C1-C6 alkylsulfonyl and C1-C4 alkylsulfonyl, which respectively contain 1 to 6 and 1 to 4 carbon atoms. For example, the alkylsulfonyl may be methyl-sulfonyl.

The term "alkylsulfonamide" refers to a group represented by the general formula "—(SO$_2$)N(R)$_2$", wherein the sulfur atom is directly linked to the substituted group and each R is independently of each other selected from hydrogen or alkyl. The term "mono- or di-(C1-C6)alkylsulfonamide means that one of R groups is C1-C6 alkyl and the other one is hydrogen or independently selected from C1-C6 alkyl.

The term "oxo" refers to a ketonic group (C=O). The group "—C(=O)—" is obtained by oxidizing "—CH$_2$-", wherein the non-aromatic carbon atom is substituted by an oxygen atom.

The term "alkanoyl" refers to an acyl which is linked to straight chain or branched chain alkyl (e.g., —(C=O)-alkyl), wherein the carbon atom on carbonyl is directly linked to the substituted group. The alkanoyl includes C2-C8 alkanoyl, C2-C6 alkanoyl and C2-C4 alkanoyl, which respectively contain 2 to 8, 2 to 6 or 2 to 4 carbon atoms. The term "C1 alkanoyl" refers to —(C=O)—H.

The term "alkoxyalkyl" refers to straight chain or branched chain ether substituent. The alkoxyalkyl includes C2-C8 alkoxyalkyl, C2-C6 alkoxyalkyl and C2-C4 alkoxyalkyl, which respectively contain 2 to 8, 2 to 6 and 2 to 4 carbon atoms. For example, the structure of "C2 alkoxyalkyl" is —CH$_2$OCH$_3$.

The term "alkylamino" refers to a secondary or tertiary amine having a structure of —NH-alkyl or —N-(alkyl)(alkyl), wherein each alkyl may be the same or different. For example, mono- or di-(C1-C8)alkylamino may comprise 1 to 8 carbon atoms, wherein each alkyl may be the same or different. Mono- or di-(C1-C6)alkylamino or mono- or di-(C1-C4)alkylamino is similar to the above conditions.

The term "alkylaminoalkyl" refers to an alkylamino linked to an alkyl, such as the structure of "-alkyl-NH-alkyl" or "-alkyl-N-(alkyl)(alkyl)", wherein each alkyl is independent of each other. For example, the alkylaminoalkyl may be mono- and di-(C1-C4 alkyl)amino C1-C8 alkyl, mono- and di-(C1-C6 alkyl)amino C1-C6 alkyl, mono- and di-(C1-C4 alkyl)amino C1-C4 alkyl, wherein each alkyl may be the same or different. "Mono- or di-(C1-C6 alkyl)-amino-C0-C6 alkyl" means the mono- or di-(C1-C6 alkyl)-amino is directly linked to a substituted group or to a C1-C6 alkyl.

The term "aminocarbonyl" refers to an amino having a structure of —(C=O)NH$_2$. The term "mono- or di-(C1-C8 alkyl)aminocarbonyl" refers to an aminocarbonyl of which one or two hydrogen atoms of the amino are substituted by C1-C8 alkyl(s). If both of the two hydrogen atoms on the amino are substituted, the C1-C8 alkyl substituents may be the same or different.

The term "halogen" refers to fluoro, chloro, bromo, iodo.

The term "haloalkyl" refers to a branched chain, straight chain or cyclic alkyl which is substituted by one or more halogen atom(s). For example, "C1-C8 haloalkyl" comprises 1 to 8 carbon atoms, and "C1-C6 haloalkyl" comprises 1 to 6 carbon atoms. The haloalkyl group includes (but not limited to) mono-, di- or tri-fluoromethyl; mono-, di- or tri-chloromethyl; mono-, di-, tri-, tetra- or penta-fluoroethyl; mono-, di-, tri-, tetra- or penta-chloroethyl; 1,2,2,2-tetrafluoro-1-trifluoromethyl-ethyl.

The term "haloalkoxy" refers to a haloalkyl which is linked to the oxygen atom. The "C1-C8 haloalkoxy" comprises 1 to 8 carbon atoms.

The symbol "—" does not link two letters or symbols, but refers to a bonding point between the substituted groups and the substituents. For example, "—CONH$_2$" means directly linking to a carbon atom.

The term "hetero atom" refers to oxygen, sulfur, or nitrogen atoms.

The term "heterocycloalkyl" refers to a saturated cyclic alkyl which contains at least one hetero atom on the ring. The "heterocycloalkyl" includes such as morpholinyl, thiomorpholinyl, tetrahydropyranyl.

The term "carbocycle" or "carbocyclic group" refers to a group which comprises at least one cyclic group which is totally consisted of carbon-carbon bonds and does not contain a heterocycle. Unless otherwise specified, each carbocycle may be saturated, partially saturated or aromatic. The carbocycle typically has 1 to 3 fused ring(s), bridged ring(s) or spirocyclic compound(s), especially C3-C8 carbocycle and C5-C7 carbocycle. The carbocycle further comprises 9-14 membered fused ring, bridged ring or spirocyclic compound. Some representative carbocycles are cycloalkyls (referring to saturated and/or partially saturated carbocycles, such as cyclopropyl, cyclobutyl, cyclopentyl, cyclohexyl, cycloheptyl, cyclooctyl, adamantanyl, decahydronaphthyl, octahydroindenyl and various partially-saturated carbocycles mentioned above, such as cyclohexenyl), as well as aromatic rings (a group containing at least one aromatic ring, such as phenyl, benzyl, naphthyl, phenoxy, benzoyloxy, acetophenone group, fluorenyl, indenyl and 1,2,3,4-tetrahydronaphthyl). The carbon atoms on the carbocycle may be substituted by 0, 1 or 2 hydrogen atoms and/or any substituent, such as hydroxy, halogen, cyano, nitro, C1-C8 alkyl, C2-C8 alkenyl, C2-C8 alkynyl, C1-C8 alkoxy, C2-C8 alkoxyalkyl, C3-C8 alkanonyl, C1-C8 thiohydrocarbonyl, amino, mono- or di-(C1-C8 alkyl)amino, C3-C7 cycloalkyl, C0-C4 alkyl, hetero C1-C8 alkyl, hetero C1-C8 alkoxy, amino C1-C8 alkyl, hydroxy C1-C8 alkyl, C1-C8 alkanoyl, C1-C8 alkoxycarbonyl, —COOH, —C(C═O)NH$_2$, mono- or di-(C1-C8 alkyl) amide, —S(O$_2$)NH$_2$, mono- or di-(C1-C8 alkyl)sulfonamide.

Some carbocycles described in the present invention comprise C6-C10 aryl C0-C6 alkyl (wherein at least one aromatic ring is directly linked to the parent compound or firstly linked to C1-C6 alkyl and then to the parent compound). For example, phenyl and indenyl are respectively linked to phenyl and indenyl through C1-C4 or C1-C6 alkyl. Where a phenyl is linked to a parent compound directly or through an alkyl, it can be represented as phenyl-C0-C6 alkyl (e.g., benzyl, 1-phenyl-ethyl, 1-phenyl-propyl and 2-phenyl-ethyl).

The term "heterocycle" or "heterocycloalkyl" refers to 1 to 3 fused ring(s), bridged ring(s), spirocyclic compound(s) containing at least one heterocycle (which contains one or more hetero atoms on the ring, and the other atoms on the ring are carbon atoms). The heterocycle contains 1 to 4 hetero atoms, and in some embodiments, each heterocycle contains 1 or 2 hetero atoms. The heterocycle comprises 9-14 membered fused ring, bridged ring or spirocyclic compound. The heterocycle may optionally be substituted by nitro and/or various substituents on carbon atoms, such as the above-mentioned carbocycle. Unless otherwise defined, the heterocycle may be a heterocycloalkyl (each ring is saturated or partially saturated) or heteroaryl (at least one ring within the group is aromatic). The heterocycle may be linked with other groups in stable forms via any ring or atom. The term "heterocyclo-C0-C8 alkyl" refers to a heterocycle which is linked to a parent compound directly or via C1-C8 alkyl. The term "(3-10 membered heterocyclo)-C1-C6 alkyl" refers to a 3-10 membered heterocycle linked to a parent compound via C1-C6 alkyl.

The heterocycle includes, such as acridinyl, azacycloheptyl, azocinyl, benzimidazolyl, benzimidazolinyl, benzisothiazolyl, benzisoxazolyl, benzofuranyl, benzothienyl, benzoxazolyl, benzotriazolyl, benzotriazolyl carbazolyl, benzotetrazolyl, NH-carbazolyl, carbolinyl, benzodihydrofuryl, benzopyranyl, cinnolinyl, decahydroquinolyl, dihydrofuro[2,3-b]tetrahydrofuran, dihydro-isoquinolyl, 1,4-dioxa-8-aza-spiro[4,5]-8-decyl, dithiazinyl, furanyl, furazanyl, imidazolinyl, imidazolidinyl, imidazolyl, indazolyl, indolyl, indolinyl, indolizinyl, indolyl, isobenzofuranyl, isobenzodihydrofuranyl, isodihydroazaindenyl, isoindolyl, isothiazolyl, isoxazolyl, isoquinolyl, morpholinyl, 1,5-naphthyridinyl, octahydroquinolyl, oxadiazolyl, oxazolyl, phenanthridinyl, phenanthroliny, phenazinyl, phenothiazinyl, phenoxthinyl, phenoxazinyl, 2,3-diazanaphthyl, piperazinyl, piperidyl, piperidonyl, pteridinyl, purinyl, pyranyl, pyrazinyl, pyrazolidinyl, pyrazolinyl, pyrazolyl, pyridazinyl, pyridoimidazolyl, pyridoisoxazolyl, pyridothiazolyl, pyridyl, pyrimidinyl, pyrrolidinyl, pyrrolidonyl, pyrrolinyl, pyrrolyl, quinazolinyl, quinolyl, quinoxalinyl, quinuclidinyl, tetrahydroisoquinolyl, tetrahydroquinolyl, tetrazolyl, thiadiazinyl, thiadiazolyl, thianthrenyl, thiazolyl, thienothiazolyl, thienooxazolyl, thienoimidazolyl, thienyl, thiomorpholinyl, and various groups wherein the sulfur atoms are oxidized.

The term "substituent" refers to a molecular fragment which is bonded to a certain atom of the parent compound via a covalent bond. The substituted group can be stable existed (which can be separated, structurally characterized, subject to biological activity tests). For example, the term "a substituent on the ring" refers to halogen, alkyl, haloalkyl or other groups which is bonded to the carbon or nitrogen atom on the ring via a covalent bond.

The term "optionally substituted" means that one or more substituents are substituted optionally on any one or more non-hydrogen position(s), especially on position 1, 2, 3, 4, 5, and the substituents may be the same or different. For example, the substituent can be hydroxy, halogen, cyano, nitro, C1-C8 alkanonyl, C2-C8 alkoxy, C2-C8 alkoxyalkyl, C3-C8 alkanonyl, C1-C8 thiohydrocarbonyl, amino, mono- or di-(C1-C8 alkyl) amino, C1-C8 haloalkyl, C1-C8 alkanoyl, C2-C8 alkanoyloxy, C1-C8 alkoxycarbonyl, —COOH, —CONH$_2$, mono- or di-(C1-C8 alkyl)aminocarbonyl, —SO$_2$NH$_2$, and/or mono- or di-(C1-C8 alkyl)aminosulfonyl, carbocycle, heterocyclic substituent. The term "optionally substituted" can also be expressed as "substituted by 0 to x substituents", wherein x is the maximum number of the substituents.

The term "aryl" refers to an aromatic monocycle or fused bicycle, wherein each ring contains 6 to 10 carbon atoms. For example, the aryl is a phenyl or naphthalenyl. The "arylene" is a divalent group of the aryl.

The term "heteroaryl" refers to an aromatic ring containing one or more heteroatoms on the ring. For example, the heteroaryl is C1-C10 heteroaryl, including pyridyl, indolyl, indazolyl, quinoxalinyl, quinolyl, benzofuranyl, benzopyranyl, benzothiopyranyl, benzo[1,3]-2-oxazolyl, imidazolyl, benzimidazolyl, pyrimidinyl, furanyl, oxazolyl, isoxazolyl, thiazolyl, triazolyl, tetrazolyl, pyrazolyl, thienyl and so on.

The preferred compound of formula I is selected from the compounds of the following structures:

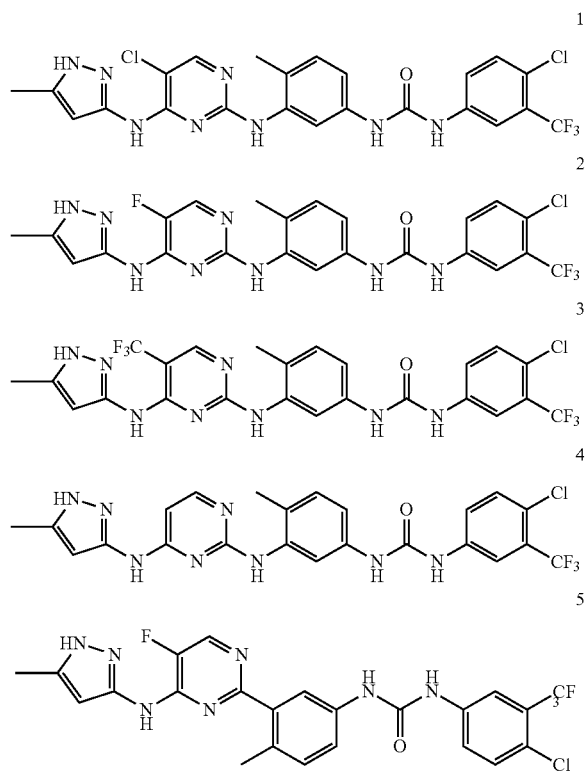

-continued

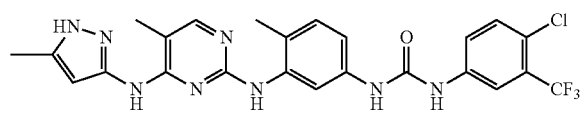
5

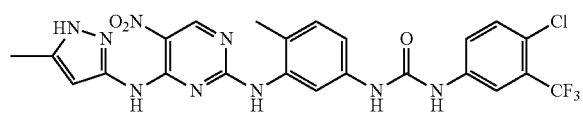
7

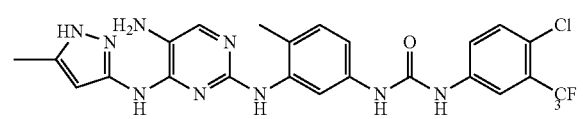
8

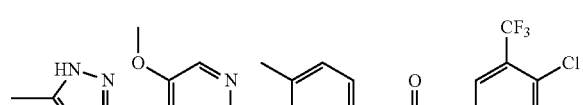
9

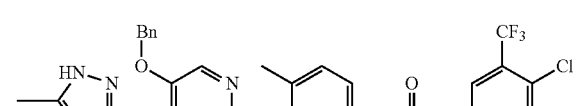
10

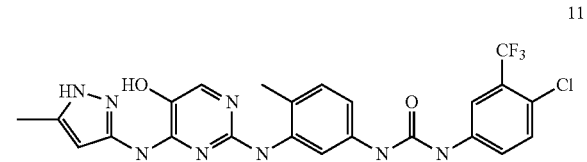
11

Another object of the present invention is to provide a new compound of formula IX, which has the following general formula:

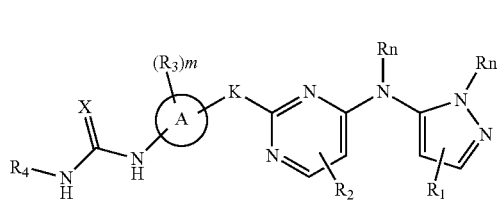
IX wherein, K, A, m, $R_1$, $R_2$, $R_3$, and $R_4$ are defined as the compound of formula I, Rn and Rn' are respectively H or Boc, and X is O, S;

the compound of formula IX is preferably a compound of the following structures:

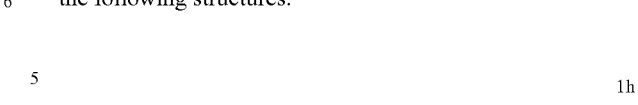
1h

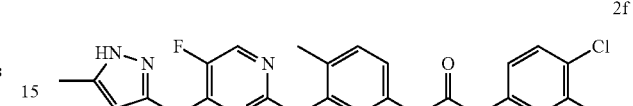
2f

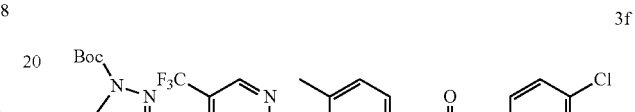
3f

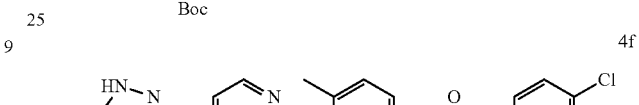
4f

5f

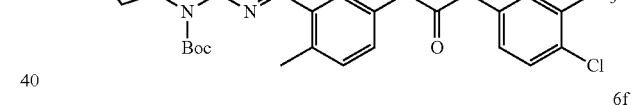
6f

Another object of the present invention is to provide a new compound of formula VIII, which has the following general formula:

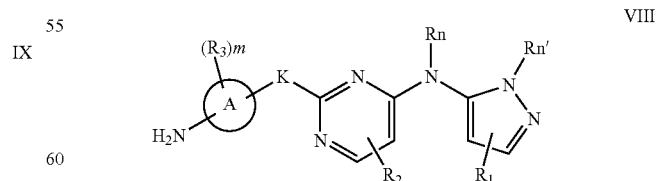
VIII wherein, K, A, m, $R_1$, $R_2$, $R_3$, Rn, and Rn' are defined as the compound of formula IX;

the compound of formula VIII is preferably a compound of the following structures:

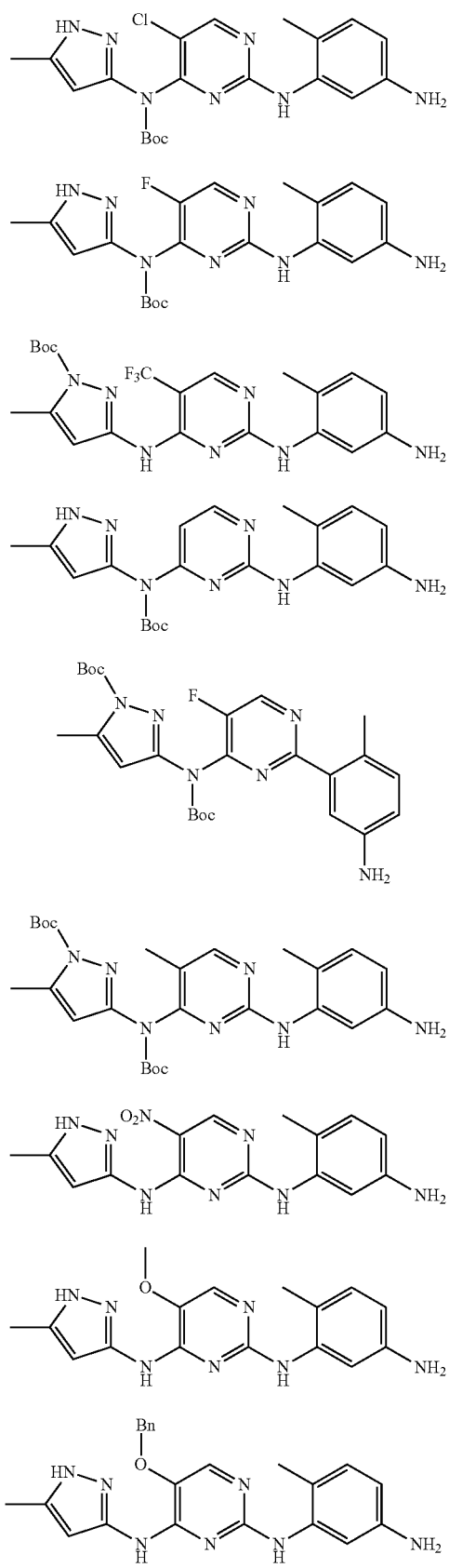
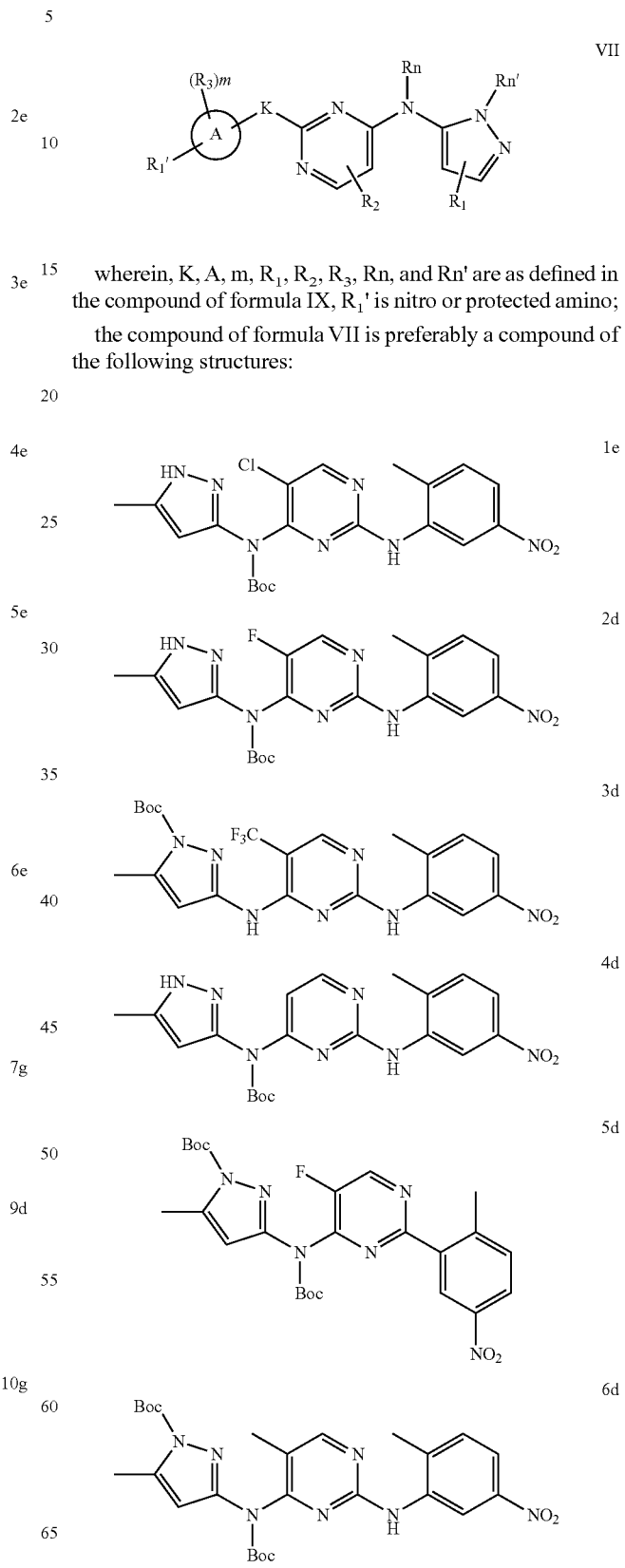
Another object of the present invention is to provide a new compound of formula VII, which has the following general formula:
wherein, K, A, m, $R_1$, $R_2$, $R_3$, Rn, and Rn' are as defined in the compound of formula IX, $R_1$' is nitro or protected amino;
the compound of formula VII is preferably a compound of the following structures:

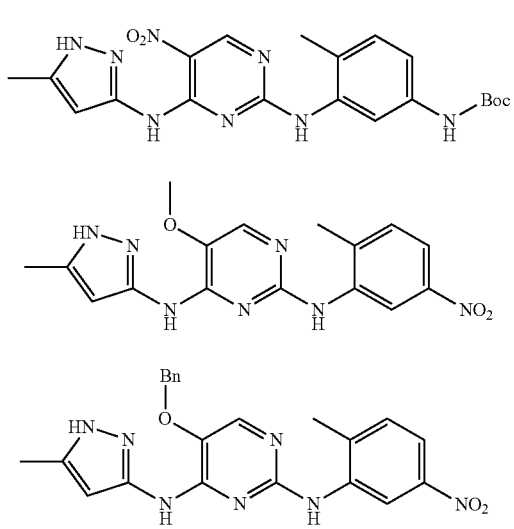

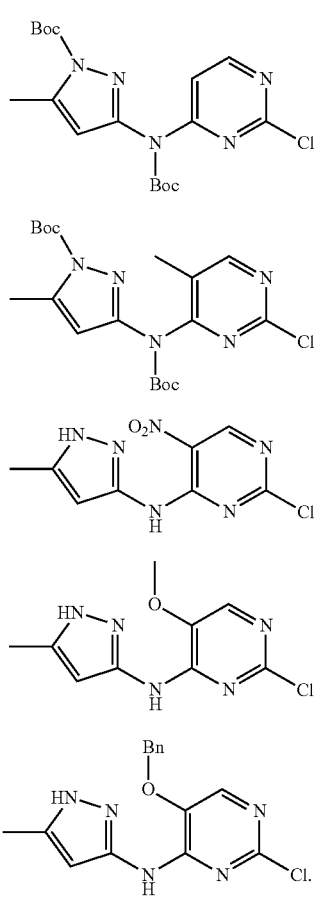

Another object of the present invention is to provide a new compound of formula V, which has the following general formula:

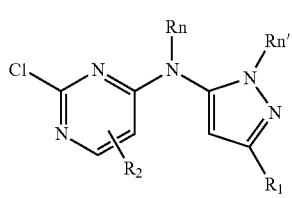

wherein, $R_1$, $R_2$, Rn, and Rn' are defined as the compound of formula IX;

the compound of formula V is preferably a compound of the following structures:

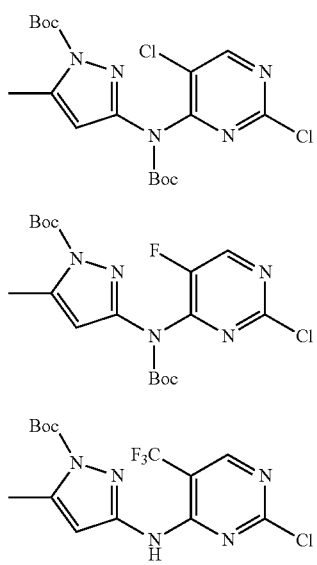

Another object of the present invention is to provide a pharmaceutical composition comprising a compound of formula I, a pharmaceutical acceptable salt thereof, a hydrate thereof, a solvate thereof, and the composition may be existed in any acceptable oral-dosed or injectable preparation form.

The above oral preparation is selected from capsule, tablet, suppository, suspension, syrup, aqueous suspension or solution.

Another object of the present invention is to provide the use of a compound of formula I in the manufacture of a therapeutic or prophylactic medicament for the treatment or prophylaxis of various diseases associated with protein kinases, wherein the diseases are selected from one or more of the following: cell abnormal proliferation, cell abnormal metabolism, cell degeneration, hepatitis C and anaphylaxis.

Another object of the present invention is to provide the use of a compound of formula I in the manufacture of a therapeutic or prophylactic medicament for use in the treatment or prophylaxis of various diseases associated with protein kinase and the uses of the compounds of formulae IX, VIII, VII and V in the manufacture of the compound of formula I.

Preparation of the Compounds of the Invention

The preparation methods of the compounds in the present invention are described in detail hereinafter. The compound of formula I includes various stereo isomers, geometric isomers and tautomeric isomers. It will be understood that the invention encompasses all of the isomers.

The derivatives substituted by urea associated with 4-substituted-(3-substituted-1H-pyrazole-5-amino)-pyrimidine-2- amino can be synthesized by conventional methods. All raw materials are commercially available or they are prepared by standard processes known in the art.

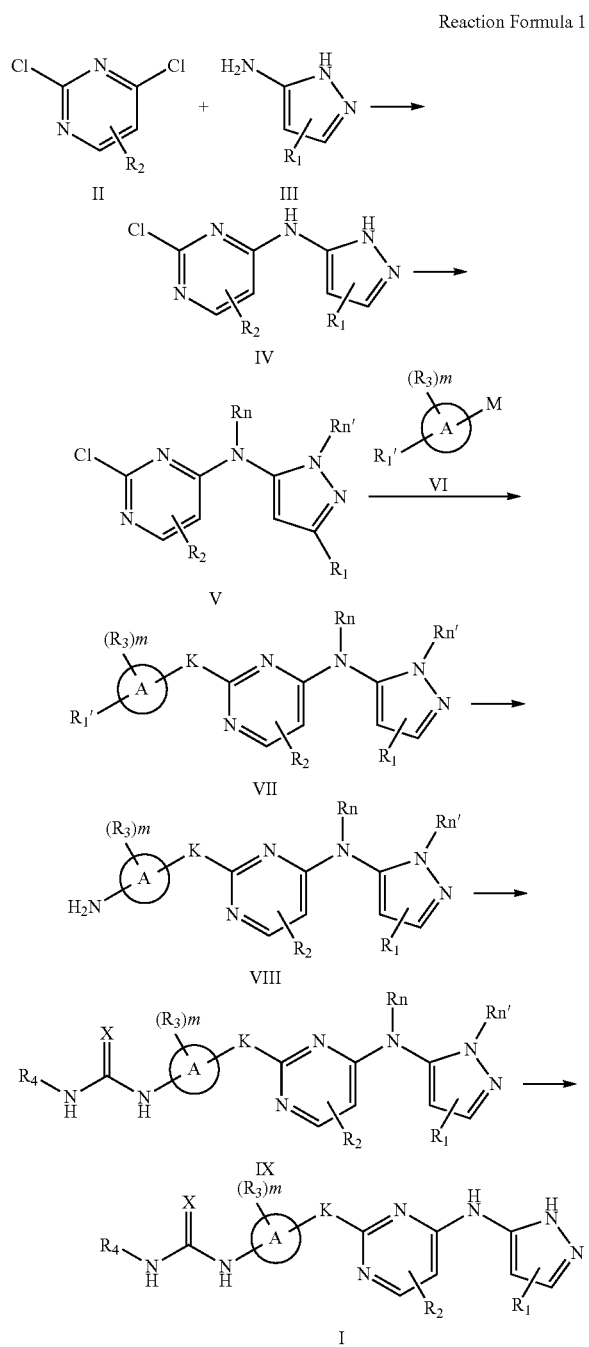

Reaction Formula 1

Reaction Formula 1 represents a synthesis method of the compound of formula I: the chlorine atom of dichloropyrimidine derivative (the compound of formula II) is substituted by a heterocyclic amine (the compound of formula III) to form a corresponding pyrimidine derivative (the compound of formula IV); optionally the pyrimidine derivative (the compound of formula IV) is reacted with an amino-protecting agent to form a compound of formula V; a corresponding nitro-containing disubstituted or trisubstituted pyrimidine derivative (the compound of formula VII) is obtained by coupling reaction between a nitro-substituted aryl amine or a boric acid or the ester thereof which has a similar structure (the compound of formula VI, wherein $R_1'$ is nitro or protected amino, m is an integer of 0 to 4, M is selected from $-B(OH)_2$ or $-B(OR')_2$, R' represents alkyl) and the compound of formula V; under certain conditions, the compound of formula IV can be directly reacted with the compound of formula VI (wherein $R_1'$ is nitro or protected amino) to form the corresponding compound of formula VII; when $R_1'$ is nitro, the compound of formula VII is hydrogenated by a palladium on carbon catalyst or other standard processes to reduce the nitro thereof to amino to form the corresponding compound of formula VIII; alternatively, when $R_1'$ is a protected amino, the compound of formula VII is subjected to a conventional method of removing the amino-protecting group to form the corresponding compound of formula VIII; then, the compound of formula VIII is reacted with various isocyanate or isothiocyanate to form the corresponding compound of formula IX, the resulting compound of formula IX is deprotected under acidic conditions to form urea or thiourea derivatives of 4-substituted-(3-substituted-1H-pyrazole-5-amino)-pyrimidine-2-amino (the compound of formula I); in certain cases, $R_2$ is converted into other group(s) by chemical conversions to form the corresponding desired compound (the compound of formula I).

Generally, inert solvents with better solubility are preferably used in the experiments. Such inert solvents are aliphatic hydrocarbons, such as n-hexane, n-heptane and petroleum ether; aromatic hydrocarbons, such as benzene, toluene and xylene; halogenated hydrocarbons, especially aromatic and aliphatic halogenated hydrocarbons, such as dichloromethane, chloroform, trichloromethane, carbon tetrachloride, 1,2-dichloroethane, chlorobenzene and dichlorobenzene; esters, such as ethyl acetate, propyl acetate, butyl acetate and diethyl carbonate; ethers, such as diethyl ether, diisopropyl ether, tetrahydrofuran, dioxane, dimethoxyethane, dimethyl diglycol; ketones, such as acetone, methyl ethyl ketone, methyl isobutyl ketone, isophorone and cyclohexanone; nitro compounds, nitroalkane, and nitro aromatic compounds, such as nitroethane, nitrobenzene; nitriles, such as acetonitrile and isobutyronitrile; amino compounds, fatty acid amines, such as formamide, dimethyl amide, dimethylacetamide and hexamethylphosphoric triamide; sulfoxides, such as dimethyl sulfoxide and cyclobutyl sulfone.

The experimental temperature range is comparatively broad and the range is typically between –50° C. to 100° C.

The present invention provides a preparation and pharmaceutical carrier composed of one or more active compounds. The present invention also provides a pharmaceutical component which comprises a compound as represented by general formula I or a pharmaceutically acceptable salt thereof.

The compounds of the present invention may exist in any acceptable oral-dosed preparation form. Such preparation form includes (but is not limited to) capsule, tablet, suppository, suspension, syrup, aqueous suspension or solution.

Oral drugs contain some additives, for example, binders, such as microcrystalline cellulose, tragacanth, gelatin; excipients, such as starch and lactose; disintegrating agents, such as alginic acid, corn starch; lubricants, such as magnesium stearate; glidants, such as colloidal silica; sweetening agents, such as sucrose, saccharin; flavoring enhancer agents, such as peppermint oil, methyl salicylate, orange flavor. When the preparation is a capsule, a liquid transfer medium, such as a fatty oil, may be added. Other preparations also relate to a variety of different physical forms, such as sugar coat. The tablet and pill may be coated with sugar coat, shellac or casing. Pharmaceutical additives in addition to the active ingredients in syrup must be pharmaceutically pure and devoid of toxic and side effects.

According to the regulations of drugs for injection, the active ingredients of these drugs must match with the solvents thereof. Such solvents include the following kinds: sterile diluents, such as water for injection, saline, non-volatile oil, polyethylene glycol, glycerine, propanediol or other synthetic solution; antibacterial agents, such as benzyl alcohol, methyl benzoate; antioxidants, such as ascorbic acid, sodium bisulfite; chelating agents, such as ethylene diamine tetraacetic acid; buffers, such as acetates, citrates or phosphates; modifiers, such as sodium chloride.

Drugs for injection must use sterile solution, dispersant, emulsion, disinfection powder. The finished drugs must be stably exited in the processes of processing, manufacturing and storing. The finished drugs further need to be protected to inhibit the growth of bacteria, fungi and other microorganisms.

Pharmaceutical carriers include sterile water, saline, glucose, aqueous solution of glucose or saline solution, a mixture of epoxyethane and castor oil in a molar ratio of 30-35 mol of epoxyethane to 1 mol of castor oil, acidic liquid, lower alkanols, mono- or a diglycerol fatty acids, phospholipids, such as lecithin, ethanediol, polyethyleneglycol, e.g., an aqueous suspension form of methyl cellulose sodium, sodium alginate, polyethylene.

The carriers further include adjuvant, such as stabilizers, wetting agents, emulsifiers and the like which is advantageous to penetration. The drugs for injection must be sterilized and smoothly flow through the hollow needle for injection. Appropriate adjustments to viscosity can be made on the basis of the selection of solvents or excipients. For example, the coating using lecithin as pharmaceutical molecules or particles may maintain an appropriate viscosity. Like lecithin, suitable selections of the size of the dispersed particles and the surface properties of the material can be employed.

EXAMPLES

The following examples illustrate the present invention more detailedly, however, the present invention is not limited to these examples. All experiments were carried out under anhydrous and argon protection conditions and operated in accordance with water-free and oxygen-free standards. Both the sodium carbonate aqueous solution and the sodium chloride aqueous solution to be used were saturated. Reactions were monitored by the chromogenic reaction under UV on silica gel plates of p-methoxybenzaldehyde, potassium permanganate or phosphomolybdic acid solution.

The data from 400 MHz NMR are used for the characterization of compound. Characterization constants are expressed as follows: chemical shift, multiplicity (s, singlet; d, doublet; t, triplet; q, quartet; qn, quintet; dd, double doublets; m, multiplet; brs, broad singlet), coupling constant (J/Hz), peak area. The coupling constant is calculated from the spectrogram without correction. Low-resolution mass spectrometry employs electrospray $ES^+$ ion source ($ES^+$). The ionized ion peak is the maximum value of mass-to-charge ratio of [M+H], [M+Na] or the fragment ions.

High performance liquid chromatography was applied to analyze compounds. SHIMADZU SPD-M10A diode array detector was used, wherein the type of analytical column was Phenomenex Synergi Polar-RP, 4u. 80A, 150×4.6 mm. Mobile phase A was water, B was acetonitrile, the gradient was 20% to 80% in water, 60 minutes, and A/B (80:20) was balanced for 10 minutes. The wavelengths of UV detector were 220 and 254 nm respectively.

Example 1

Synthesis of 1-{3-[5-chloro-4-(5-methyl-1H-pyrazol-3-yl-amino)-pyrimidin-2-yl-amino]-4-methyl-phenyl}-3-(4-chloro-3-trifluoromethyl-phenyl)-urea (Compound 1)

Synthesis Route:

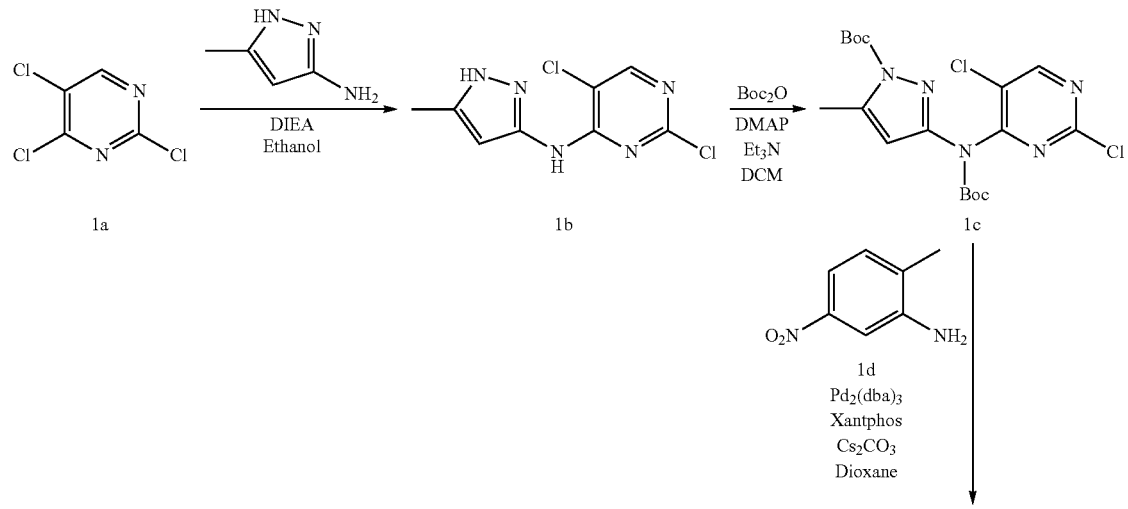

-continued

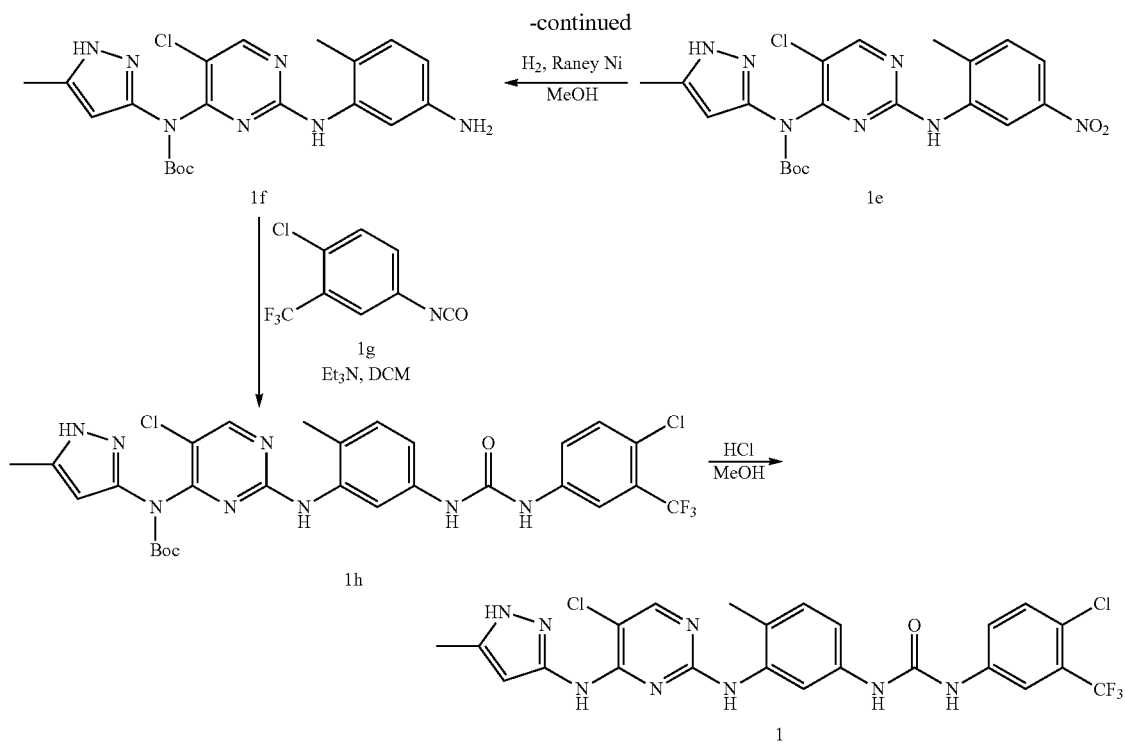

Step 1:

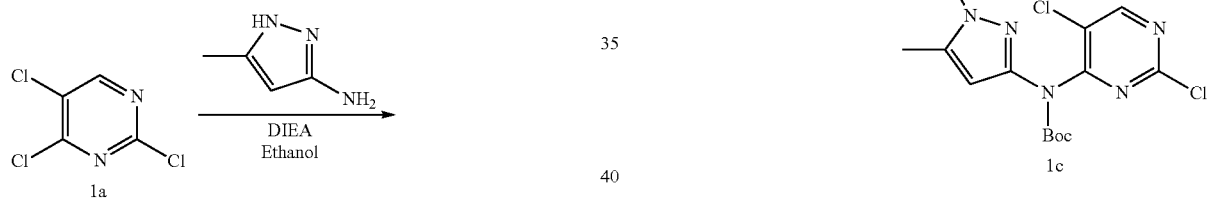

Compound 1a (3.64 g. 20 mmol), 3-amino-5-methyl-pyrazole (1.94 g, 20 mmol) and diisopropylethylamine (5.17 g, 40 mmol) were added to 20 mL of ethanol solution and then stirred at room temperature for 2 days. The insoluble substance was collected to obtain Compound 1b (3.7 g, Yield 76%), MS [M+1]$^+$ 244.0.

Step 2:

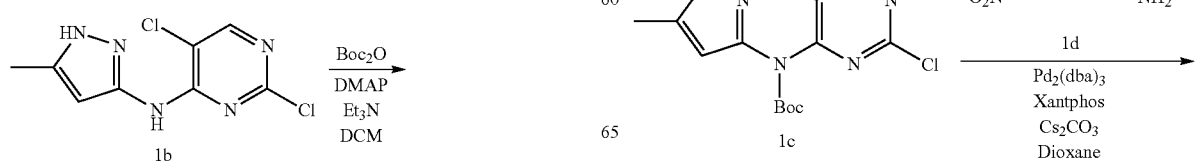

Compound 1b (3.7 g, 15.2 mmol), Et$_3$N (3.8 g, 38 mmol), DMAP (464 mg. 3.8 mmol) were dissolved into 150 mL of dichloromethane, and then Boc$_2$O (8.2 g, 38 mmol) was added dropwise to the solution. The mixture was stirred overnight at room temperature. The solvent was concentrated, and the remainder was purified by silica gel column chromatography to obtain Compound 1c (5 g, Yield 74%), MS [M+1]f 444.0.

Step 3:

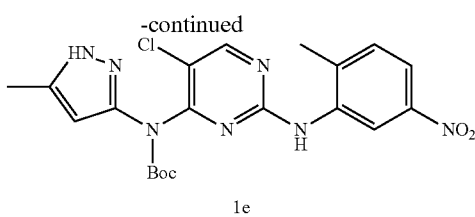

1e

Compound 1c (532 mg, 1.2 mmol), 1d (201 mg, 1.32 mmol), Pd$_2$(dba)$_3$ (114 mg, 0.12 mmol), xantphos (138 mg, 0.24 mmol), Cs$_2$CO$_3$ (786 mg, 2.4 mmol) and dioxane (5 ml) were added to a degassed flask and then heated to reflux for 3 hours under the protection of argon. The solvent was concentrated, and the remainder was purified by silica gel column chromatography to obtain Compound 1e (260 mg. Yield 47%). MS [M+1]$^+$ 460.0.

Step 4:

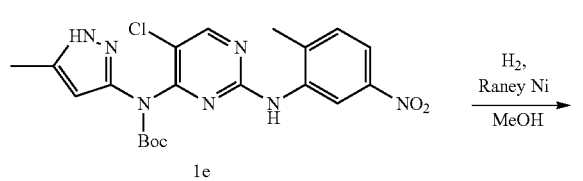

1e mined by LC-MS, the solid was filtered out and the filtrate was concentrated to obtain crude Compound 1f (120 mg, Yield 64%), MS [M+1]$^+$ 430.0.

Step 5:

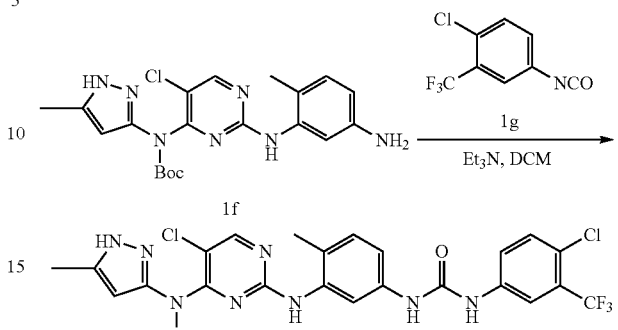

1h

Compound 1f (160 mg, 0.37 mmol), 1 g (103 mg, 0.46 mmol) and triethylamine (75 mg, 0.74 mmol) were dissolved in 10 mL of anhydrous dichloromethane and then stirred at room temperature for 2 hours. The solvent was concentrated, and the remainder was purified by silica gel column chromatography to obtain Compound 1h (170 mg, Yield 70%), MS [M+1]$^+$ 651.0.

Step 6:

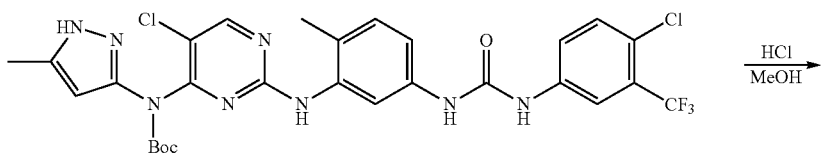

1h

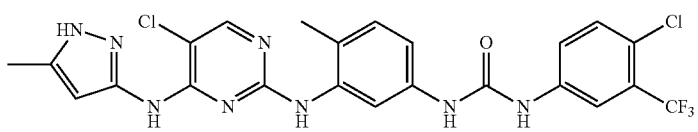

1

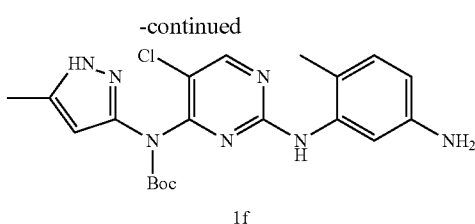

1f

Compound 1e (200 mg, 0.43 mmol) and 200 mg Raney nickel were added to 50 mL of methanol and then reacted overnight at room temperature under 2 atm of hydrogen atmosphere. After the formation of reactant product was deter- Compound 1h (170 mg, 0.26 mmol) was added to a methanol solution of 10 mL of 2 M hydrochloric acid and then the mixture was stirred overnight at room temperature. The insoluble solid was collected and washed with ethyl acetate to obtain hydrochloride of 1-{3-[5-chloro-4 (5-methyl-1H-pyrazol-3-yl-amino)-pyrimidin-2-yl-amino]-4-methyl-phenyl}-3-(4-chloro-3-trifluoromethyl-phenyl)-urea (Compound 1) (40 mg, Yield 28%). $^1$H NMR (400 MHz, CD$_3$OD): δ ppm 8.14 (s, 1H), 8.03 (d, J=2.4, 1H). 7.69 (s, 1H), 7.62 (dd, J$_1$=2.4, J$_2$=8.8, 1H), 7.52 (d, J=8.8, 1 H), 7.36 (s, 2H), 6.40 (s, 1H), 2.32 (s, 3H), 2.28 (s, 3H); MS [M+1]$^+$ 551.1.

Example 2
Synthesis of 1-(4-chloro-3-trifluoromethyl-phenyl)-3-{3-[5-fluoro-4-(5-methyl-1H-pyrazol-3-yl-amino)-pyrimidin-2-yl-amino]-4-methyl-phenyl}-urea (Compound 2)
Synthesis Route 2:
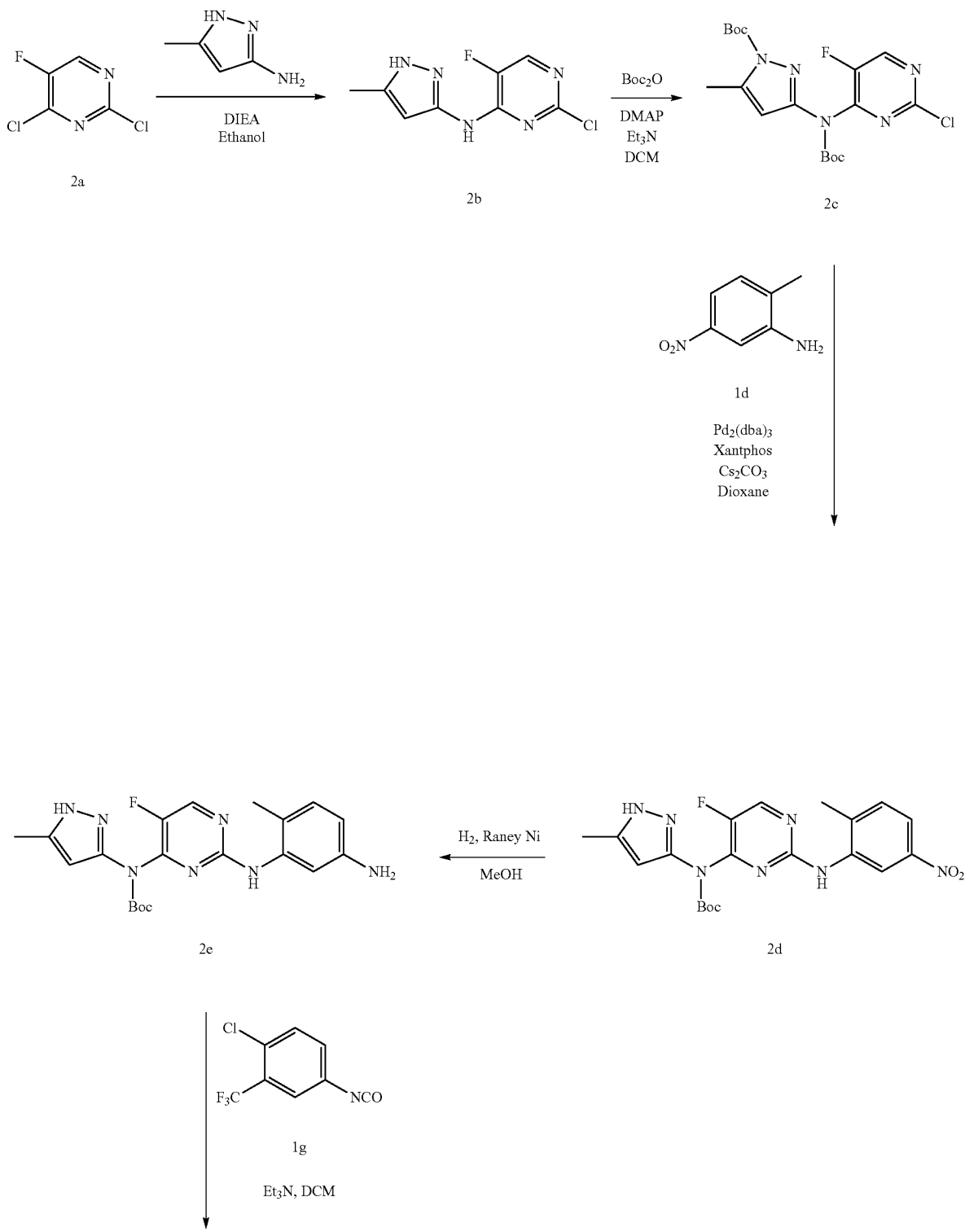

-continued

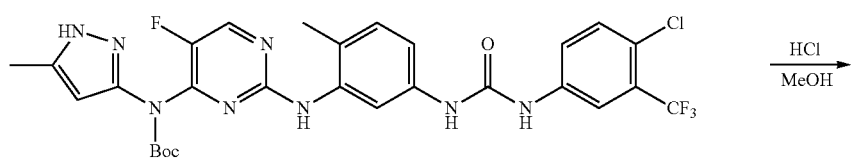

2f

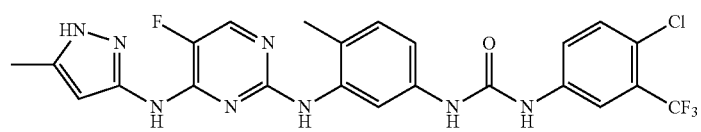

2

Step 1:

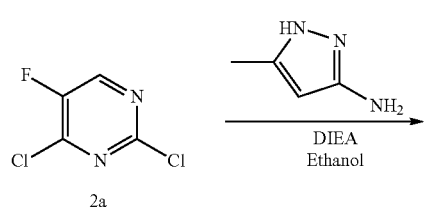

2a

2b

Compound 2a (3.32 g, 20 mmol), 3-amino-5-methylpyrazole (1.94 g, 20 mmol) and diisopropylethylamine (5.17 g 40 mmol) were added to a solution of 20 mL of ethanol and then stirred at room temperature for 2 days. The insoluble substance was collected to obtain Compound 2b (3.9 g. Yield 86%), MS [M+1]+ 228.0

Step 2:

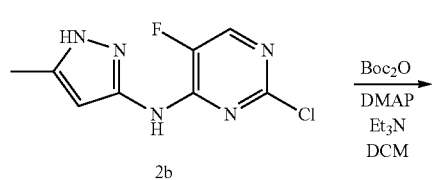

2b

-continued

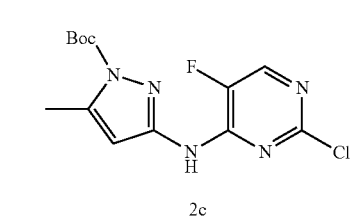

2c

Compound 2b (3.9 g, 17.2 mmol), Et₃N (4.1 g, 40.75 mmol), DMAP (457 mg, 3.78 mmol) were dissolved in 150 mL of dichloromethane, and then Boc₂O (8.2 g, 38 mmol) was added dropwise to the solution. The mixture was stirred overnight at room temperature. The solvent was concentrated, and the remainder was purified by silica gel column chromatography to obtain Compound 2c (6 g, Yield 83%), MS [M+1]+ 428.0.

Step 3:

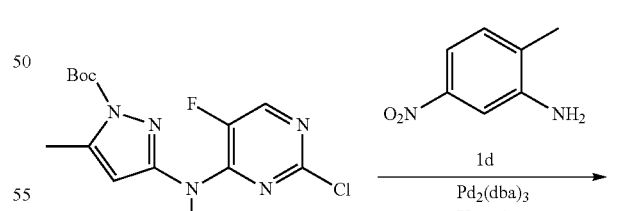

2c

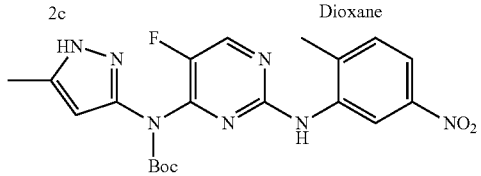

2d

Compound 2c (1.07 g, 2.5 mmol), Compound 1d (419 mg, 2.75 mmol), Pd$_2$(dba)$_3$ (238 mg, 0.25 mmol), xantphos (289 mg, 0.5 mmol), Cs$_2$CO$_3$ (1.64 g, 5 mmol) and dioxane (25 mL) were added to a degassed flask and then heated to reflux for 3 hours under the protection of argon. The solvent was concentrated, and the remainder was purified by silica gel column chromatography to obtain Compound 2d (600 mg, Yield 60%), MS [M+]$^+$ 444.1.

Step 4:

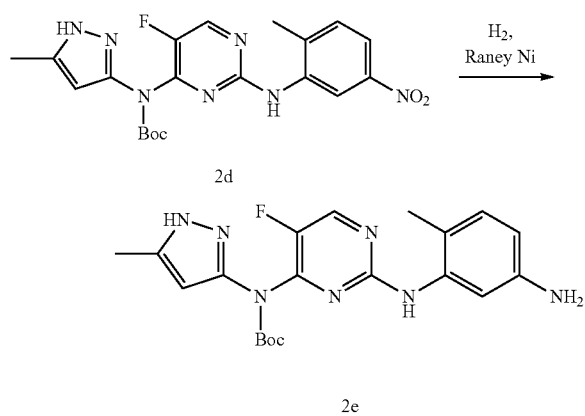

Step 5:

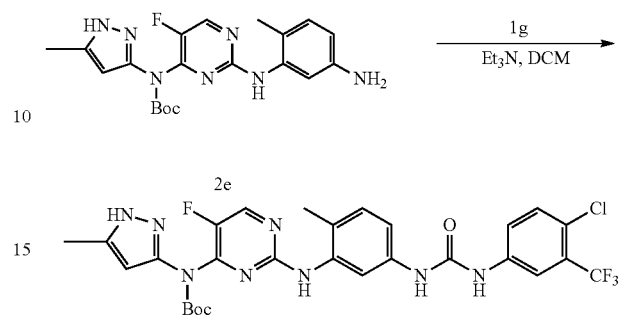

Compound 2e (150 mg, 0.36 mmol), Compound 1 g (96 mg, 0.43 mmol) and triethylamine (75 mg, 0.74 mmol) were dissolved in 10 mL of anhydrous dichloromethane and then stirred at room temperature for 2 hours. The solvent was concentrated, and the remainder was purified by silica gel column chromatography to obtain Compound 2f (170 mg, Yield 48%). MS [M+1]$^+$ 635.1.

Step 6:

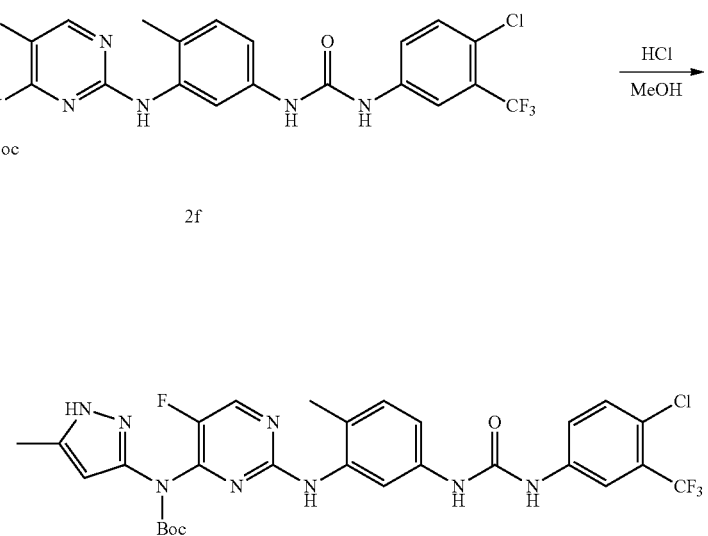

Compound 2d (600 mg. 1.35 mmol) and 400 mg of Raney nickel was added to 50 mL of methanol and reacted overnight at room temperature under 2 atm of hydrogen atmosphere. After the formation of reactant product was determined by LC-MS, the solid was filtered out and the filtrate was concentrated to obtain crude Compound 2e (340 mg, Yield 61%). MS [M+1]$^+$ 414.1.

Compound 2f (110 mg, 0.17 mmol) was added to a methanol solution of 10 mL of 2 M hydrochloric acid and then stirred overnight at room temperature. The insoluble solid was collected and washed with ethyl acetate to obtain hydrochloride of 1-(4-chloro-3-trifluoromethyl-phenyl)-3-{3-[5-fluoro-4-(5-methyl-1H-pyrazol-3-ylamino)-pyrimidin-2-yl-amino]-4-methyl-phenyl}-urea (Compound 2) (27 mg, Yield 30%). $^1$H NMR (400 MHz, CD$_3$OD): δ ppm 8.02 (d, J=2.8, 1 H), 7.98 (d. J=5.6, 1 H), 7.68 (s, 1H). 7.60 (dd, J$_1$=2.8, J$_2$=8.8, 1H), 7.52 (d, J=8.8, 1H). 7.35 (2H), 6.33 (s, 1H), 2.30 (s, 6H); MS [M+1]$^+$ 535.1.

Example 3
Synthesis of 1-(4-chloro-3-trifluoromethyl-phenyl)-3-{4-methyl-3-[4-(5-methyl-1H-pyrazol-3-yl-amino)-5-trifluoromethyl-pyrimidin-2-yl-amino]-phenyl}-urea (Compound 3)
Synthesis Route 3:
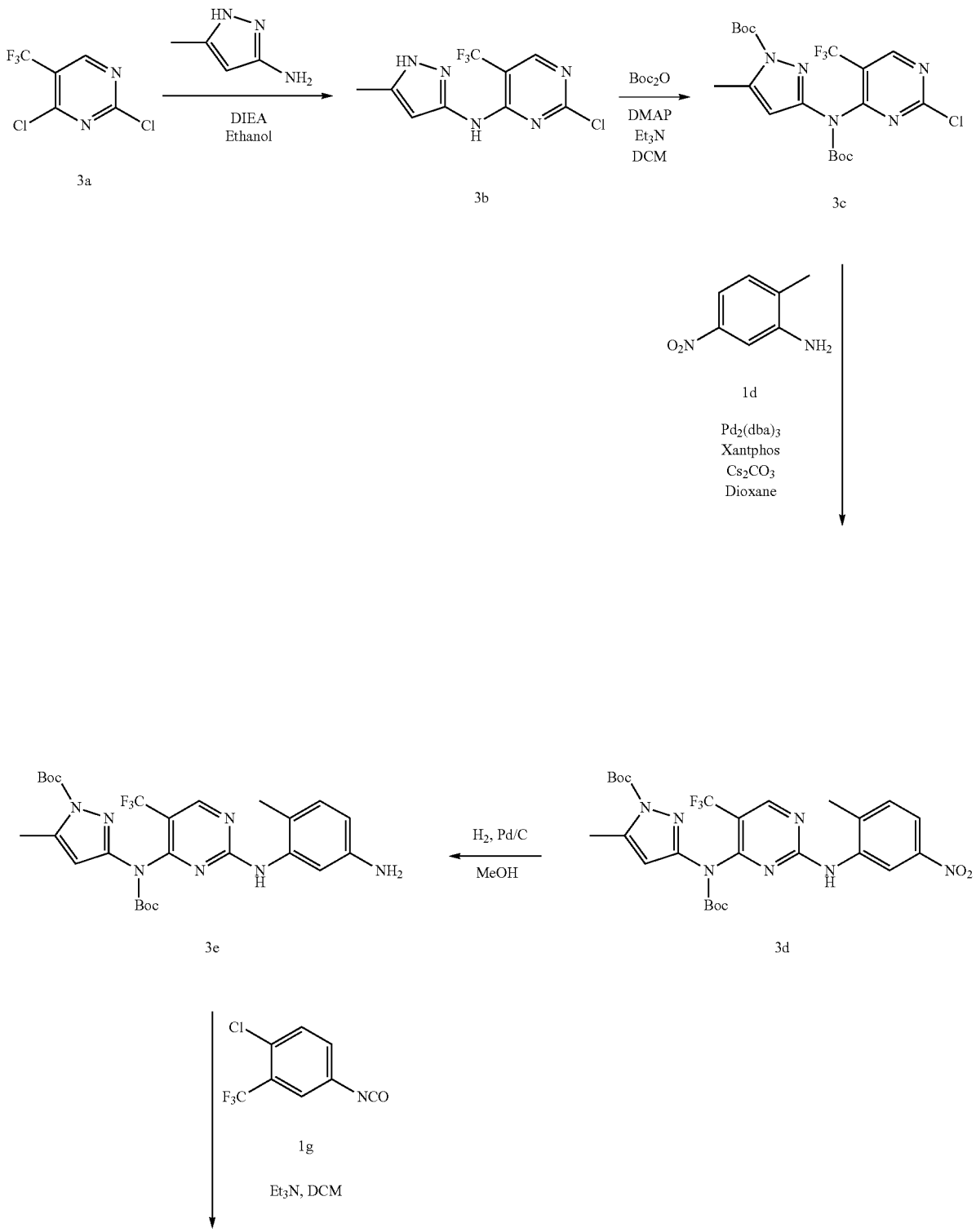

-continued

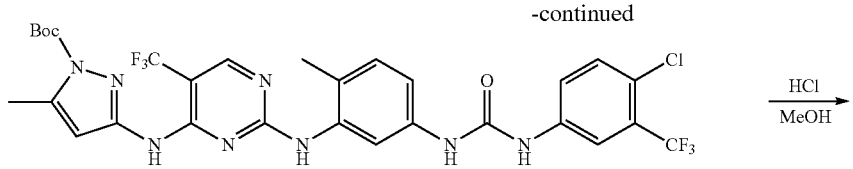

3f

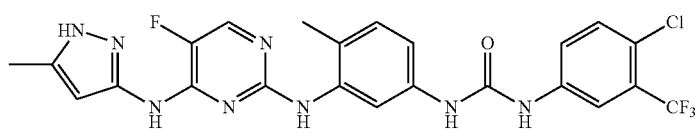

2

Step 1:

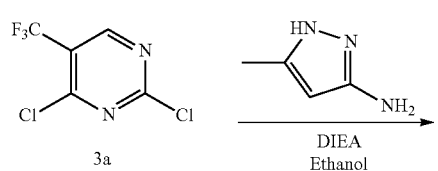

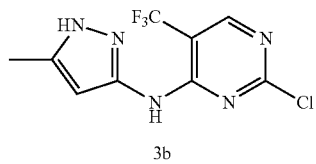

3b

Compound 3a (4.34 g, 20 mmol), 3-amino-5-methyl-pyrazole (1.94 g, 20 mmol) and diisopropylethylamine (5.17 g, 40 mmol) were added to a solution of 20 mL of ethanol and then stirred at room temperature for 6 hours. The insoluble substance was collected to obtain Compound 3b (1.7 g, Yield 31%). $^1$H NMR (400 MHz, CD$_3$OD): δ ppm 8.48 (s, 1H), 6.42 (s, 1H) 2.34 (s, 3H). MS [M+1]-278.1.

Step 2:

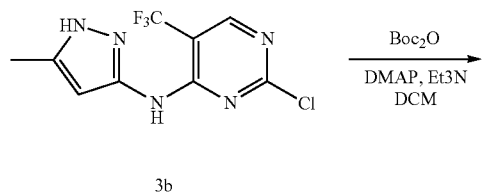

-continued

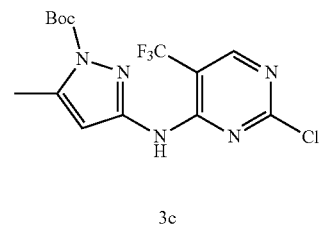

3c

Compound 3b (1.70 g, 6.1 mmol), Et$_3$N (1.55 g, 15.3 mmol), DMAP (187 mg, 1.53 mmol) were dissolved in 40 mL of dichloromethane, and then Boc$_2$O (3.3 g, 15.3 mmol) was added dropwise to the solution. The mixture was stirred overnight at room temperature. The solvent was concentrated, and the remainder was purified by silica gel column chromatography to obtain Compound 3c (650 mg, Yield 28%). $^1$H NMR (400 MHz, CDCl$_3$): δ ppm 8.48 (s, 1H), 7.79 (brs, 1H). 6.93 (s. 1H). 2.59 (s. 3H), 1.68 (s. 9H); MS [M+1]$^+$ 378.1.

Step 3:

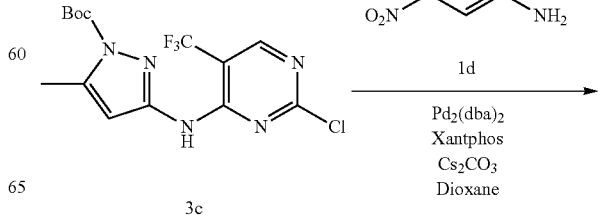

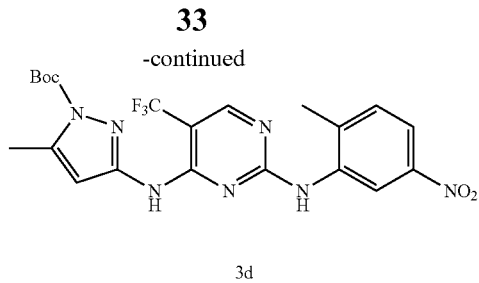

Compound 3c (650 mg, 1.72 mmol). Compound 1d (272 mg, 1.79 mmol). Pd$_2$(dba)$_3$ (158 mg, 0.17 mmol), xantphos (199 mg, 0.34 mmol) and Cs$_2$CO$_3$ (1.12 g, 3.44 mmol) and dioxane (20 mL) were added to a degassed flask and heated to reflux for 5 hours under the protection of argon. The solvent was concentrated, and the remainder was purified by silica gel column chromatography to obtain Compound 3d (130 mg, Yield 15%). $^1$H NMR (400 MHz, CDCl$_3$): δ ppm 8.68 (d, J=2.0, 1H), 8.35 (s, 1H), 8.01 (dd, J=2.4 J$_2$=2.8, 1H), 7.61 (brs, 1H), 7.43 (d, J=8.4, 1H), 7.34 (brs. 1H). 6.35 (brs, 1H). 2.43 (s, 3H). 2.34 (s, 3H). 1.65 (s, 9H): MS [M+1]$^+$ 494.2.

Step 4:

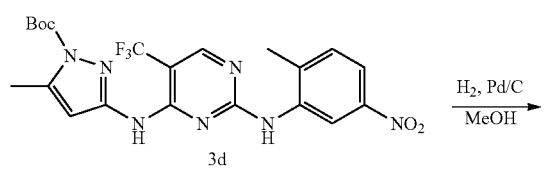

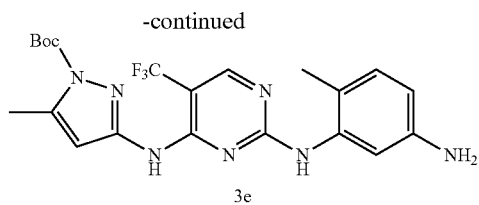

Compound 3d (130 mg, 0.26 mmol) and 13 mg of palladium/carbon were added to 15 mL of methanol and reacted overnight at room temperature under 2 atm of hydrogen atmosphere. After the formation of reactant product was determined by LC-MS, the solid was filtered out and the filtrate was concentrated to obtain crude Compound 3e, which was used directly in the next synthesis step.

Step 5:

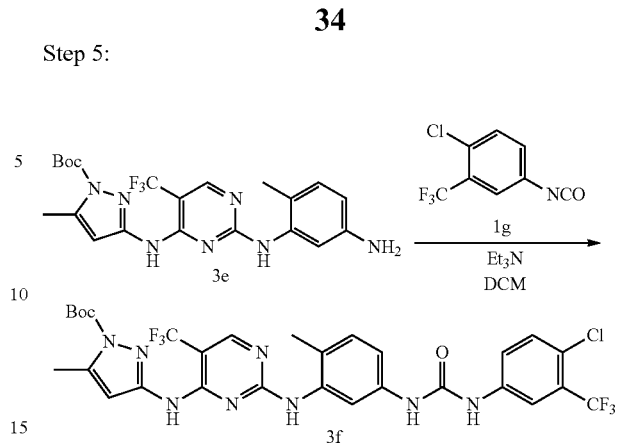

The crude product Compound 3e which obtained from the previous step, Compound 1 g (58 mg, 0.26 mmol) and triethylamine (53 mg, 0.52 mmol) were dissolved in 10 mL of anhydrous dichloromethane and then stirred at room temperature for 1 hour. The solvent was concentrated, and the remainder was purified by silica gel column chromatography to obtain Compound 3f (70 mg, the two-step yield was 39%) $^1$H NMR (400 MHz, CD$_3$OD): δ ppm 8.30 (s, 1H), 7.93 (d, J=2.4, 1H), 7.61 (dd, J=2.4, J$_2$=2.4, 1H), 7.52 (d, J=2.0, 1H), 7.48 (d, J=8.8, 1H), 7.41 (d, J=7.6, 1H). 7.26 (d, J=8.4, 1H). 6.31 (brs, 1H), 2.34 (s, 3H). 2.22 (s, 3H), 1.57 (s, 9H); MS [M+1]$^+$ 685.3.

Step 6:

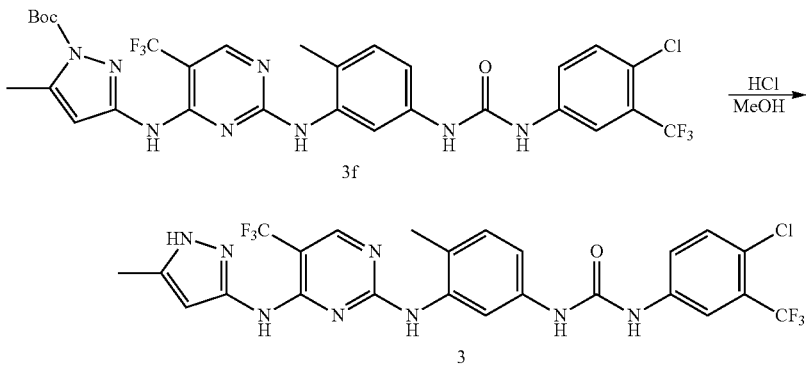

Compound 3f (70 mg, 0.10 mmol) was added to a methanol solution of 10 mL of 2 M hydrochloric acid and then stirred overnight at room temperature. The insoluble solid was collected and washed with MTBE (20 mL) to obtain hydrochloride of 1-(4-chloro-3-trifluoromethyl-phenyl)-3-{4-methyl-3-[4-(5-methyl-1H-pyrazol-3-yl-amino)-5-trifluoromethyl-pyrimidin-2-yl-amino]-phenyl}-urea (Compound 3) (14 mg, Yield 20%). $^1$H NMR (400 MHz, CD$_3$OD): δ ppm 8.30 (brs, 1H), 8.04 (s, 1H), 7.72 (s, 1H). 7.63 (d, J=8.4, 1H), 7.48 (d, J=8.4, 1H), 7.37 (m, 2H), 6.71 (brs, 1H), 2.48 (s, 3H), 2.31 (s, 3H); MS [M+l]$^+$ 585.2.

Example 4
Synthesis of 1-(4-chloro-3-trifluoromethyl-phenyl)-3-{4-methyl-3-[4-(5-methyl-1H-pyrazol-3-yl-amino)-pyrimidin-2-yl-amino]-phenyl}-urea (Compound 4)
Synthesis Route 4:
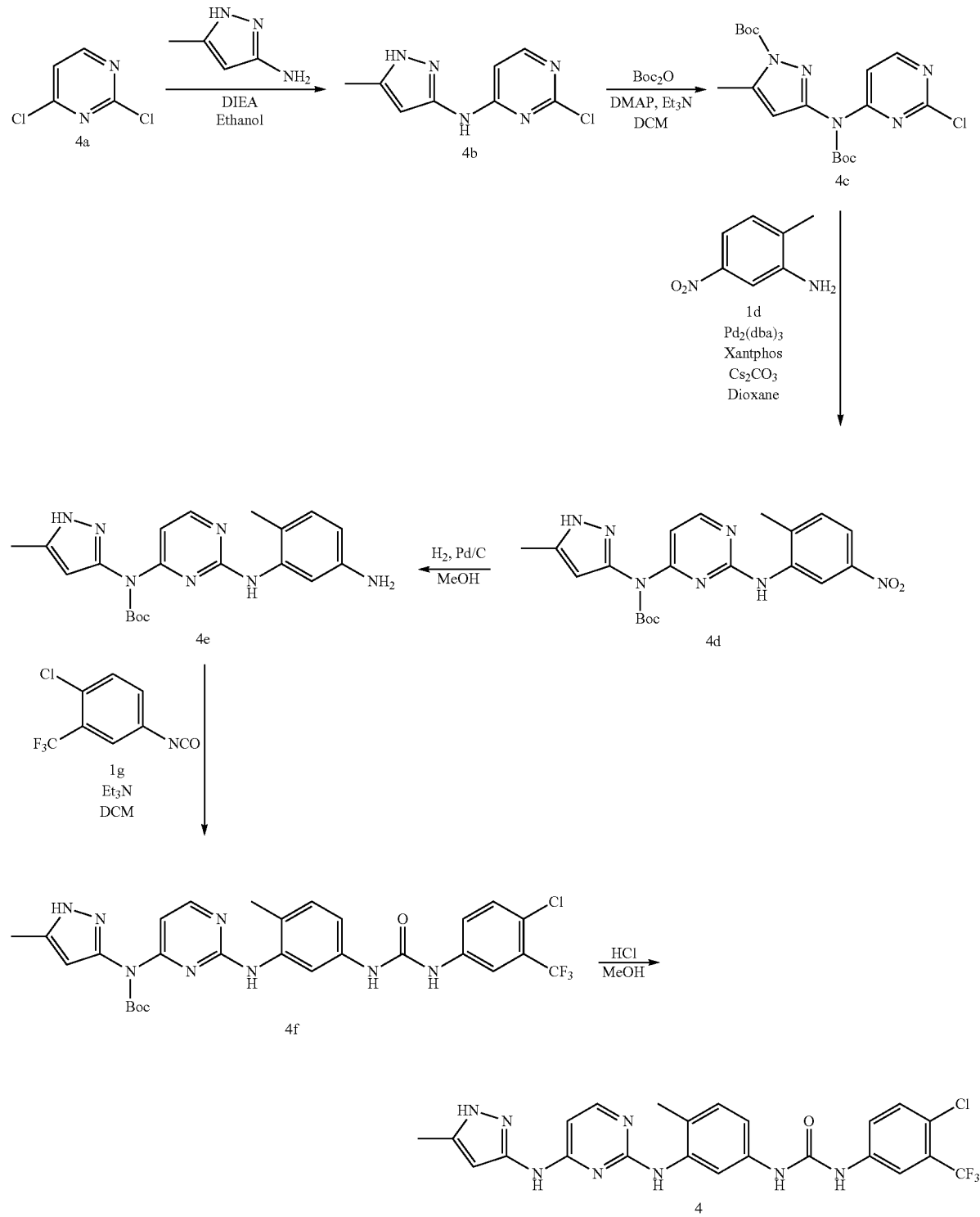

Step 1:

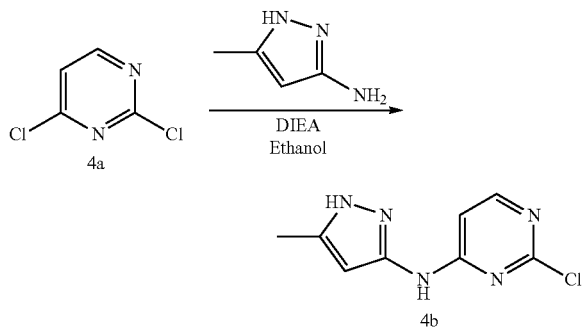

Compound 4a (3.0 g, 20 mmol), 3-amino-5-methyl-pyrazole (1.94 g, 20 mmol) and diisopropylethylamine (5.17 g, 40 mmol) were added to a ethanol solution (20 mL) and then stirred at room temperature for 2 days. The insoluble substance was collected to obtain Compound 4b (1.7 g, Yield 40%). $^1$H NMR (400 MHz, DMSO): δ ppm 12.14 (s, 1H), 10.30 (s, 1H), 8.16 (s, 1H), 6.20 (s, 1H), 2.22 (s, 3H); MS [M+1]$^+$ 210.1.

Step 2:

Compound 4b (1.70 g, 8 mmol), Et$_3$N (2.0 g, 20 mmol), DMAP (100 mg, 0.8 mmol) were dissolved in 20 mL of dichloromethane, and then Boc$_2$O (3.8 g, 18 mmol) was added dropwise to the solution. The mixture was stirred at room temperature overnight. The solvent was concentrated, and the remainder was purified by silica gel column chromatography to obtain Compound 4c (2.86 g, Yield 87%). MS [M+1]$^+$ 410.2.

Step 3:

Compound 4c (0.7 g. 1.7 mmol), Compound 1d (285 mg. 1.87 mmol), Pd$_2$(dba)$_3$ (156 mg, 0.17 mmol), xantphos (197 mg, 0.34 mmol) and Cs$_2$CO$_3$ (1.1 g, 3.4 mmol) and dioxane (15 mL) were added to a degassed flask and heated to reflux for 3 hours under the protection of argon. The solvent was concentrated, and the remainder was purified by silica gel column chromatography to obtain Compound 4d (360 mg, Yield 50%). MS [M+1]$^+$ 426.2.

Step 4:

Compound 4d (360 mg, 0.84 mmol) and 50 mg of 10% Pd/C were added to 20 mL of methanol and reacted overnight at room temperature under 2 atm of hydrogen atmosphere. After the formation of reactant product was determined by LC-MS, the solid was filtered out and the filtrate was concentrated to obtain 330 mg of crude Compound 4e. MS [M+1]$^+$ 396.3.

Step 5:

The crude product of compound 4e which obtained from the previous step (330 mg), Compound 1 g (244 mg, 1.0 mmol) and triethylamine (202 mg, 2.0 mmol) were dissolved in 10 mL of anhydrous dichloromethane and then stirred at room temperature for 2 hours. The solvent was concentrated, and the remainder was purified by silica gel column chromatography to obtain Compound 4f (50 mg, the two-step yield was 10%). MS [M+1]$^+$ 617.3.

Step 6:

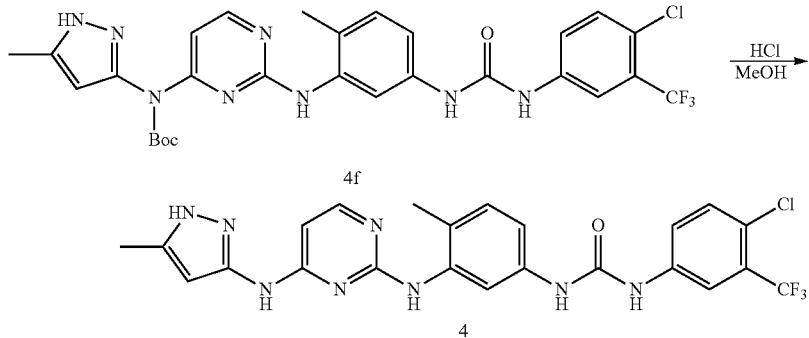

Compound 4f (50 mg, 0.08 mmol) was added to a methanol solution of 10 mL of 2 M hydrochloric acid and then stirred overnight at room temperature. The insoluble solid was collected and washed with ethyl acetate to obtain hydrochloride of 1-(4-chloro-3-trifluoromethyl-phenyl)-3-{4-methyl-3-[4-(5-methyl-1H-pyrazol-3-ylamino)-pyrimidin-2-yl-amino]-phenyl}-urea (Compound 4) (20 mg, Yield 48%). $^1$H NMR (400 MHz, CD$_3$OD): δ ppm 8.04 (s, 1H), 7.90 (s, 1H), 7.69 (s, 1H), 7.63 (d, J=7.6, 1 H). 7.48 (d. J=8.0, 1H), 7.38 (in, 2H), 6.58 (s, 1H), 6.39 (in, 1H), 2.38 (s. 3H), 2.31 (s, 3H); MS [M+1]$^+$ 517.2.

The following compounds can be prepared according to the methods for preparing Compounds 1, 2, 3, and 4.

When R$_1$=R$_2$=R$_3$=CH$_3$, K=NH, A is phenyl, and X=O, the compounds derived from varying R$_4$ are:

1-(4-chloro-3-trifluoromethyl-phenyl)-3-{3-methyl-4-[4-methyl-6-(5-methyl-2H-pyrazole-3-amino)-pyrimidine-2-amino]-phenyl}-urea
1-(4-chloro-phenyl)-3-{3-methyl-4-[4-methyl-6-(5-methyl-2H-pyrazole-3-amino)-pyrimidine-2-amino]-phenyl}-urea
1-{3-methyl-4-[4-methyl-6-(5-methyl-2H-pyrazole-3-amino)-pyrimidine-2-amino]-phenyl}-3-m-tolyl-urea
1-(3,4-dichloro-phenyl)-3-{3-methyl-4-[4-methyl-6-(5-methyl-2H-pyrazole-3-amino)-pyrimidine-2-amino]-phenyl}-urea
1-(4-isopropyl-phenyl)-3-{3-methyl-4-[4-methyl-6-(5-methyl-2H-pyrazole-3-amino)-pyrimidine-2-amino]-phenyl}-urea
Benzo-[1,3]-dioxolan-5-yl-3-{3-methyl-4-[4-methyl-6-(5-methyl-2H-pyrazole-3-amino)-pyrimidine-2-amino]-phenyl}-urea
1-{3-methyl-4-[4-methyl-6-(5-methyl-2H-pyrazole-3-amino)-pyrimidine-2-amino]-phenyl}-3-pyrid-4-yl-urea
1-(3-chloro-4-fluro-phenyl)-3-{3-methyl-4-[4-methyl-6-(5-methyl-2H-pyrazole-3-amino)-pyrimidine-2-amino]-phenyl}-urea
1-{3-methyl-4-[4-methyl-6-(5-methyl-2H-pyrazole-3-amino)-pyrimidine-2-amino]-phenyl}-3-pyrimidin-5-yl-urea
1-(3-hydroxy-phenyl)-3-{3-methyl-4-[4-methyl-6-(5-methyl-2H-pyrazole-3-amino)-pyrimidine-2-amino]-phenyl}-urea
4-(3-{3-methyl-4-[4-methyl-6-(5-methyl-2H-pyrazole-3-amino)-pyrimidine-2-amino]-phenyl}-ureido)-benzoic acid
1-(3,5-dihydroxy-phenyl)-3-{3-methyl-4-[4-methyl-6-(5-methyl-2H-pyrazole-3-amino)-pyrimidine-2-amino]-phenyl}-urea
1-{3-methyl-4-[4-methyl-6-(5-methyl-2H-pyrazole-3-amino)-pyrimidine-2-amino]-phenyl}-3-(6-oxo-1,6-dihydro-pyrid-3-yl)-urea
Cyclohexyl-3-{3-methyl-4-[4-methyl-6-(5-methyl-2H-pyrazole-3-amino)-pyrimidine-2-amino]-phenyl}-urea
Tert-butyl-3-{3-methyl-4-[4-methyl-6-(5-methyl-2H-pyrazole-3-amino)-pyrimidine-2-amino]-phenyl}-urea
1-{3-methyl-4-[4-methyl-6-(5-methyl-2H-pyrazole-3-amino)-pyrimidine-2-amino]-phenyl}-3-(tetrahydropyran-4-yl)-urea
{3-methyl-4-[4-methyl-6-(5-methyl-2H-pyrazole-3-amino)-pyrimidine-2-amino]-phenyl}-urea
1-(3H-imidazol-4-yl)-3-{3-methyl-4-[4-methyl-6-(5-methyl-2H-pyrazole-3-amino)-pyrimidine-2-amino]-phenyl}-urea
1-{3-methyl-4-[4-methyl-6-(5-methyl-2H-pyrazole-3-amino)-pyrimidine-2-amino]-phenyl}-3-thiazol-5-yl-urea
1-{3-methyl-4-[4-methyl-6-(5-methyl-2H-pyrazole-3-amino)-pyrimidine-2-amino]-phenyl}-3-{3-nitro-phenyl}-urea
1-{3-methyl-4-[4-methyl-6-(5-methyl-2H-pyrazole-3-amino)-pyrimidine-2-amino]-phenyl}-3-quinolin-8-yl-urea
Methyl-3-{3-methyl-4-[4-methyl-6-(5-methyl-2H-pyrazole-3-amino)-pyrimidine-2-amino]-phenyl}-urea
1-{3-methyl-4-[4-methyl-6-(5-methyl-2H-pyrazole-3-amino)-pyrimidine-2-amino]-phenyl}-3-{3-methyl-thiophenyl}-urea
1-{3-methyl-4-[4-methyl-6-(5-methyl-2H-pyrazole-3-amino)-pyrimidine-2-amino]-phenyl}-3-piperid-4-yl-urea
1-{3-methyl-4-[4-methyl-6-(5-methyl-2H-pyrazole-3-amino)-pyrimidine-2-amino]-phenyl}-3-(1-methyl-piperid-4-yl)-urea
1-(1-acetyl-piperid-4-yl)-3-{3-methyl-4-[4-methyl-6-(5-methyl-2H-pyrazole-3-amino)-pyrimidine-2-amino]-phenyl}-urea
Butyl-3-{3-methyl-4-[4-methyl-6-(5-methyl-2H-pyrazole-3-amino)-pyrimidine-2-amino]-phenyl}-urea
1-(1H-benzoimidazol-5-yl)-3-{3-methyl-4-[4-methyl-6-(5-methyl-2H-pyrazole-3-amino)-pyrimidine-2-amino]-phenyl}-urea
2-benzyl-3-(3-{3-methyl-4-[4-methyl-6-(5-methyl-2H-pyrazole-3-amino)-pyrimidine-2-amino]-phenyl}-ureido)-3-oxo-propionic acid
1-{3-methyl-4-[4-methyl-6-(5-methyl-2H-pyrazole-3-amino)-pyrimidine-2-amino]-phenyl}-3-thien-2-yl-urea
1-furan-2-yl-3-{3-methyl-4-[4-methyl-6-(5-methyl-2H-pyrazole-3-amino)-pyrimidine-2-amino]-phenyl}-urea 1-{3-methyl-4-[4-methyl-6-(5-methyl-2H-pyrazole-3-amino)-pyrimidine-2-amino]-phenyl}-3-(1-methyl-1H-pyrrol-2-yl)-urea Benzofuran-2-yl-3-{3-methyl-4-[4-methyl-6-(5-methyl-2H-pyrazole-3-amino)-pyrimidine-2-amino]-phenyl}-urea 1-benzo[b]thien-2-yl-3-{3-methyl-4-[4-methyl-4-(5-methyl-2H-pyrazole-3-amino)-pyrimidine-2-amino]-phenyl}-urea 1-cyclopentyl-3-{3-methyl-4-[4-methyl-6-(5-methyl-2H-pyrazole-3-amino)-pyrimidine-2-amino]-phenyl}-urea 1-cyclobutyl-3-{3-methyl-4-[4-methyl-6-(5-methyl-2H-pyrazole-3-amino)-pyrimidine-2-amino]-phenyl}-urea When $R_2=R_3=CH_3$, $R_4$=4-chloro-3-trifluoromethyl-phenyl, $K=NH$, $X=O$, and A is phenyl, the compounds derived from varying $R_1$ are:

1-(4-chloro-3-trifluoromethyl-phenyl)-3-{4-[4-(5-isopropyl-2H-pyrazole-3-amino)-6-methyl-pyrimidine-2-amino]-3-methyl-phenyl}-urea 1-{4-[4-(5-chloro-2H-pyrazole-3-amino)-6-methyl-pyrimidine-2-amino]-3-methyl-phenyl}-3-(4-chloro-3-trifluoromethyl-phenyl)-urea 1-(4-chloro-3-trifluoromethyl-phenyl)-3-{4-[4-(5-ethyl-2H-pyrazole-3-amino)-6-methyl-pyrimidine-2-amino]-3-methyl-phenyl}-urea 5-(2-{4-[3-(4-chloro-3-trifluoromethyl-phenyl)-ureido]-2-methyl-phenyl-amino}-6-methyl-pyrimidine-4-amino)-1H-pyrazole-3-formic acid 1-(4-chloro-3-trifluoromethyl-phenyl)-3-{5-methyl-6-[4-methyl-6-(5-oxo-2H-pyrazole-3-amino)-pyrimidine-2-amino]-pyrid-3-yl}-urea 1-{4-[4-(5-acetyl-2H-pyrazole-3-amino)-6-methyl-pyrimidine-2-amino]-3-methyl-phenyl}-3-(4-chloro-3-trifluoromethyl-phenyl)-urea 5-(2-{4-[3-(4-chloro-3-trifluoromethyl-phenyl)-ureido]-2-methyl-phenyl-amino}-6-methyl-pyrimidine-4-amino)-1H-pyrazole-3-formamide 1-(4-chloro-3-trifluoromethyl-phenyl)-3-{3-methyl-4-[4-methyl-6-(5-nitro-2H-pyrazole-3-amino)-pyrimidine-2-amino]-phenyl}-urea 1-(4-chloro-3-trifluoromethyl-phenyl)-3-{3-methyl-4-[4-methyl-6-(5-phenyl-2H-pyrazole-3-amino)-pyrimidine-2-amino]-phenyl}-urea 1-(4-chloro-3-trifluoromethyl-phenyl)-3-{3-methyl-4-[4-methyl-6-(5-methyl-thio-2H-pyrazole-3-amino)-pyrimidine-2-amino]-phenyl}-urea 1-(4-chloro-3-trifluoromethyl-phenyl)-3-{4-[4-(5-methoxy-2H-pyrazole-3-amino)-6-methyl-pyrimidine-2-amino]-3-methyl-phenyl}-urea 1-{4-[4-(5-bromo-2H-pyrazole-3-amino)-6-methyl-pyrimidine-2-amino]-3-methyl-phenyl}-3-(4-chloro-3-trifluoromethyl-phenyl)-urea 1-{4-[4-(5-amino-2H-pyrazole-3-amino)-6-methyl-pyrimidine-2-amino]-3-methyl-phenyl}-3-(4-chloro-3-trifluoromethyl-phenyl)-urea 1-(4-chloro-3-trifluoromethyl-phenyl)-3-{4-[4-(5-furan-2-yl-2H-pyrazole-3-amino)-6-methyl-pyrimidine-2-amino]-3-methyl-phenyl}-urea 1-{4-[4-(5-tertbutyl-2H-pyrazole-3-amino)-6-methyl-pyrimidine-2-amino]-3-methyl-phenyl}-3-(4-chloro-3-trifluoromethyl-phenyl)-urea 1-(4-chloro-3-trifluoromethyl-phenyl)-3-{4-[4-(5-cyclopropyl-2H-pyrazole-3-amino)-6-methyl-pyrimidine-2-amino]-3-methy-phenyl}-urea 1-(4-chloro-3-trifluoromethyl-phenyl)-3-{4-[4-(5-cyclobutyl-2H-pyrazole-3-amino)-6-methyl-pyrimidine-2-amino]-3-methyl-phenyl}-urea 1-(4-chloro-3-trifluoromethyl-phenyl)-3-{3-methyl-4-[4-methyl-6-(5-thien-2-yl-2H-pyrazole-3-amino)-pyrimidine-2-amino]-phenyl}-urea 1-(4-chloro-3-trifluoromethyl-phenyl)-3-{3-methyl-4-{4-methyl-6-[5-(1H-pyrrol-2-yl)-2H-pyrazole-3-amino]-pyrimidine-2-amino}-phenyl}-urea 1-(4-chloro-3-trifluoromethyl-phenyl)-3-{4-[4-(5-cyano-2H-pyrazole-3-amino)-6-methyl-pyrimidine-2-amino]-3-methyl-phenyl}-urea 5-(2-{4-[3-(4-Chloro-3-trifluoromethyl-phenyl)-ureido]-2-methyl-phenylamino}-6-methyl-pyrimidin-4-ylamino)-1H-pyrazole-3-carboximidic acid methyl ester 1-(4-chloro-3-trifluoromethyl-phenyl)-3-{3-methyl-4-[4-methyl-6-(2H-pyrazole-3-amino)-pyrimidine-2-amino]-phenyl}-urea 1-(4-chloro-3-trifluoromethyl-phenyl)-3-{4-[4-(5-fluoro-2H-pyrazole-3-amino)-6-methyl-pyrimidine-2-amino]-3-methyl-phenyl}-urea 1-(4-chloro-3-trifluoromethyl-phenyl)-3-{4-[4-(5-ethoxy-2H-pyrazole-3-amino)-6-methyl-pyrimidine-2-amino]-3-methyl-phenyl}-urea 1-(4-chloro-3-trifluoromethyl-phenyl)-3-{4-[4-(5-hydroxy-2H-pyrazole-3-amino)-6-methyl-pyrimidine-2-amino]-3-methyl-phenyl}-urea 5-(2-{4-[3-(4-chloro-3-trifluoromethyl-phenyl)-ureido]-2-methyl-phenyl-amino}-6-methyl-pyrimidine-4-amino)-1H-pyrazol-3-yl acetate Ethyl 5-(2-(4-[3-(4-chloro-3-trifluoromethyl-phenyl)-ureido]-2-methyl-phenyl-amino)-6-methyl-pyrimidine-4-amino)-1H-pyrazole-3-formate N-[5-(2-{4-[3-(4-chloro-3-trifluoromethyl-phenyl)-ureido]-2-methyl-phenyl-amino}-6-methyl-pyrimidine-4-amino)-1H-pyrazol-3-yl]-acetamide 5-(2-{4-[3-(4-chloro-3-trifluoromethyl-phenyl)-ureido]-2-methyl-phenyl-amino)-6-methyl-pyrimidine-4-amino}-1H-pyrazole-3-formamidine 1-(4-chloro-3-trifluoromethyl-phenyl)-3-(4-{4-[5-(1-hydroxy-ethyl)-2H-pyrazole-3-amino]-6-methyl-pyrimidine-2-amino)-3-methyl-phenyl)-urea 1-(4-chloro-3-trifluoromethyl-phenyl)-3-{3-methyl-4-[4-methyl-6-(5-morpholin-4-yl-2H-pyrazole-3-amino)-pyrimidine-2-amino]-phenyl}-urea 1-(4-chloro-3-trifluoromethyl-phenyl)-3-{4-[4-(5-dimethylamino-2H-pyrazole-3-amino)-6-methyl-pyrimidine-2-amino]-3-methyl-phenyl}-urea 1-(4-chloro-3-trifluoromethyl-phenyl)-3-{4-[4-(5-ethynyl-2H-pyrazole-3-amino)-6-methyl-pyrimidine-2-amino]-3-methyl-phenyl}-urea 1-(4-chloro-3-trifluoromethyl-phenyl)-3-{3-methyl-4-[4-methyl-6-(5-vinyl-2H-pyrazole-3-amino)-pyrimidine-2-amino]-phenyl}-urea 1-(4-chloro-3-trifluoromethyl-phenyl)-3-{3-methyl-4-[4-methyl-6-(5-piperazin-1-yl-2H-pyrazole-3-amino)-pyrimidine-2-amino]-phenyl}-urea 1-(4-chloro-3-trifluoromethyl-phenyl)-3-{3-methyl-4-[4-methyl-6-(5'-methyl-1H,2'H-[3,3']-dipyrazolyl-5-amino)-pyrimidine-2-amino]-phenyl}-urea When $R_2=H$, $R_3=H$, $R_4$=4-chloro-3-trifluoromethyl-phenyl, $K=NH$, $X=O$, and A is pyridyl, the compounds derived from varying $R_1$ are:

1-(4-chloro-3-trifluoromethyl-phenyl)-3-{5-[4-(5-isopropyl-2H-pyrazole-3-amino)-6-methyl-pyrimidine-2-amino]-pyrid-2-yl}-urea 1-{5-[4-(5-chloro-2H-pyrazole-3-amino)-6-methyl-pyrimidine-2-amino]-pyrid-2-yl-3-(4-chloro-3-trifluoromethyl-phenyl}-urea 1-(4-chloro-3-trifluoromethyl-phenyl)-3-{5-[4-(5-ethyl-2H-pyrazole-3-amino)-6-methyl-pyrimidine-2-amino]-pyrid-2-yl}-urea 5-(2-{6-[3-(4-chloro-3-trifluoromethyl-phenyl)-ureido]-pyridine-3-amino}-6-methyl-pyrimidine-4-amino)-1H-pyrazole-3-formic acid 1-(4-chloro-3-trifluoromethyl-phenyl)-3-{5-[4-methyl-6-(5-oxo-5H-pyrazole-3-amino)-pyrimidine-2-amino]-pyrid-2-yl}-urea 1-{5-[4-(5-acetyl-2H-pyrazole-3-amino)-6-methyl-pyrimidine-2-amino]-pyrid-2-yl}-3-(4-chloro-3-trifluoromethyl-phenyl)-urea 5-(2-{6-[3-(4-chloro-3-trifluoromethyl-phenyl)-ureido]-pyridine-3-amino}-6-methyl-pyrimidine-4-amino)-1H-pyrazole-3-formamide 1-(4-chlor-trifluoromethyl-phenyl)-3-{5-[4-methyl-6-(5-nitro-2H-pyrazole-3-amino)-pyrimidine-2-amino]-pyrid-2-yl}-urea 1-(4-chloro-3-trifluoromethyl-phenyl)-3-{5-[4-methyl-6-(5-phenyl-2H-pyrazole 3-amino)-pyrimidine-2-amino]-pyrid-2-yl}-urea 1-(4-chloro-3-trifluoromethyl-phenyl)-3-{5-[4-methyl-6-(5-methyl-thio-2H-pyrazole-3-amino)-pyrimidine-2-amino]-pyrid-2-yl}-urea 1-(4-chloro-3-trifluoromethyl-phenyl)-3-{5-[4-(5-methoxy-2H-pyrazole-3-amino)-6-methyl-pyrimidine-2-amino]-pyrid-2-yl}-urea 1-{5-[4-(5-bromo-2H-pyrazole-3-amino)-6-methyl-pyrimidine-2-amino]-pyrid-2-yl-3-(4-chloro-3-trifluoromethyl-phenyl}-urea 1-{5-[4-(5-amino-2H-pyrazole-3-amino)-6-methyl-pyrimidine-2-amino]-pyrid-2-yl-3-(4-chloro-3-trifluoromethyl-phenyl}-urea 1-(4-chloro-3-trifluoromethyl-phenyl)-3-{5-[4-(5-furan-2-yl-2H-pyrazole-3-amino)-6-methyl-pyrimidine-2-amino]-pyrid-2-yl}-urea 1-{5-[4-(5-tertbutyl-2H-pyrazole-3-amino)-6-methyl-pyrimidine-2-amino]-pyrid-2-yl}-3-(4-chloro-3-trifluoromethyl-phenyl)-urea 1-(4-chloro-3-trifluoromethyl-phenyl)-3-{5-[4-(5-ethyl-2H-pyrazole-3-amino)-6-methyl-pyrimidine-2-amino]-pyrid-2-yl}-urea 1-(4-chloro-3-trifluoromethyl-phenyl)-3-{5-[4-(5-cyclobutyl-2H-pyrazole-3-amino)-6-methyl-pyrimidine-2-amino]-pyrid-2-yl}-urea 1-(4-chloro-3-trifluoromethyl-phenyl)-3-{5-[4-methyl-6-(5-thien-2-yl-2H-pyrazole-3-amino)-pyrimidine-2-amino]-pyrid-2-yl}urea 1-(4-chlor-3-trifluoromethyl-phenyl)-3-(5-{4-methyl-6-[5-(1H-pyrrol-2-yl)-2H-pyrazole-3-amino]-pyrimidine-2-amino]-pyrid-2-yl)-urea 1-(4-chloro-3-trifluoromethyl-phenyl)-3-{5-[4-(5-cyano-2H-pyrazole-3-amino)-6-methyl-pyrimidine-2-amino]-pyrid-2-yl}-urea 5-(2-{6-[3-(4-chloro-3-trifluoromethyl-phenyl)-ureido]-pyridine-3-amino}-6-methyl-pyrimidine-4-amino)-1H-pyrazole-3-carboximidic acid methyl ester 1-(4-chloro-3-trifluoromethyl-phenyl)-3-{4-methyl-5-[4-methyl-6-(2H-pyrazole-3-amino)-pyrimidine-2-amino]-pyrid-2-yl}-urea 1-(4-chloro-3-trifluoromethyl-phenyl)-3-{5-[4-(5-fluoro-2H-pyrazole-3-amino)-6-methyl-pyrimidine-2-amino]-pyrid-2-yl}-urea 1-(4-chloro-3-trifluoromethyl-phenyl)-3-{5-[4-(5-ethoxy-2H-pyrazole-3-amino)-6-methyl-pyrimidine-2-amino]-pyrid-2-yl}-urea 1-(4-chloro-3-trifluoromethyl-phenyl)-3-{5-[4-(5-hydroxy-2H-pyrazole-3-amino)-6-methyl-pyrimidine-2-amino]-pyrid-2-yl}-urea 5-(2-{6-[3-(4-chloro-3-trifluoromethyl-phenyl)-ureido]-pyridine-3-amino}-6-methyl-pyrimidine-4-amino)-1H-pyrazol-3-yl acetate Ethyl 5-(2-{6-[3-(4-chloro-3-trifluoromethyl-phenyl)-ureido]-pyridine-3-amino}-6-methyl-pyrimidine-4-amino)-1H-pyrazole-3-formate N-[5-(2-{6-[3-(4-chloro-3-trifluoromethyl-phenyl)-ureido]-pyridine-3-amino}-6-methyl-pyrimidine-4-amino)-1H-pyrazol-3-yl]-acetamide 5-(2-{6-[3-(4-chloro-3-trifluoromethyl-phenyl)-ureido]-pyridine-3-amino}-6-methyl-pyrimidine-4-amino)-1H-pyrazole-3-formamidine 1-(4-chlor-trifluoromethyl-phenyl)-3-(5-{4-(5-(1-hydroxy-ethyl)-2H-pyrazole-3-amino-6-methyl-pyrimidine-2-amino}-pyrid-2-yl)-urea 1-(4-chlor-trifluoromethyl-phenyl)-3-{5-[4-methyl-6-(5-morpholin-4-yl-2H-pyrazole-3-amino)-pyrimidine-2-amino]-pyrid-2-yl}-urea 1-(4-chloro-3-trifluoromethyl-phenyl)-3-{5-[4-(5-dimethylamino-2H-pyrazole-3-amino)-6-methyl-pyrimidine-2-amino]-pyrid-2-yl}-urea 1-(4-chloro-3-trifluoromethyl-phenyl)-3-{5-[4-(5-ethynyl-2H-pyrazole-3-amino)-6-methyl-pyrimidine-2-amino]-pyrid-2-yl}-urea 1-(4-chloro-3-trifluoromethyl-phenyl)-3-{5-[4-methyl-6-(5-vinyl-2H-pyrazole-3-amino)-pyrimidine-2-amino]-pyrid-2-yl}-urea 1-(4-chlor-trifluoromethyl-phenyl)-3-{5-[4-methyl-6-(5-piperazin-1-yl-2H-pyrazole-3-amino)-pyrimidine-2-amino]-pyrid-2-yl}-urea 1-(4-chloro-3-trifluoromethyl-phenyl)-3-{5-[4-methyl-6-(5'-methyl-1H,2'H-[3,3']-dipyrazolyl-5-amino)-pyrimidine-2-amino]-pyrid-2-yl}-urea When $R_2$=H, $R_3$=H, $R_{4=4}$-chloro-3-trifluoromethyl-phenyl, K=NH, X=S, and A is pyridyl, the compounds derived from varying $R_1$ are:

1-(4-chloro-3-trifluoromethyl-phenyl)-3-{5-[4-(5-isopropyl-2H-pyrazole-3-amino)-6-methyl-pyrimidine-2-amino]-pyrid-2-yl}-thiourea 1-{5-[4-(5-chloro-2H-pyrazole-3-amino)-6-methyl-pyrimidine-2-amino]-pyrid-2-yl}-3-(4-chloro-3-trifluoromethyl-phenyl)-thiourea 1-(4-chloro-3-trifluoromethyl-phenyl)-3-{5-[4-(5-ethyl-2H-pyrazole-3-amino)-6-methyl-pyrimidine-2-amino]-pyrid-2-yl}-thiourea 5-(2-{6-[3-(4-chloro-3-trifluoromethyl-phenyl)-thioureido]-pyridine-3-amino}-1-methyl-pyrimidine-4-amino)-1H-pyrazole-3-formic acid 1-(4-chloro-3-trifluoromethyl-phenyl)-3-{5-[4-methyl-6-(5-oxo-5H-pyrazole-3-amino)-pyrimidine-2-amino]-pyrid-2-yl}-thiourea 1-{5-[4-(5-acetyl-2H-pyrazole-3-amino)-6-methyl-pyrimidine-2-amino]-pyrid-2-yl}-3-(4-chloro-3-trifluoromethyl-phenyl)-thiourea 5-(2-{6-[3-(4-chloro-3-trifluoromethyl-phenyl)-thioureido]-pyridine-3-amino}-6-methyl-pyrimidine-4-amino)-1H-pyrazole-3-formamide 1-(4-chlor-trifluoromethyl-phenyl)-3-{5-[4-methyl-6-(5-nitro-2H-pyrazole-3-amino)-pyrimidine-2-amino]-pyrid-2-yl}-thiourea 1-(4-chloro-3-trifluoromethyl-phenyl)-3-{5-[4-methyl-6-(5-phenyl-2H-pyrazole-3-amino)-pyrimidine-2-amino]-pyrid-2-yl}-thiourea 1-(4-chloro-3-trifluoromethyl-phenyl)-3-{5-[4-methyl-6-(5-methylthio-2H-pyrazole-3-amino)-pyrimidine-2-amino]-pyrid-2-yl}-thiourea 1-(4-chloro-3-trifluoromethyl-phenyl)-3-{5-[4-(5-methoxy-2H-pyrazole-3-amino)-6-methyl-pyrimidine-2-amino]-pyrid-2-yl}-thiourea 1-{5-[4-(5-bromo-2H-pyrazole-3-amino)-6-methyl-pyrimidine-2-amino]-pyrid-2-yl}-3-(4-chloro-3-trifluoromethyl-phenyl)-thiourea 1-{5-[4-(5-amino-2H-pyrazole-3-amino)-6-methyl-pyrimidine-2-amino]-pyrid-2-yl}-3-(4-chloro-3-trifluoromethyl-phenyl)-thiourea 1-(4-chloro-3-trifluoromethyl-phenyl)-3-{5-[4-(5-furan-2-yl-2H-pyrazole-3-amino)-6-methyl-pyrimidine-2-amino]-pyrid-2-yl}-thiourea 1-{5-[4-(5-tertbutyl-2H-pyrazole-3-amino)-6-methyl-pyrimidine-2-amino]-pyrid-2-yl}-3-(4-chloro-3-trifluoromethyl-phenyl)-thiourea 1-(4-chloro-3-trifluoromethyl-phenyl)-3-{5-[4-(5-cyclopropyl-2H-pyrazole-3-amino)-6-methyl-pyrimidine-2-amino]-pyrid-2-yl}-thiourea 1-(4-chloro-3-trifluoromethyl-phenyl)-3-{5-[4-(5-cyclobutyl-2H-pyrazole-3-amino)-6-methyl-pyrimidine-2-amino]-pyrid-2-yl}-thiourea 1-(4-chloro-3-trifluoromethyl-phenyl)-3-{5-[4-methyl-6-(5-thien-2-yl-2H-pyrazole-3-amino)-pyrimidine-2-amino]-pyrid-2-yl}-thiourea 1-(4-chlor-3-trifluoromethyl-phenyl)-3-(5-{4-methyl-6-[5-(1H-pyrrol-2-yl)-2H-pyrazole-3-amino]-pyrimidine-2-amino}-pyrid-2-yl)-thiourea (4-chloro-3-trifluoromethyl-phenyl)-3-{5-[4-(5-cyano-2H-pyrazole-3-amino)-6-methyl-pyrimidine-2-amino]-pyrid-2-yl}-thiourea 5-(2-{6-[3-(4-chloro-3-trifluoromethyl-phenyl)-thioureido]-pyridine-3-amino}-6-methyl-pyrimidine-4-amino)-1H-pyrazole-3-carboximidic acid methyl ester 1-(4-chloro-3-trifluoromethyl-phenyl)-3-{4-methyl-5-[4-methyl-6-(2H-pyrazole-3-amino)-pyrimidine-2-amino]-pyrid-2-yl}-thiourea 1-(4-chloro-3-trifluoromethyl-phenyl)-3-{5-[4-(5-fluoro-2H-pyrazole-3-amino)-6-methyl-pyrimidine-2-amino]-pyrid-2-yl}-thiourea 1-(4-chloro-3-trifluoromethyl-phenyl)-3-{5-[4-(5-ethoxy-2H-pyrazole-3-amino)-6-methyl-pyrimidine-2-amino]-pyrid-2-yl}-thiourea 1-(4-chloro-3-trifluoromethyl-phenyl)-3-{5-[4-(5-hydroxy-2H-pyrazole-3-amino)-6-methyl-pyrimidine-2-amino]-pyrid-2-yl}-thiourea 5-(2-{6-[3-(4-chloro-3-trifluoromethyl-phenyl)-thioureido]-pyridine-3-amino}-6-methyl-pyrimidine-4-amino)-1H-pyrazol-3-yl acetate Ethyl 5-(2-{6-[3-(4-chloro-3-trifluoromethyl-phenyl)-thioureido]-pyridine-3-amino}-6-methyl-pyrimidine-4-amino)-1H-pyrazole-3-formate N-[5-(2-{6-[3-(4-chloro-3-trifluoromethyl-phenyl)-thioureido]-pyridine-3-amino}-6-methyl-pyrimidine-4-amino)-1H-pyrazol-3-yl]-acetamide 5-(2-{6-[3-(4-chloro-3-trifluoromethyl-phenyl)-thioureido]-pyridine-3-amino}-6-methyl-pyrimidine-4-amino)-1H-pyrrol-3-formamidine 1-(4-chloro-3-trifluoromethyl-phenyl)-3-(5-{4-[5-(1-hydroxy-ethyl)-2H-pyrazole-3-amino]-6-methyl-pyrimidine-2-amino}-pyrid-2-yl)-thiourea 1-(4-chloro-3-trifluoromethyl-phenyl)-3-{5-[4-methyl-6-(5-morpholin-4-yl-2H-pyrazole-3-amino)-pyrimidine-2-amino]-pyrid-2-yl}-thiourea 1-(4-chloro-3-trifluoromethyl-phenyl)-3-{5-[4-(5-dimethylamino-2H-pyrazole-3-amino)-6-methyl-pyrimidine-2-amino]-pyrid-2-yl}-thiourea 1-(4-chloro-3-trifluoromethyl-phenyl)-3-{5-[4-(5-ethynyl-2H-pyrazole-3-amino)-6-methyl-pyrimidine-2-amino]-pyrid-2-yl}-thiourea 1-(4-chloro-3-trifluoromethyl-phenyl)-3-{5-[4-methyl-6-(5-vinyl-2H-pyrazole-3-amino)-pyrimidine-2-amino]-pyrid-2-yl}-thiourea 1-(4-chloro-3-trifluoromethyl-phenyl)-3-{5-[4-methyl-6-(5-piperazin-1-yl-2H-pyrazole-3-amino)-pyrimidine-2-amino]-pyrid-2-yl}-thiourea 1-(4-chloro-3-trifluoromethyl-phenyl)-3-{5-[4-methyl-6-(5'-methyl-1H,2'H-[3,3']-dipyrazolyl-5-amino)-pyrimidine-2-amino]-pyrid-2-yl}-thiourea Example 5

Synthesis of 1-(4-chloro-3-trifluoromethyl-phenyl)-3-{3-[5-fluoro-4-(5-methyl-1H-pyrazol-3-yl-amino)-pyrimidin-2-yl]-4-methyl-phenyl}-urea (Compound 5)

Synthesis Route 5:

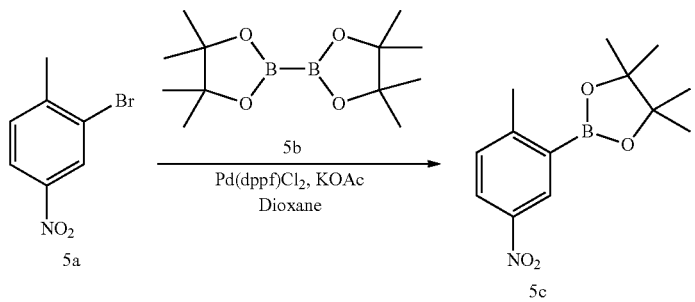

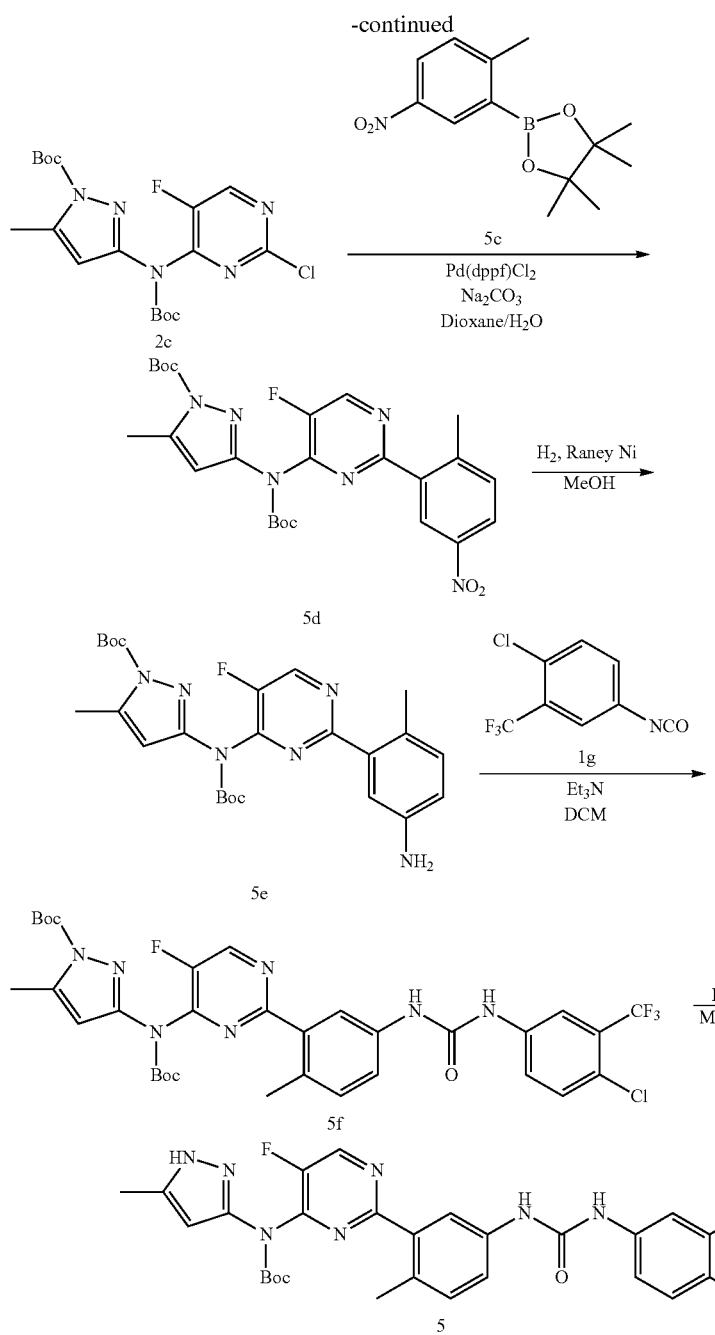
Step 1:
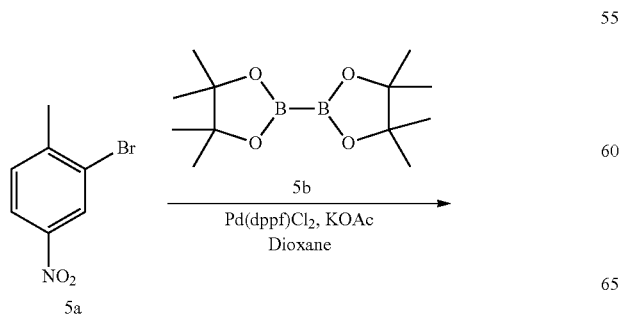
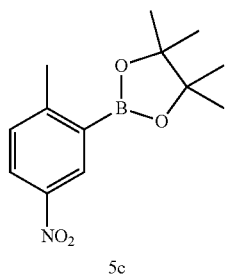

After replacing the air, Compound 5a (1.05 g, 5 mmol), Compound 5b (1.5 g, 6 mmol), Pd(dppf)Cl$_2$ (365 mg, 0.5 mmol) and KOAc (980 mg. 10 mmol) were added to a solution of 20 mL of 1,4-dioxane under the protection of nitrogen and heated to reflux by stirring overnight. The mixture was cooled to room temperature. The filtrate was concentrated and purified by silica gel column chromatography to obtain 1.2 g of Compound 5c with a yield of 93%. $^1$H NMR (400 MHz. CDCl$_3$): δ ppm 8.62 (d, J=2.4, 1 H), 8.15 (dd, J$_1$=2.4, J$_2$=2.8, 1H), 7.31 (d, J=8.0, 1H), 2.65 (s, 3H), 1.38 (s. 12H).

Step 2:

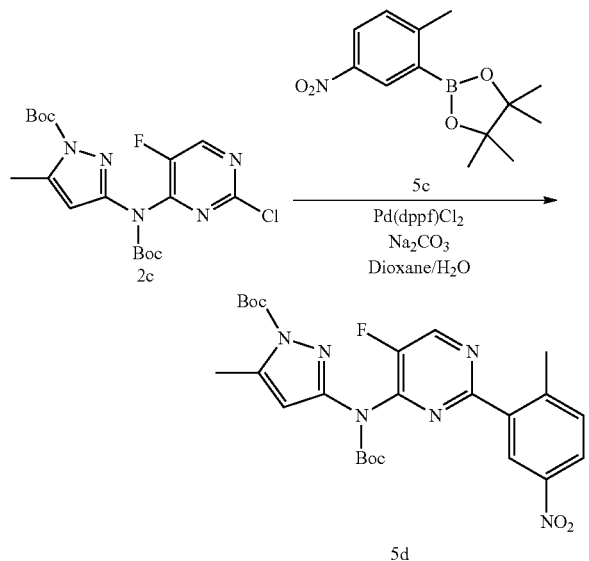

Compound 2c (540 mg, 1.26 mmol), Compound 5c (400 mg, 1.5 mmol), Pd(dppf)Cl$_2$ (95 mg, 0.13 mmol), Na$_2$CO$_3$ (270 mg 2.5 mmol), dioxane (20 mL) and water (1 mL) were added to a degassed flask and heated to reflux for 3 hours under the protection of argon. The solvent was concentrated, and the remainder was purified by silica gel column chromatography to obtain Compound 5d (510 mg, Yield 77%0/). MS [M+1]$^+$ 529.3.

Step 3:

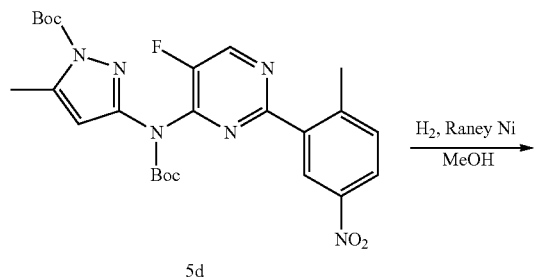

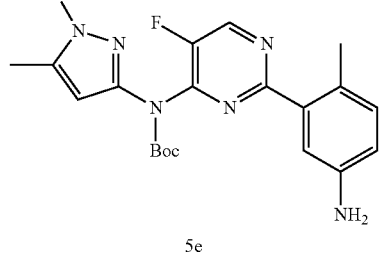

Compound 5d (510 mg, 0.96 mmol) and 400 mg of Raney nickel were added to 50 mL of methanol and reacted overnight at room temperature under 2 atm of hydrogen atmosphere. After the formation of reactant product was determined by LC-MS, the solid was filtered out and the filtrate was concentrated to obtain crude Compound 5e (430 mg). MS [M+1]$^+$ 499.3.

Step 4:

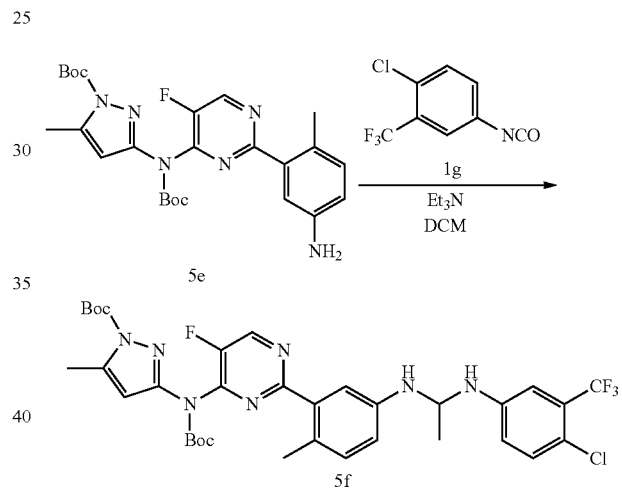

200 mg of the crude product of Compound 5e which obtained from the previous step (i.e, Compound 5e), Compound 1 g (98 mg, 0.44 mmol) and triethylamine (81 mg, 0.8 mmol) were dissolved in 10 mL of anhydrous dichloromethane and stirred at room temperature overnight. The solvent was concentrated, and the remainder was purified by silica gel column chromatography to obtain Compound 5f (60 mg, the two-step yield was 19%). MS [M+1]$^+$ 720.3.

Step 5:

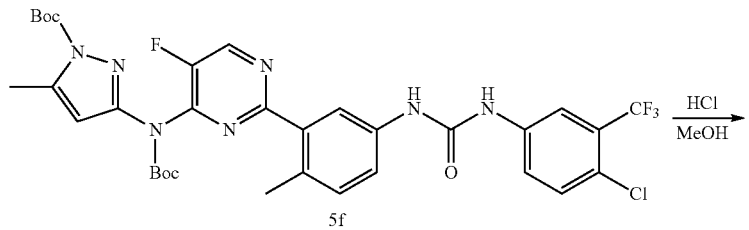

-continued

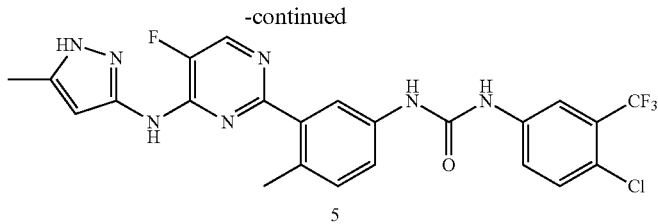

5

Compound 5f (60 mg, 0.08 mmol) was added to a methanol solution of 10 mL of 2M hydrochloric acid and stirred at room temperature overnight. The insoluble solid was collected and washed with ethyl acetate to obtain hydrochloride of 1-(4-chloro-3-trifluoromethyl-phenyl)-3-{3-[5-fluoro-4-(5-methyl-1H-pyrazol-3-yl-amino)-pyrimidin-2-yl]-4-methyl-phenyl}-urea (Compound 5) (20 mg, Yield 46%). $^1$H NMR (400 MHz, DMSO): δ ppm 11.18 (brs, 1H), 10.06 (brs, 1H), 9.64 (s, 1H), 8.70 (s, 1H), 8.14 (s, 1H), 7.91 (s. 1H). 7.61 (s, 2H). 7.46 (s, 1H), 7.28 (s, 1H), 6.52 (s, 1H), 2.37 (s, 3H), 2.26 (s, 3H); MS [M+1]$^+$520.2.

The following compounds can be prepared according to the method for preparing Compound 5.

When $R_2$=H, $R_3$=CH$_3$, $R_4$=4-chloro-3-trifluoromethyl-phenyl, K is absent, X=O, and A is phenyl, the compounds derived from varying $R_1$ are:

1-(4-chloro-3-trifluoromethyl-phenyl)-3-{4-[4-(5-ethyl-2H-pyrazole-3-amino)-pyrimidin-2-yl]-3-methyl-phenyl}-urea 1-{4-[4-(5-chloro-2H-pyrazole-3-amino)-pyrimidin-2-yl]-3-methyl-phenyl}-3-(4-chloro-3-trifluoromethyl-phenyl)-urea 1-(4-chlor-3-trifluoromethyl-phenyl)-3-{4-[4 (5-ethyl-2H-pyrazole-3-amino)-pyrimidin-2-yl]-3-methyl-phenyl}-urea 5-(2-{4-[3-(4-chloro-3-trifluoromethyl-phenyl)-ureido]-2-methyl-phenyl}-pyrimidine-4-amino)-1H-pyrazole-3-formic acid 1-(4-chloro-3-trifluoromethyl-phenyl)-3-{3-methyl-4-[4-(5-oxo-5H-pyrazole-3-amino)-pyrimidin-2-yl]-phenyl}-urea 1-{4-[4-(5-acetyl-2H-pyrazole-3-amino)-pyrimidin-2-yl]-3-methyl-phenyl}-3-(4-chloro-3-trifluoromethyl-phenyl)-urea 5-(2-{4-[3-(4-chloro-3-trifluoromethyl-phenyl)-ureido]-2-methyl-phenyl}-pyrimidine-4-amino)-1H-pyrazole-3-formamide 1-(4-chloro-3-trifluoromethyl-phenyl-3-{3-methyl-4-[4-(5-nitro-2H-pyrazole-3-amino)-pyrimidin-2-yl]-phenyl}-urea 1-(4-chloro-3-trifluoromethyl-phenyl)-3-{3-methyl-4-[4-(5-phenyl-2H-pyrazole-3-amino)-pyrimidin-2-yl]-phenyl}-urea 1-(4-chloro-3-trifluoromethyl-phenyl)-3-{3-methyl-4-[4-(5-methyl-thio-2H-pyrazole-3-amino)-pyrimidin-2-yl]-phenyl}-urea 1-(4-chloro-3-trifluoromethyl-phenyl)-3-{4-[4 (5-methoxy-2H-pyrazole-3-amino)-pyrimidin-2-yl]-3-methyl-phenyl}-urea 1-{4-[4-(5-bromo-2H-pyrazole-3-amino)-pyrimidin-2-yl]-3-methyl-phenyl}-3-(4-chloro-3-trifluoromethyl-phenyl)-urea 1-{4-[4-(5-amino-2H-pyrazole-3-amino)-pyrimidin-2-yl]-3-methyl-phenyl}-3-(4-chloro-3-trifluoromethyl-phenyl)-urea 1-(4-choro-3-trifluoromethyl-phenyl)-3-{4-[4 (5-furan-2-yl-2H-pyrazole-3-amino)-pyrimidin-2-yl]-3-methyl-phenyl}-urea 1-{4-[4-(5-tertbutyl-2H-pyrazole-3-amino)-pyrimidin-2-yl]-3-methyl-phenyl}-3-(4-chloro-3-trifluoromethyl-phenyl)-urea 1-(4-chloro-3-trifluoromethyl-phenyl)-3-{4-[4 (5-cyclopropyl-2H-pyrazole-3-amino)-pyrimidin-2-yl]-3-methyl-phenyl}-urea 1-(4-chloro-3-trifluoromethyl-phenyl)-3-{4-[4 (5-cyclobutyl-2H-pyrazole-3-amino)-pyrimidin-2-yl]-3-methyl-phenyl}-urea 1-(4-chloro-3-trifluoromethyl-phenyl)-3-{3-methyl-4-[4-(5-thien-2-yl-2H-pyrazole-3-amino)-pyrimidin-2-yl]-phenyl}-urea 1-(4-chloro-3-trifluoromethyl-phenyl)-3-{3-methyl-4-{4-[5-(1H-pyrrol-2-yl)-2H-pyrazole-3-amino]-pyrimidin-2-yl}-phenyl}-urea 1-(4-chloro-3-trifluoromethyl-phenyl)-3-{4-[4 (5-cyano-2H-pyrazole-3-amino)-pyrimidin-2-yl]-3-methyl-phenyl}-urea 5-(2-{4-[3-(4-chloro-3-trifluoromethyl-phenyl)-ureido]-2-methyl-phenyl}-pyrimidine-4-amino)-1H-pyrazole-3-carboximidic acid methyl ester 1-(4-chloro-3-trifluoromethyl-phenyl)-3-{3-methyl-4-[4-(2H-pyrazole-3-amino)-pyrimidin-2-yl]-phenyl}-urea 1-(4-chloro-3-trifluoromethyl-phenyl)-3-{4-[4-(5-fluoro-2H-pyrazole-3-amino)-pyrimidin-2-yl]-phenyl}-urea 1-(4-chloro-3-trifluoromethyl-phenyl)-3-{4-[4-(5-ethoxy-2H-pyrazole-3-amino)-6-methyl-pyrimidin-2-yl]-phenyl}-urea 1-(4-chloro-3-trifluoromethyl-phenyl)-3-{4-[4-(5-hydroxy-2H-pyrazol-3-yl-methyl)-pyrimidin-2-yl]-phenyl}-urea 5-(2-{4-[3-(4-chloro-3-trifluoromethyl-phenyl)-ureido]-phenyl}-pyrimidin-4-yl-methyl)-1H-pyrazol-3-yl acetate Ethyl 5-(2-{4-[3-(4-chloro-3-trifluoromethyl-phenyl)-ureido]-phenyl}-pyrimidin-4-yl-methyl)-1 H-pyrazole-3-formate N-[5-(2-{4-[3-(4-chloro-3-trifluoromethyl-phenyl)-ureido]-2-methyl-phenyl}-pyrimidine-4-amino)-1H-pyrazol-3-yl]-acetamide 5-(2-{4-[3-(4-chloro-3-trifluoromethyl-phenyl)-ureido]-2-methyl-phenyl}-pyrimidine-4-amino)-1H-pyrazole-3-formamidine 1-(4-chloro-3-trifluoromethyl-phenyl)-3-(4-{4-[5-(1-hydroxy-ethyl)-2H-pyrazole-3-amino]-pyrimidin-2-yl}-3-methyl-phenyl)-urea 1-(4-chloro-3-trifluoromethyl-phenyl)-3-{3-methyl-4-[4-(5-morpholin-4-yl-2H-pyrazole-3-amino)-pyrimidin-2-yl]-phenyl}-urea 1-(4-chlor-3-trifluoromethyl-phenyl)-3-{4-[4-(5-dimethylamino-2H-pyrazole-3-amino)-pyrimidin-2-yl]-3-methyl-phenyl}-urea 1-(4-chloro-3-trifluoromethyl-phenyl)-3-{4-[4-(5-ethynyl-2H-pyrazole-3-amino)-pyrimidin-2-yl]-3-methyl-phenyl}-urea 1-(4-chloro-3-trifluoromethyl-phenyl)-3-{3-methy-4-[4-(5-vinyl-2H-pyrazole-3-amino)-pyrimidin-2-yl]-phenyl}-urea 1-(4-chloro-3-trifluoromethyl-phenyl)-3-{3-methyl-4-[4-(5-piperazin-1-yl-2H-pyrazole-3-amino)-pyrimidin-2-yl]-phenyl}-urea 1-(4-chloro-3-trifluoromethyl-phenyl)-3-{3-methyl-4-[4-(5'-methyl-1H,2'H-[3,3']-dipyrazolyl-5-amino)-pyrimidin-2-yl]-phenyl}-urea Example 6

Synthesis of 1-(4-chloro-3-trifluoromethyl-phenyl)-3-{4-methyl-3-[5-methyl-4-(5-methyl-1H-pyrazol-3-yl-amino)-pyrimidin-2-yl-amino]-phenyl}-urea (Compound 6)

Synthesis Route 6:

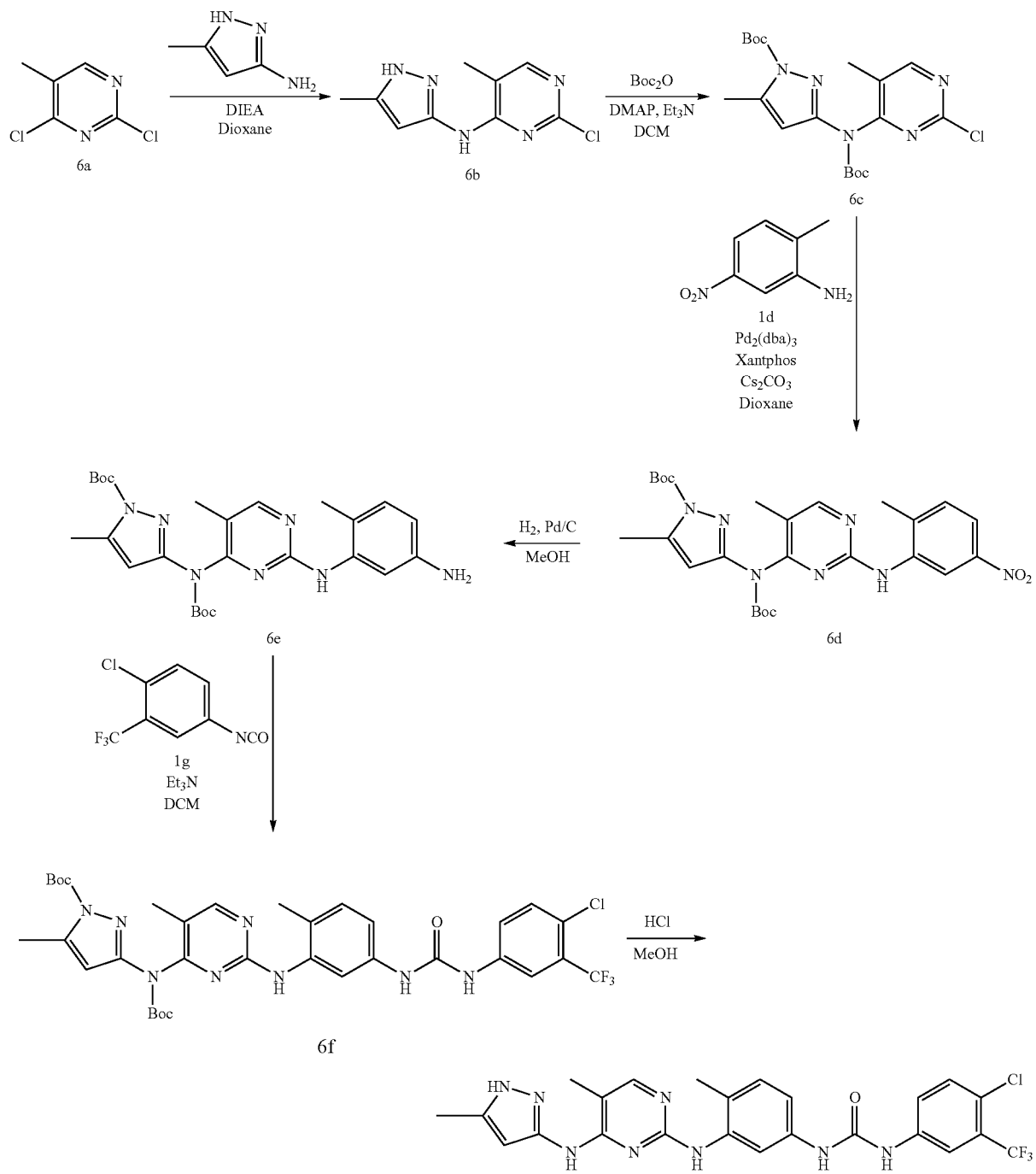

Step 1:

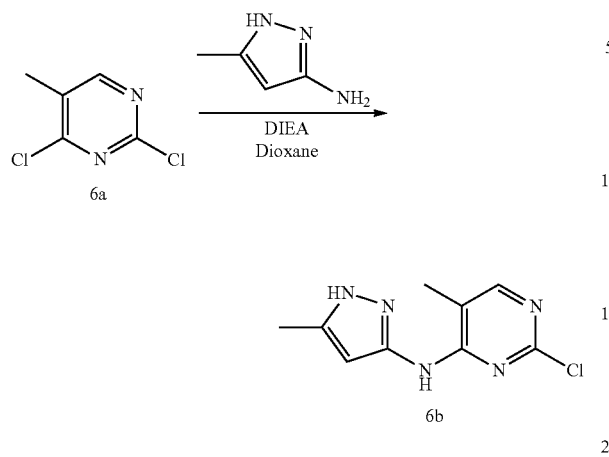

Compound 6a (3.3 g, 20 mmol), 3-amino-5-methyl-pyrazole (1.94 g, 20 mmol) and diisopropylethylamine (5.17 g, 40 mmol) were added to a solution of 20 mL of dioxane and heated to reflux overnight. The solvent was concentrated, and the remainder was purified by silica gel column chromatography to obtain Compound 6b (1.5 g, Yield 33%). $^1$H NMR (400 MHz, DMSO): δ ppm 12.18 (s, 1H), 9.31 (s, 1H), 7.97 (s, 1H), 6.37 (s, 1H), 2.25 (s, 3H), 2.12 (s, 3H); MS [M+1]$^+$ 224.1.

Step 2:

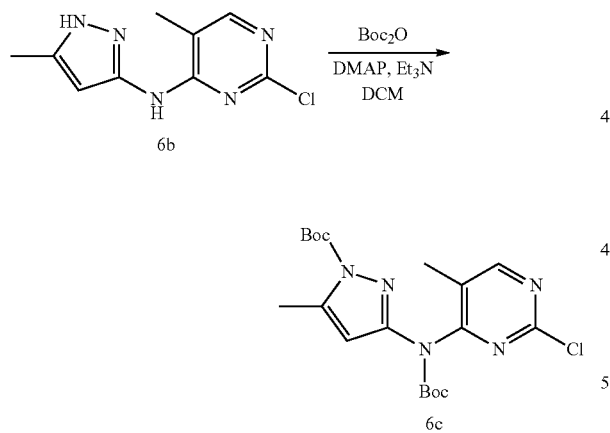

Compound 6b (1.5 g, 6.7 mmol), Et$_3$N (2.0 g, 20 mmol), DMAP (100 mg, 0.8 mmol) were dissolved in 20 mL of dichloromethane, and then Boc$_2$O (3.8 g, 18 mmol) was added dropwise to the solution. The mixture was stirred at room temperature overnight. The solvent was concentrated, and the remainder was purified by silica gel column chromatography to obtain Compound 6c (2.45 g, Yield 86%). $^1$H NMR (400 MHz, CDCl$_3$): δ ppm 8.51 (s, 1H), 6.46 (s, 1H), 2.49 (s, 3H), 2.24 (s, 3H), 1.56 (s, 9H), 1.45 (s, 9H); and 8.42 (d, J=0.8, 1H), 6.02 (s, 1H), 2.30 (s, 3H), 2.26 (s, 3H), 1.60 (s, 9H), 1.45 (s, 9H); MS [M+1]$^+$ 424.2.

Step 3:

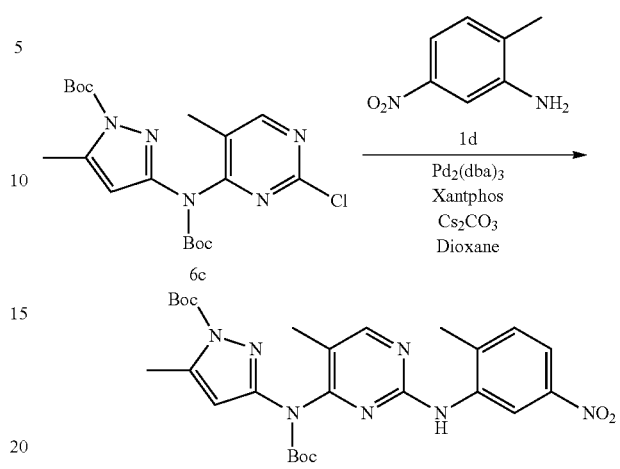

Compound 6c (551 mg, 1.3 mmol), Compound 1d (230 mg, 1.5 mmol), Pd$_2$(dba)$_3$ (130 mg, 0.14 mmol), xantphos (160 mg, 0.27 mmol), Cs$_2$CO$_3$ (880 mg, 2.7 mmol) and dioxane (15 mL) were added into a degassed flask and heated to reflux for 3 hours under the protection of argon. The solvent was concentrated, and the remainder was purified by silica gel column chromatography to obtain Compound 6d (370 mg, Yield 52%). NMR (400 MHz, CDCl$_3$): δ ppm 9.02 (d, J=6.0, 1H), 8.40 (s, 1H), 7.76 (dd, J$_1$=8.4, J$_2$=2.4, 1H), 7.27 (s, 1H), 6.93 (s, 1H), 6.49 (s, 1H), 2.51 (s, 3H), 2.38 (s, 3H), 2.20 (s, 3H), 1.56 (s, 9H), 1.45 (s, 9H); MS [M+1]$^+$ 540.3.

Step 4:

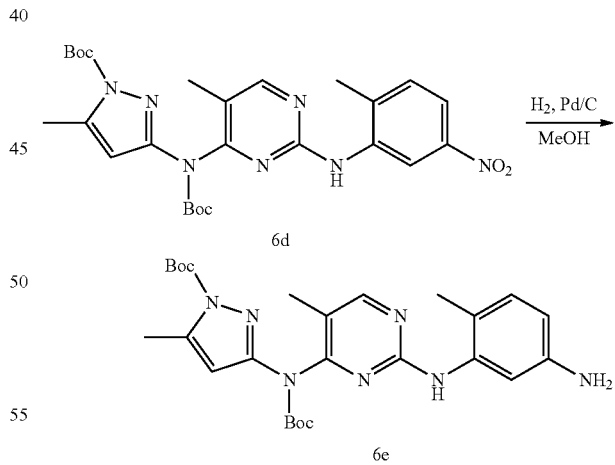

Compound 6d (370 mg, 0.69 mmol) and 10% Pd/C (50 mg) were added to 20 mL of methanol and reacted overnight at room temperature under 2 atm of hydrogen atmosphere. After the formation of reactant product was determined by LC-MS, the solid was filtered out and the filtrate was concentrated to obtain crude Compound 6e, which was used directly for the next step. MS [M+1]$^+$ 510.3.

Step 5:

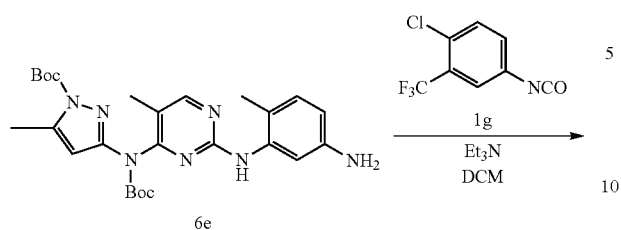

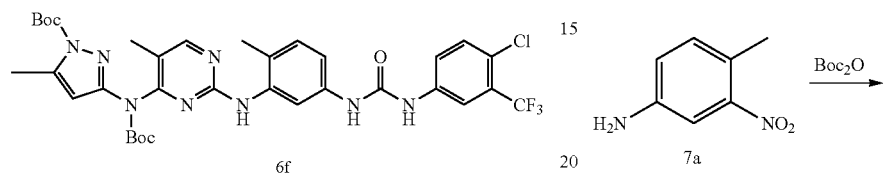

The crude product of Compound 6e which obtained from the previous step, Compound 1 g (167 mg, 0.75 mmol) and triethylamine (138 mg, 1.37 mmol) were dissolved in 5 mL of anhydrous dichloromethane and stirred at room temperature for 2 hours. The solvent was concentrated, and the remainder was purified by silica gel column chromatography to obtain Compound 6f (320 mg, the two-step yield was 63%). $^1$H NMR (400 MHz, CDCl$_3$): δ ppm 8.19 (s, 1H), 8.11 (s, 1H), 7.88 (s, 1H), 7.63 (s, 1H), 7.57 (d, J=8.4, 1H), 7.31 (m, 2H), 6.85 (m, 2H), 6.63 (s, 1H), 6.57 (s, 1H), 2.49 (s, 3H), 2.01 (s, 3H), 1.93 (s, 3H), 1.51 (s, 9H), 1.42 (s, 9H); MS [M+1]$^+$ 731.3.

Step 6:

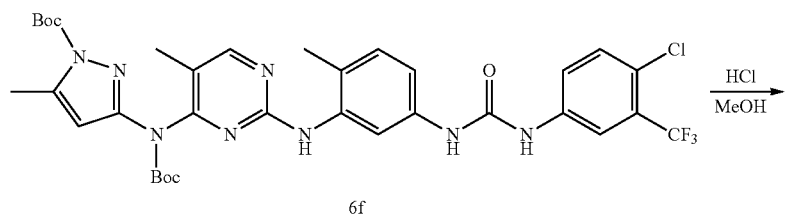

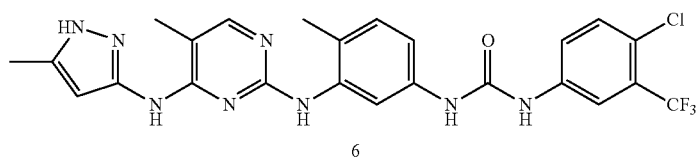

Compound 6f (320 mg, 0.43 mmol) was added to a methanol solution of 10 mL of 2M hydrochloric acid and stirred at room temperature overnight. The insoluble solid was collected and washed with ethyl acetate to obtain hydrochloride of 1-(4-chloro-3-trifluoromethyl-phenyl)-3-{4-methyl-3-[5-methyl-4-(5-methyl-1H-pyrazol-3-yl-amino)-pyrimidin-2-yl-amino]-phenyl}-urea (Compound 6) (230 mg, Yield 83%). $^1$H NMR (400 MHz, DMSO): δ ppm 12.44 (s, 1H), 10.26 (s, 1H), 10.06 (s, 1H), 10.04 (s, 1H), 9.62 (s, 1H), 8.10 (s, 1H), 7.79 (s, 1H), 7.60 (s, 2H), 7.56 (d, J=2.0, 1H), 7.37 (dd, J$_1$=8.4, J$_2$=2.0, 1H), 7.27 (d, J=8.4, 1H), 6.07 (s, 1H), 2.14 (s, 3H), 2.12 (s, 3H), 2.10 (s, 3H); MS [M+1]$^+$531.2.

Example 7

Synthesis of 1-(4-chloro-3-trifluoromethyl-phenyl)-3-{4-methyl-3-[5-methyl-4-(5-methyl-H-pyrazol-3-yl-amino)-5-nitro-pyrimidin-2-yl-amino]-phenyl}-urea (Compound 7)

Synthesis Route 7:

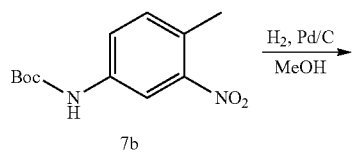

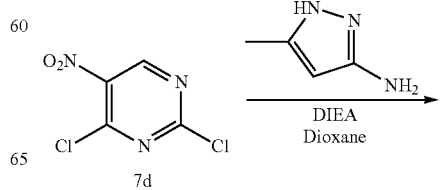

-continued

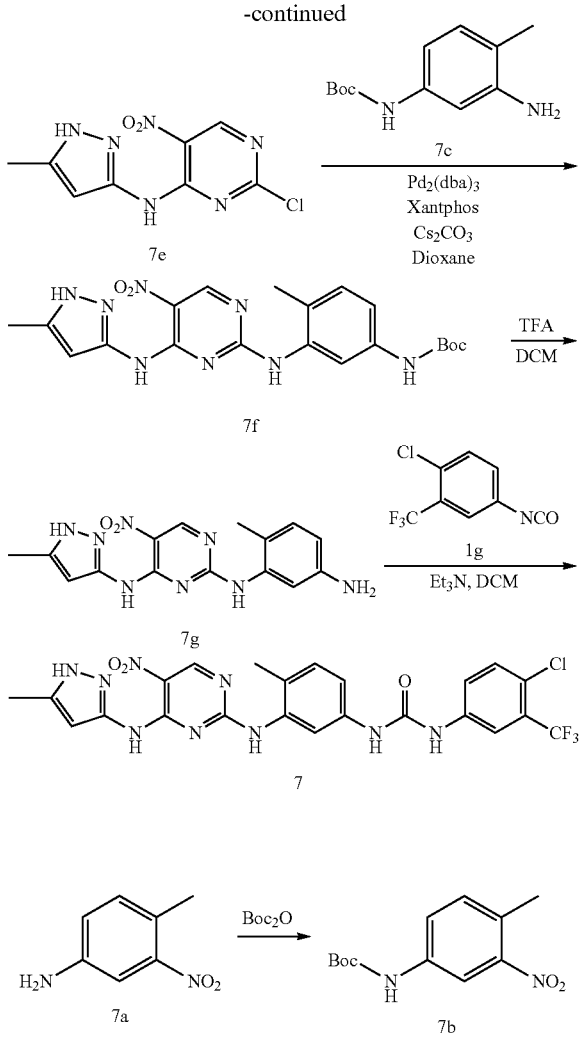

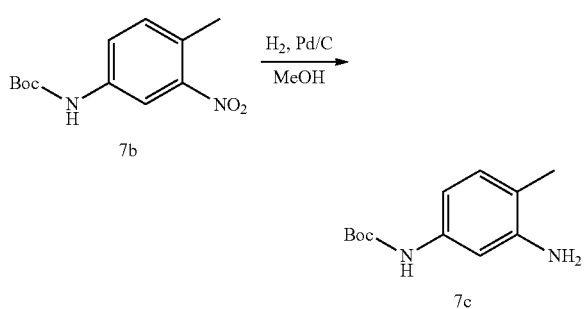

Compound 7a (2 g, 13.1 mmol) and Et₃N (2.6 g, 26.2 mmol) were dissolved in 30 mL of tetrahydrofuran, and then Boc₂O (3.4 g, 15.7 mmol) was added dropwise to the solution. The mixture was stirred at 60° C. overnight. The solvent was concentrated, and the remainder was purified by silica gel column chromatography to obtain Compound 7b (2.9 g, Yield 88%). $^1$H NMR (400 MHz, CDCl₃): δ ppm 8.07 (d, J=2.4, 1H), 7.50 (d, J=7.6, 1H), 7.23 (d, J=8.4, 1H), 6.81 (brs, 1H), 2.53 (s, 3H), 1.53 (s, 9H).

Step 2:

Compound 7b (2.9 g, 11.5 mmol) and 10% Pd/C (290 mg) were added to 30 mL of methanol and reacted overnight at room temperature under 2 atm of hydrogen atmosphere. After the formation of reactant product was determined by LC-MS, the solid was filtered out and the filtrate was concentrated to obtain Compound 7c (2.3 g, Yield 91%). $^1$H NMR (400 MHz, CDCl₃): δ ppm 6.97 (s, 1H), 6.94 (d, J=8.0, 1H), 6.51 (dd, $J_1$=2.0, $J_2$=2.0, 1H), 6.34 (brs, 1H), 3.62 (brs, 2H), 2.12 (s, 3H), 1.53 (s, 9H); MS [M−55]$^+$ 167.1.

Step 3:

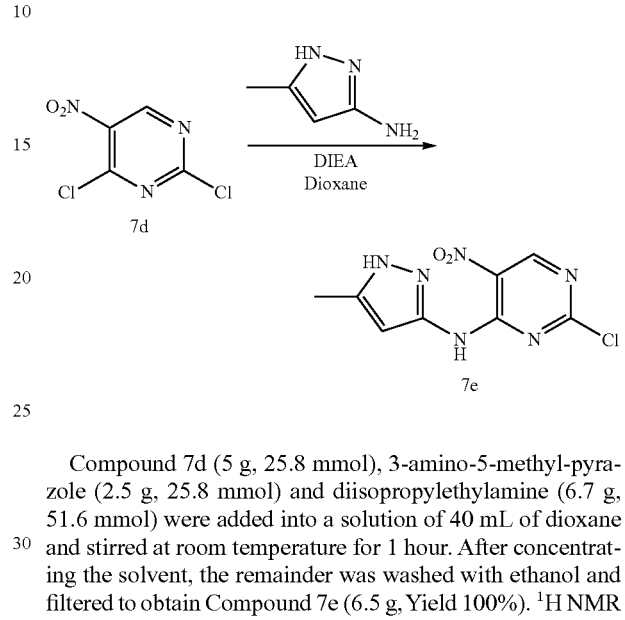

Compound 7d (5 g, 25.8 mmol), 3-amino-5-methyl-pyrazole (2.5 g, 25.8 mmol) and diisopropylethylamine (6.7 g, 51.6 mmol) were added into a solution of 40 mL of dioxane and stirred at room temperature for 1 hour. After concentrating the solvent, the remainder was washed with ethanol and filtered to obtain Compound 7e (6.5 g, Yield 100%). $^1$H NMR (400 MHz, CDCl₃): δ ppm 9.19 (s, 1H), 6.73 (s, 1H), 2.41 (s, 3H); MS [M+1]$^+$ 255.0.

Step 4:

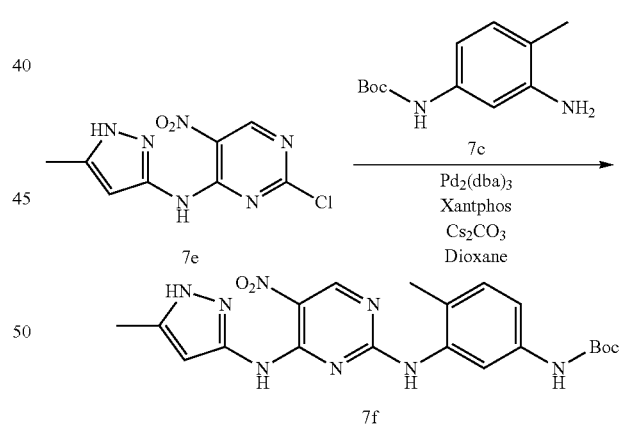

Compound 7e (500 mg, 1.96 mmol), Compound 7c (480 mg, 2.16 mmol), Pd₂(dba)₃ (179 mg, 0.196 mmol), xantphos (226 mg, 0.39 mmol), Cs₂CO₃ (1.28 g, 3.92 mmol) and dioxane (15 mL) were added to a degassed flask and heated to reflux for 3 hours under the protection of argon.

The solvent was concentrated, and the remainder was purified by silica gel column chromatography to obtain Compound 7f (350 mg, Yield 41%). $^1$H NMR (400 MHz, CD₃OD): δ ppm 9.01 (s, 1H), 7.53 (s, 1H), 7.38 (s, 1H), 7.19 (d, J=7.6, 1H), 5.92 (s, 1H), 2.19 (s, 3H), 2.11 (s, 3H), 1.49 (s, 9H); MS [M+1]$^+$ 441.2.

Step 5:

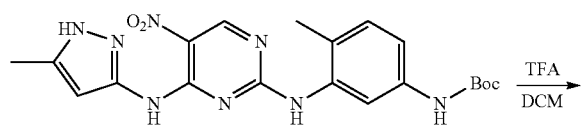

tro-pyrimidin-2-yl-amino]-phenyl}-urea (Compound 7) (201 mg, the two-step yield was 45%). ¹H NMR (400 MHz, DMSO): δ ppm 12.18 (s, 1H), 10.36 (s, 1H), 10.14 (s, 1H), 9.10 (m, 2H), 8.09 (s, 1H), 7.60 (s, 2H), 7.46 (m, 2H), 7.25 (d, J=8.0, 1H), 5.84 (s, 1H), 2.14 (s, 3H), 2.00 (s, 3H); MS [M+1]⁺ 562.2.

Example 8

Synthesis of 1-(4-chloro-3-trifluoromethyl-phenyl)-3-{4-methyl-3-[5-methyl-4-(5-methyl-1H-pyrazol-3-yl-amino)-5-amino-pyrimidin-2-yl-amino]-phenyl}-urea (Compound 8)

Synthesis Route 8:

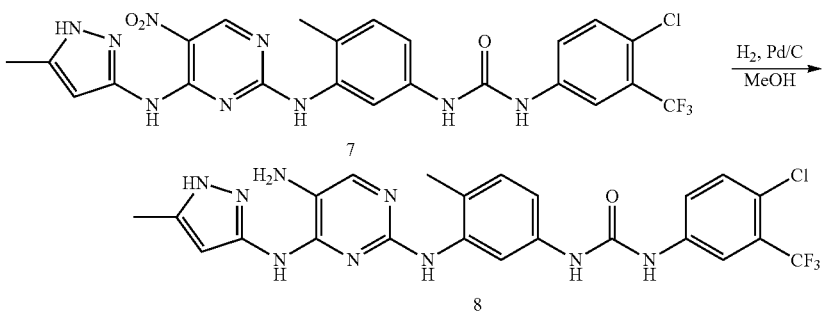

4 mL of TFA was added dropwise to 12 mL of dichloromethane and stirred at room temperature for 1 hour. After concentrating the solvent, the resulting crude Compound 7 g was used directly for the next reaction.

Step 6:

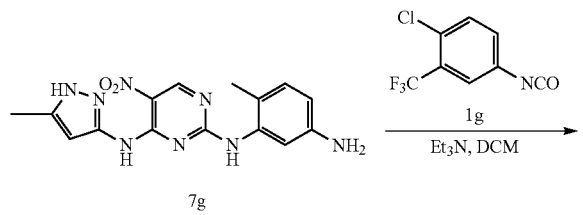

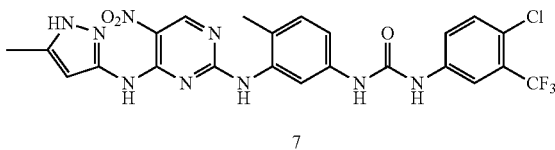

The crude product of Compound 7 g which obtained from the previous step, Compound 1 g (194 mg, 0.87 mmol) and triethylamine (241 mg, 2.39 mmol) were dissolved in 10 mL of anhydrous dichloromethane and stirred at room temperature for 2 hours. The solvent was concentrated, and the remainder was purified by silica gel column chromatography to obtain 1-(4-chloro-3-trifluoromethyl-phenyl)-3-{4-methyl-3-[5-methyl-4-(5-methy-1H-pyrazol-3-yl-amino)-5-ni- Compound 7b (40 mg, 0.07 mmol) and 10% Pd/C (4 mg) were added to 5 mL of methanol and reacted overnight at room temperature under 2 atm of hydrogen atmosphere. After the formation of reactant product was determined by LC-MS, the solid was filtered out and the filtrate was concentrated and purified by silica gel column chromatography to obtain 1-(4-chloro-3-trifluoromethyl-phenyl)-3-{4-methyl-3-[5-methyl-4-(5-methyl-1H-pyrazol-3-yl-amino)-5-amino-pyrimidin-2-yl-amino]-phenyl}-urea (Compound 8) (23 mg. Yield 61%). ¹H NMR (400 MHz, CD₃OD): δ ppm 8.04 (d, J=2.4, 1H), 7.70 (d, J=1.2, 1H), 7.62 (dd, J₁₌₂.₄, J₂=2.8, 1H), 7.50 (m, 2H), 7.34 (m, 2H), 6.50 (s, 1H), 2.44 (s, 3H), 2.31 (s, 3H); MS [M+1]⁺ 532.2.

Example 9

Synthesis of 1-(4-chloro-3-trifluoromethyl-phenyl)-3-{3-[5-methoxy-4-(5-methyl-1H-pyrazol-3-yl-amino)-pyrimidin-2-yl-amino]-4-methyl-phenyl}-urea (Compound 9)

Synthesis Route 9:

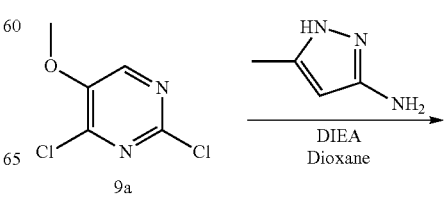

-continued

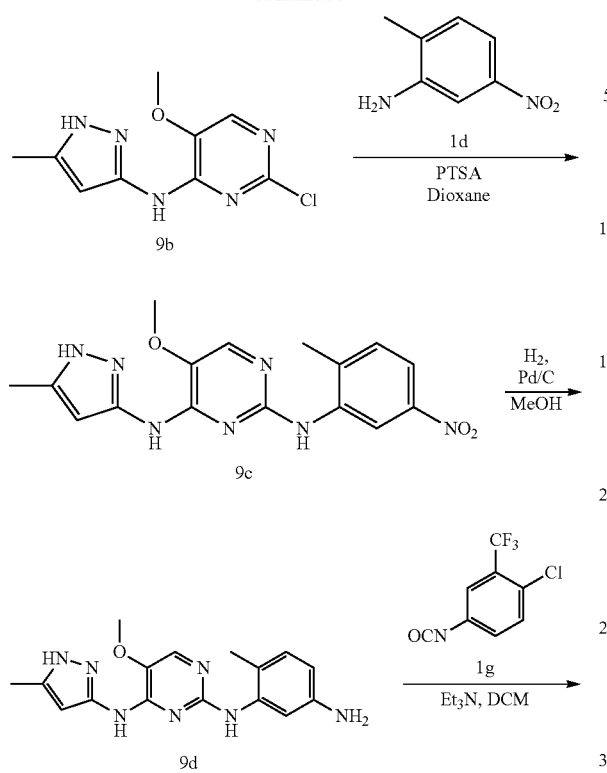

Step 1:

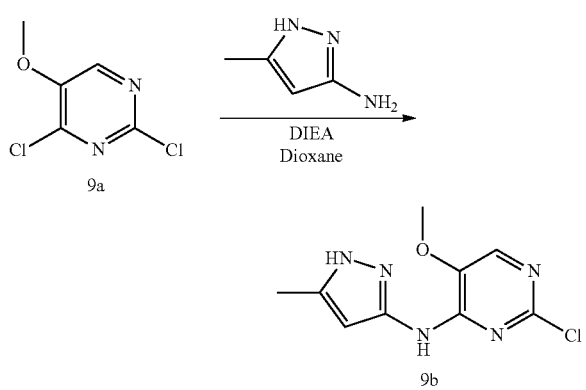

Compound 9a (3 g, 16.8 mmol), 3-amino-5-methyl-pyrazole (1.6 g, 16.8 mmol) and diisopropylethylamine (4.3 g, 33.6 mmol) were added to a solution of 25 mL of dioxane and stirred at room temperature for 48 hours. After concentrating the solvent, the remainder was washed with ethanol and filtered to obtain Compound 9b (2.4 g, Yield 60%). MS [M+1]$^+$ 240.1.

Step 2:

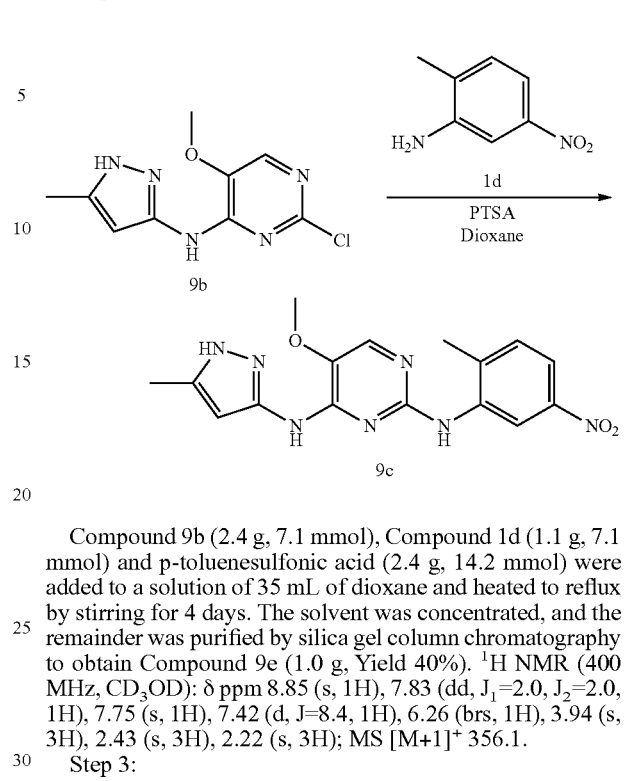

Compound 9b (2.4 g, 7.1 mmol), Compound 1d (1.1 g, 7.1 mmol) and p-toluenesulfonic acid (2.4 g, 14.2 mmol) were added to a solution of 35 mL of dioxane and heated to reflux by stirring for 4 days. The solvent was concentrated, and the remainder was purified by silica gel column chromatography to obtain Compound 9e (1.0 g, Yield 40%). $^1$H NMR (400 MHz, CD$_3$OD): δ ppm 8.85 (s, 1H), 7.83 (dd, J$_1$=2.0, J$_2$=2.0, 1H), 7.75 (s, 1H), 7.42 (d, J=8.4, 1H), 6.26 (brs, 1H), 3.94 (s, 3H), 2.43 (s, 3H), 2.22 (s, 3H); MS [M+1]$^+$ 356.1.

Step 3:

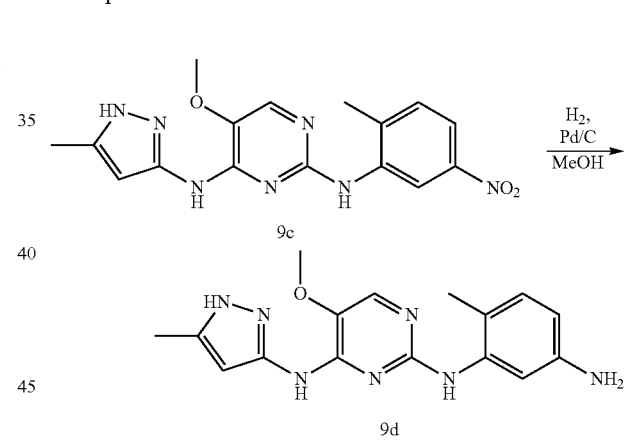

Compound 9c (460 mg, 1.30 mmol) and 10% Pd/C (46 mg) were added to 30 mL of methanol and reacted overnight at room temperature under 2 atm of hydrogen atmosphere. After the formation of reactant product was determined by LC-MS, the solid was filtered out and the filtrate was concentrated and the resulting crude Compound 9d, was used directly for the next reaction.

Step 4:

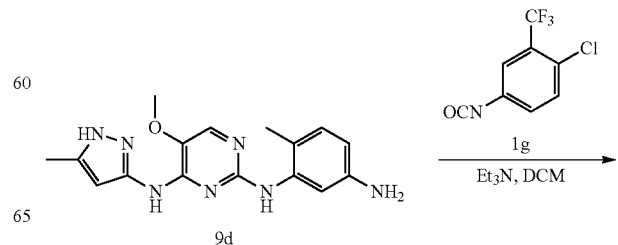

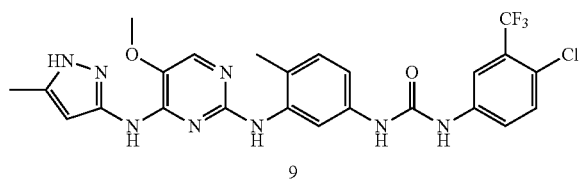

The crude product of compound 9d which obtained from the previous step (i.e., Compound 9d), Compound 1 g (245 mg, 1.1 mmol) and triethylamine (222 mg, 2.2 mmol) were dissolved in 20 mL of anhydrous dichloromethane and stirred at room temperature for 2 hours. The solvent was concentrated, and the remainder was purified by silica gel column chromatography to obtain 1-(4-chloro-3-trifluoromethyl-phenyl)-3-{3-[5-methoxy-4-(5-methyl-1H-pyrazol-3-yl-amino)-pyrimidin-2-yl-amino]-4-methyl-phenyl}-urea (Compound 9) (250 mg, the two-step yield was 35%). $^1$H NMR (400 MHz, CD3OD): δ ppm 7.96 (d, J=2.0, 1H), 7.69 (s, 1H), 7.62 (m, 2H), 7.49 (d, J=8.8, 1H), 7.21 (m, 2H), 6.18 (s, 1H), 3.90 (s, 3H), 2.26 (s, 3H), 2.20 (s, 3H); MS [M+1]+ 547.2.

Example 10

Synthesis of 1-{3-[5-benzyloxy-4-(5-methyl-1H-pyrazol-3-yl-amino)-pyrimidin-2-yl-amino]-4-methyl-phenyl}-3-(4-chloro-3-trifluoromethyl-phenyl)-urea (Compound 10)

Synthesis Route 10:

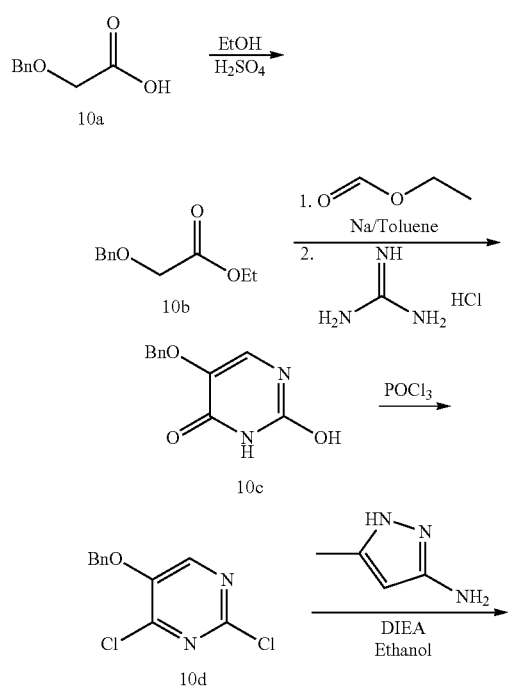

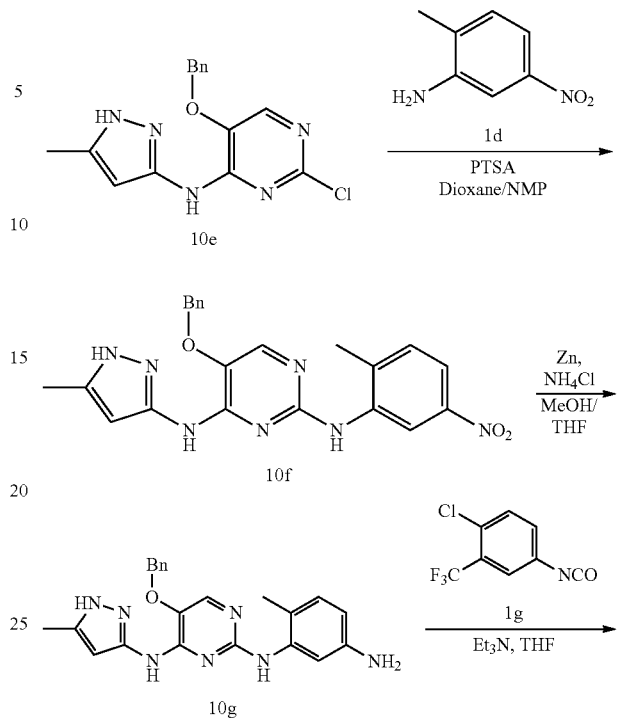

Step 1:

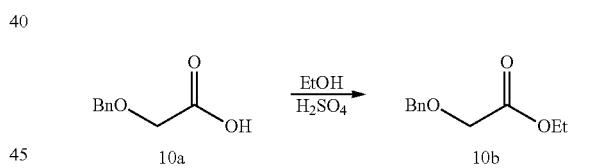

A catalytic amount of concentrated sulfuric acid was added to Compound 10a (33.2 g, 0.2 mol) in ethanol (300 mL) solution. The reaction was heated to reflux overnight. The solvent was concentrated, and the resulting residue was dissolved into ethyl acetate, and then washed with saturated aqueous sodium bicarbonate solution. The organic phase was collected and dried over anhydrous sodium sulfate. The solvent was concentrated to obtain Compound 10b (35 g, Yield 90%).

Step 2:

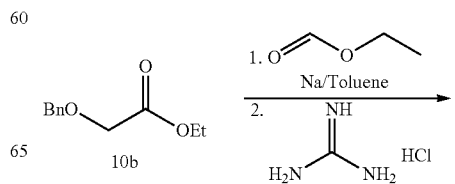

-continued

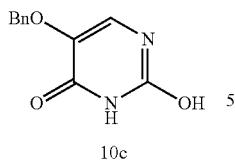
10c

Sodium (7.13 g, 0.31 mol) was added to 500 mL of toluene. Then ethyl formate (22.9 g, 0.31 mol) and Compound 10b (60 g, 0.31 mol) were added dropwise to the above solution at a temperature of below 30° C. The reaction mixture was stirred at room temperature overnight. The solvent was concentrated, and the resulting residue was dissolved in 300 mL of ethanol, and then guanidine hydrochloride (29.45 g, 0.31 mol) was added thereto. The reaction was heated to reflux overnight. The solvent was concentrated and 100 mL of water was added to the residue, which was adjusted with 1N HCl to pH=2. The insoluble solid was collected and dried to obtain Compound 10c (30 g, Yield 44%). MS [M+1]$^+$ 219.1.

Step 3:

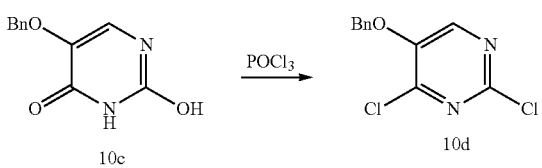

Compound 10c (8.9 g, 40 mmol) was added to 100 mL of POCl$_3$ and heated to reflux for 5 hours. After distilling off part of POCl$_3$, ice water was added to the reminder. The mixture was adjusted with aqueous ammonia at a temperature of below 10° C. to pH=7-8, and then extracted with ethyl acetate. The organic phase was dried over anhydrous sodium sulfate, and the solvent was concentrated to obtain Compound 10d (1.7 g, Yield 16.7%). MS [M+1]$^+$ 255.1.

Step 4:

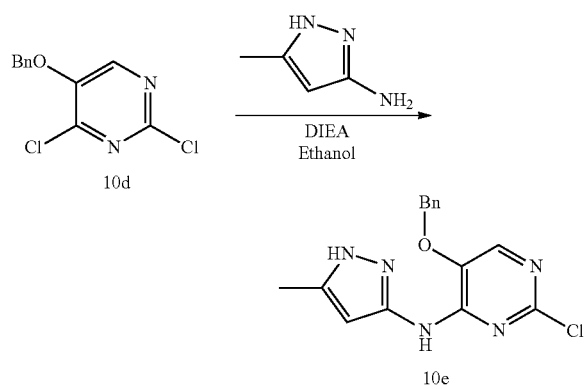

Compound 10d (1.5 g, 5.9 mmol), 3-amino-5-methyl-pyrazole (578 mg, 5.9 mmol) and diisopropyl ethylamine (1.5 g, 12 mmol) were added to a solution of 20 mL of ethanol. The mixture was stirred at room temperature overnight. The solvent was concentrated, and the remainder was separated by silica gel column to obtain Compound 10e (650 mg, Yield 35%). MS [M+1]$^+$ 316.1.

Step 5:

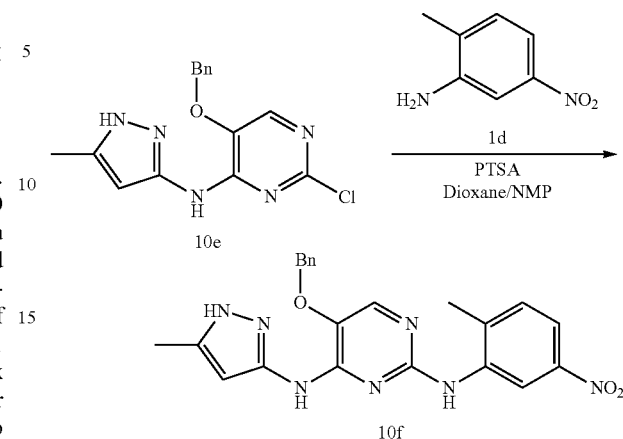

Compound 10e (650 mg, 2.05 mmol), Compound 1d (375 mg, 2.45 mmol) and a catalytic amount of p-toluenesulfonic acid were added to a solution of 10 mL of dioxane and heated to reflux with stirred for 7 days. The solvent was concentrated, and the remainder was separated by silica gel column to obtain crude Compound 10f (600 mg). MS [M+1]$^+$ 432.1.

Step 6:

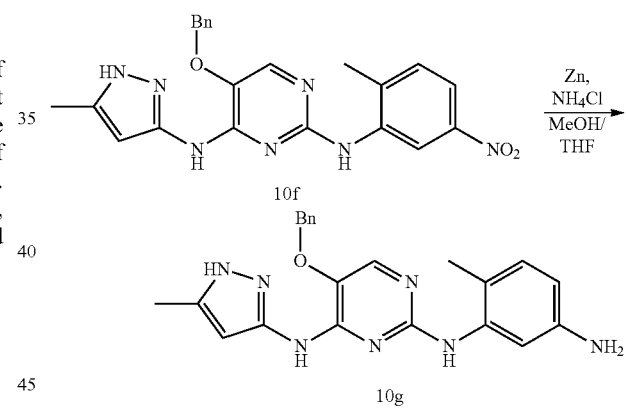

Compound 10f (600 mg, the crude product), zinc powder (904 mg, 13.9 mmol) and ammonium chloride (738 mg, 13.9 mmol) were added to a mixed solvent of methanol (10 mL) and tetrahydrofuran (10 mL) and then reacted at room temperature for 5 hours. The solid was filtered, and the filtrate was concentrated to obtain crude Compound 10 g (250 mg). MS [M+1]$^+$402.1.

Step 7:

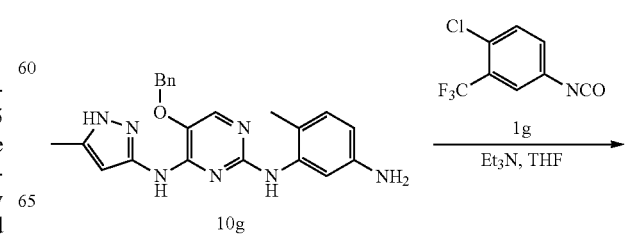

-continued

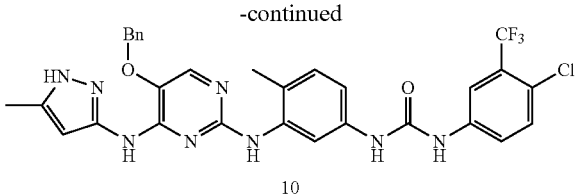

10

Compound 10 g (250 mg, 0.62 mmol), Compound 1 g (137 mg, 0.62 mmol) and Et$_3$N (125 mg, 1.24 mmol) were added to anhydrous tetrahydrofuran (10 mL) and then stirred at room temperature for 2 hours. The filtrate was concentrated and purified by column separation on silica gel to obtain 1-{3-[5-benzyloxy-4-(5-methyl-1H-pyrazol-3-yl-amino)-pyrimidin-2-yl-amino]-4-methyl-phenyl}-3-(4-chloro-3-trifluoromethyl-phenyl)-urea (Compound 10) (170 mg, Yield 44%). $^1$H NMR (400 MHz, CD$_3$OD) δ ppm: 8.03 (s, 1H), 7.95 (s, 1H), 7.66 (m, 3H), 7.46 (m, 5H), 7.34 (s, 2H), 6.46 (s, 1H), 5.24 (s, 2H), 2.36 (s, 3H), 2.28 (s, 3H); MS [M+1]$^+$ 623.0.

Example 11

Synthesis of 1-(4-chloro-3-trifluoromethyl-phenyl)-3-{3-[5-hydroxy-4-(5-methyl-1H-pyrazol-3-yl-amino)-pyrimidin-2-yl-amino]-4-methyl-phenyl}-urea (Compound 11)

Synthesis Route 11

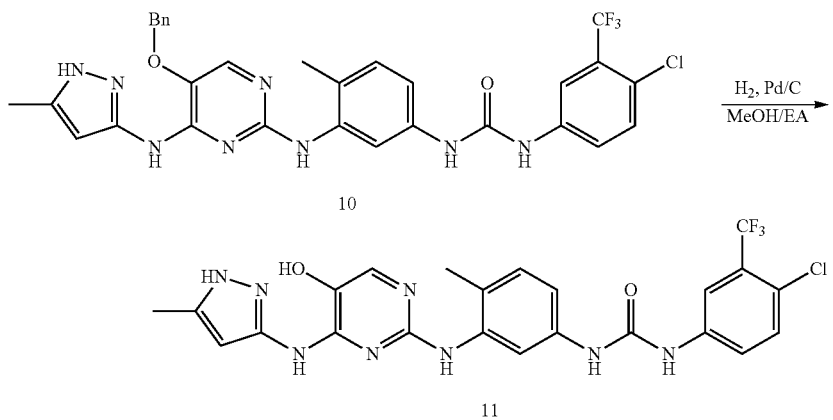

Compound 10 (120 mg, 0.19 mmol), 10% Pd/C (100 mg) and 3 drops of concentrated hydrochloric acid were added to a solvent of 10 mL of methanol and 10 mL of ethyl acetate, and reacted for 3 hours at room temperature under normal hydrogen atmosphere. After the formation of reactant product was determined by LC-MS, the solid was filtered out and the filtrate was concentrated and the resulting crude product was separated and purified by preparative TLC to obtain 1-(4-chloro-3-trifluoromethyl-phenyl)-3-{3-[5-hydroxy-4-(5-methyl-1H-pyrazol-3-yl-amino)-pyrimidin-2-yl-amino]-4-methyl-phenyl}-urea (Compound 11) (14 mg, Yield 13.8%). $^1$H NMR (400 MHz, CD$_3$OD): δ ppm: 8.03 (s, 1H), 7.64 (in, 2H), 7.43 (in, 1H), 7.33 (in, 3H), 6.52 (s, 1H), 2.45 (s, 3H), 2.30 (s, 3H); MS [M+1]$^+$ 533.0.

The following compounds can be prepared according to the methods which are similar to the methods for preparing the above-mentioned compounds.

When $R_1=R_2=R_3=CH_3$, $K=X=O$ and A is phenyl, the compounds derived from varying $R_4$ are:

1-(4-chloro-3-trifluoromethyl-phenyl)-3-{3-methyl-4-[4-methyl-6-(5-methyl-2H-pyrazole-3-amino)-pyrimidin-2-yl-oxy]-phenyl}-urea
1-(4-chlor-phenyl)-3-{3-methyl-4-[4-methyl-6-(5-methyl-2H-pyrazole-3-amino)-pyrimidin-2-yl-oxy]-phenyl}-urea
1-{3-methyl-4-[4-methyl-6-(5-methyl-2H-pyrazole-3-amino)-pyrimidin-2-yl-oxy]-phenyl}-3-m-tolyl-urea
1-(3,4-dichloro-phenyl)-3-{3-methyl-4-[4-methyl-6-(5-methyl-2H-pyrazole-3-amino)-pyrimidin-2-yl-oxy]-phenyl}-urea
1-(4-isopropyl-phenyl)-3-{3-methyl-4-[4-methyl-6-(5-methyl-2H-pyrazole-3-amino)-pyrimidin-2-yl-oxy]-phenyl}-urea
Benzol[1,3]dioxolan-5-yl-3-{3-methyl-4-[4-methy-6-(5-methyl-2H-pyrazole-3-amino)-pyrimidin-2-yl-oxy]-phenyl}-urea
1-{3-methyl-4-[4-methyl-6-(5-methyl-2H-pyrazole-3-amino)-pyrimidin-2-yl-oxy]-phenyl}-3-pyrid-4-yl-urea
1-(3-chloro-4-fluoro-phenyl)-3-{3-methyl-4-[4-methyl-6-(5-methyl-2H-pyrazole-3-amino)-pyrimidin-2-yl-oxy]-phenyl}-urea
1-{3-methyl-4-[4-methyl-6-(5-methyl-2H-pyrazole-3-amino)-pyrimidin-2-yl-oxy]-phenyl}-3-pyrimidin-5-yl-urea
1-(3-hydroxy-phenyl)-3-{3-methyl-4-[4-methyl-6-(5-methyl-2H-pyrazole-3-amino)-pyrimidin-2-yl-oxy]-phenyl}-urea
4 (3-{3-methyl-4-[4-methyl-6-(5-methyl-2H-pyrazole-3-amino)-pyrimidin-2-yl-oxy]-phenyl}-ureido)-benzoic acid
1-(3,5-dihydroxy-phenyl)-3-{3-methyl-4-[4-methyl-6-(5-methyl-2H-pyrazole-3-amino)-pyrimidin-2-yl-oxy]-phenyl}-urea
1-{3-methyl-4-[4-methyl-6-(5-methyl-2H-pyrazole-3-amino)-pyrimidin-2-yl-oxy]-phenyl}-3-(6-oxo-1,6-dihydro-pyrid-3-yl)-urea
Cyclohexyl-3-{3-methyl-4-[4-methyl-6-(5-methyl-2H-pyrazole-3-amino)-pyrimidin-2-yl-oxy]-phenyl}-urea
Tertbutyl-3-{3-methyl-4-[4-methyl-6-(5-methyl-2H-pyrazole-3-amino)-pyrimidin-2-yl-oxy]-phenyl}-urea
1-{3-methyl-4-[4-methyl-6-(5-methyl-2H-pyrazole-3-amino)-pyrimidin-2-yl-oxy]-phenyl}-3-(tetrahydropyran-4-yl)-urea
{3-methyl-4-[4-methyl-6-(5-methyl-2H-pyrazole-3-amino)-pyrimidin-2-yl-oxy]-phenyl}-urea
1-(3H-imidazol-4-yl)-3-{3-methyl-4-[4-methyl-6-(5-methyl-2H-pyrazole-3-amino)-pyrimidin-2-yl-oxy]-phenyl}-urea 1-{3-methyl-4-[4-methyl-6-(5-methyl-2H-pyrazole-3-amino)-pyrimidin-2-yl-oxy]-phenyl}-3-thiazol-5-yl-urea
1-{3-methyl-4-[4-methyl-6-(5-methyl-2H-pyrazole-3-amino)-pyrimidin-2-yl-oxy]-phenyl}-3-(3-nitro-phenyl)-urea
1-{3-methyl-4-[4-methyl-6-(5-methyl-2H-pyrazole-3-amino)-pyrimidin-2-yl-oxy]-phenyl}-3-quinolin-8-yl-urea
Methyl-3-{3-methyl-4-[4-methyl-6-(5-methyl-2H-pyrazole-3-amino)-pyrimidin-2-yl-oxy]-phenyl}-urea
1-{3-methyl-4-[4-methyl-6-(5-methyl-2H-pyrazole-3-amino)-pyrimidin-2-yl-oxy]-phenyl}-3-(3-methyl-thio-phenyl)-urea
1-{3-methyl-4-[4-methyl-6-(5-methyl-2H-pyrazole-3-amino)-pyrimidin-2-yl-oxy]-phenyl}-3-piperid-4-yl-urea
1-{3-methyl-4-[4-methyl-6-(5-methyl-2H-pyrazole-3-amino)-pyrimidin-2-yl-oxy]-phenyl}-3-(1-methyl-piperid-4-yl)-urea
1-(1-acetyl-piperid-4-yl)-3-{3-methyl-4-[4-methyl-6-(5-methyl-2H-pyrazole-3-amino)-pyrimidin-2-yl-oxy]-phenyl}-urea
Butyl-3-{3-methyl-4-[4-methyl-6-(5-methyl-2H-pyrazole-3-amino)-pyrimidin-2-yl-oxy]-phenyl}-urea
1-(1H-benzoimidazol-5-yl)-3-{-3-methyl-4-[4-methyl-5-methyl-2H-pyrazole-3-amino)-pyrimidin-2-yl-oxy]-phenyl}-urea
2-benzyl-3-{3-(3-methyl-4-[4-methyl-6-(5-methyl-2H-pyrazole-3-amino)-pyrimidin-2-yl-oxy]-phenyl}-ureido)-3-oxo-propionic acid
1-{3-methyl-4-[4-methyl-6-(5-methyl-2H-pyrazole-3-amino)-pyrimidin-2-yl-oxy]-phenyl}-3-thien-2-yl-urea
Furan-2-yl-3-{3-methyl-4-[4-methyl-6-(5-methyl-2H-pyrazole-3-amino)-pyrimidin-2-yl-oxy]-phenyl}-urea
1-{3-methyl-4-[4-methyl-6-(5-methyl-2H-pyrazole-3-amino)-pyrimidin-2-yl-oxy]-phenyl}-3-(1-methyl-1H-pyrrol-2-yl)-urea
Benzofuran-2-yl-3-{3-methyl-4-[4-methyl-6-(5-methyl-2H-pyrazole-3-amino)-pyrimidin-2-yl-oxy]-phenyl}-urea
Benzo[b]thien-2-yl-3-{3-methyl-4-[4-methyl-6-(5-methyl-2H-pyrazole-3-amino)-pyrimidin-2-yl-oxy]-phenyl}-urea
Cyclopentyl-3-{3-methyl-4-[4-methyl-6-(5-methyl-2H-pyrazole-3-amino)-pyrimidin-2-yl-oxy]-phenyl}-urea
Cyclobutyl-3-{3-methyl-4-[4-methyl-6-(5-methyl-2H-pyrazole-3-amino)-pyrimidin-2-yl-oxy]-phenyl}-urea
When $R_1=R_2=R_3=CH_3$, K=S, X=O, and A is phenyl, the compounds derived from varying $R_4$ are:
1-(4-chloro-3-trifluoromethyl-phenyl)-3-{3-methyl-4-[4-methyl-6-(5-methyl-2H-pyrazole-3-amino)-pyrimidin-2-yl-thio]-phenyl}-urea
1-(4-chlor-phenyl)-3-{3-methyl-4-[4-methy-6-(5-methyl-2H-pyrazole-3-amino)-pyrimidin-2-yl-thio]-phenyl}-urea
1-{3-methyl-4-[4-methyl-6-(5-methyl-2H-pyrazole-3-amino)-pyrimidin-2-yl-thio]-phenyl}-3-m-tolyl-urea
1-(3,4-dichloro-phenyl)-3-{3-methyl-4-[4-methyl-6-(5-methyl-2H-pyrazole-3-amino)-pyrimidin-2-yl-thio]-phenyl}-urea
1-(4-isopropyl-phenyl)-3-{3-methyl-4-[4-methyl-6-(5-methyl-2H-pyrazole-3-amino)-pyrimidin-2-yl-thio]-phenyl}-urea
1-Benzo[1,3]dioxolan-5-yl-3-{3-methyl-4-[4-methyl-6-(5-methyl-2H-pyrazole-3-amino)-pyrimidin-2-yl-thio]-phenyl}-urea
1-{3-methyl-4-[4-methyl-6-(5-methyl-2H-pyrazole-3-amino)-pyrimidin-2-yl-thio]-phenyl}-3-pyrid-4-yl-urea
1-(3-chloro-4-fluoro-phenyl)-3-{3-methyl-4-[4-methyl-6-(5-methyl-2H-pyrazole-3-amino)-pyrimidin-2-yl-thio]-phenyl}-urea
1-{3-methyl-4-[4-methyl-6-(5-methyl-2H-pyrazole-3-amino)-pyrimidin-2-yl-thio]-phenyl}-3-pyrimidin-5-yl-urea
1-(3-hydroxy-phenyl)-3-{3-methyl-4-[4-methyl-6-(5-methyl-2H-pyrazole-3-amino)-pyrimidin-2-yl-thio]-phenyl}-urea
4 (3-{3-methyl-4-[4-methyl-6-(5-methyl-2H-pyrazole-3-amino)-pyrimidin-2-yl-thio]-phenyl}-ureido)-benzoic acid
1-(3,5-dihydroxy-phenyl)-3-{3-methyl-4-[4-methyl-6-(5-methyl-2H-pyrazole-3-amino)-pyrimidin-2-yl-thio]-phenyl}-urea
1-{3-methyl-4-[4-methyl-6-(5-methyl-2H-pyrazole-3-amino)-pyrimidin-2-yl-thio]-phenyl}-3-(6-oxo-1,6-dihydro-pyrid-3-yl)-urea
1-cyclohexyl-3-{3-methyl-4-[4-methyl-6-(5-methyl-2H-pyrazole-3-amino)-pyrimidin-2-yl-thio]-phenyl}-urea
1-tertbutyl-3-{3-methyl-4-[4-methyl-6-(5-methyl-2H-pyrazole-3-amino)-pyrimidin-2-yl-thio]-phenyl}-urea
1-{3-methyl-4-[4-methyl-6-(5-methyl-2H-pyrazole-3-amino)-pyrimidin-2-yl-thio]-phenyl}-3-(tetrahydropyran-4-yl)-urea
{3-methyl-4-[4-methyl-6-(5-methyl-2H-pyrazole-3-amino)-pyrimidin-2-yl-thio]-phenyl}-urea
1-(3H-imidazol-4-yl)-3-{3-methyl-4-[4-methyl-6-(5-methyl-2H-pyrazole-3-amino)-pyrimidin-2-yl-thio]-phenyl}-urea
1-{3-methyl-4-[4-methyl-6-(5-methyl-2H-pyrazole-3-amino)-pyrimidin-2-yl-thio]-phenyl}-3-thiazol-5-yl-urea
1-{3-methyl-4-[4-methyl-6-(5-methyl-2H-pyrazole-3-amino)-pyrimidin-2-yl-thio]-phenyl}-3-(3-nitro-phenyl)-urea
1-{3-methyl-4-[4-methyl-6-(5-methyl-2H-pyrazole-3-amino)-pyrimidin-2-yl-thio]-phenyl}-3-quinolin-8-yl-urea
Methyl-3-{3-methyl-4-[4-methyl-6-(5-methyl-2H-pyrazole-3-amino)-pyrimidin-2-yl-thio]-phenyl}-urea
1-{3-methyl-4-[4-methyl-6-(5-methyl-2H-pyrazole-3-amino)-pyrimidin-2-yl-thio]-phenyl}-3-(3-methyl-thio-phenyl)-urea
1-{3-methyl-4-[4-methyl-6-(5-methyl-2H-pyrazole-3-amino)-pyrimidin-2-yl-thio]-phenyl}-3-piperid-4-yl-urea
1-{3-methyl-4-[4-methyl-6-(5-methyl-2H-pyrazole-3-amino)-pyrimidin-2-yl-thio]-phenyl}-3-(1-methyl-piperid-4-yl)-urea
1-(1-acetyl-piperid-4-yl)-3-{3-methyl-4-[4-methyl-6-(5-methyl-2H-pyrazole-3-amino)-pyrimidin-2-yl-thio]-phenyl}-urea
Butyl-3-{3-methyl-4-[4-methyl-6-(5-methyl-2H-pyrazole-3-amino)-pyrimidin-2-yl-thio]-phenyl}-urea
1-(1H-benzoimidazol-5-yl)-3-{3-methyl-4-[4-methyl-6-(5-methyl-2H-pyrazole-3-amino)-pyrimidin-2-yl-thio]-phenyl}-urea
2-benzyl-3-{3-(3-methyl-4-[4-methyl-6-(5-methyl-2H-pyrazole-3-amino)-pyrimidin-2-yl-thio]-phenyl}-ureido)-3-oxo-propionic acid
1-{3-methyl-4-[4-methyl-6-(5-methyl-2H-pyrazole-3-amino)-pyrimidin-2-yl-thio]-phenyl}-3-thien-2-yl-urea
Furan-2-yl-3-{3-methyl-4-[4-methyl-6-(5-methyl-2H-pyrazole-3-amino)-pyrimidin-2-yl-thio]-phenyl}-urea
1-{3-methyl-4-[4-methyl-6-(5-methyl-2H-pyrazole-3-amino)-pyrimidin-2-yl-thio]-phenyl}-3-(1-methyl-1H-pyrrol-2-yl)-urea
Benzofuran-2-yl-3-{3-methyl-4-[4-methyl-6-(5-methyl-2H-pyrazole-3-amino)-pyrimidin-2-yl-thio]-phenyl}-urea 1-benzo[b]thien-2-yl-3-{3-methyl-4-[4-methyl-6-(5-methyl-2H-pyrazole-3-amino)-pyrimidin-2-yl-thio]-phenyl}-urea Cyclopentyl-3-{3-methyl-4-[4-methyl-6-(5-methyl-2H-pyrazole-3-amino)-pyrimidin-2-yl-thio]-phenyl}-urea 1-cyclobutyl-3-{3-methyl-4-[4-methyl-6-(5-methyl-2H-pyrazole-3-amino)-pyrimidin-2-yl-thio]-phenyl}-urea When $R_2=R_3=CH_3$, $K=S$, $X=O$, and A is phenyl, the compounds derived from varying $R_1$ and $R_4$ are:

1-(4-chloro-3-trifluoromethyl-phenyl-3-{4-[4 (5-isopropyl-2H-pyrazole-3-amino)-6-methyl-pyrimidin-2-yl-thio]-3-methyl-phenyl}-urea 1-(4-chloro-phenyl)-3-{4-[4 (5-chloro-2H-pyrazole-3-amino)-6-methyl-pyrimidin-2-yl-thio]-3-methyl-phenyl}-urea 1-{4-[4-(5-ethyl-2H-pyrazole-3-amino)-6-methyl-pyrimidin-2-yl-thio]-3-methy-phenyl}-3-m-tolyl-urea 5-(2-(4-[3-{3,4-dichloro-phenyl}-ureido]-2-methyl-phenyl-thio}-6-methyl-pyrimidine-4-amino)-1H-pyrazole-3-formic acid 1-(4-isopropyl-phenyl)-3-{3-methyl-4-[4-methyl-6-(5-oxo-5H-pyrazole-3-amino)-pyrimidin-2-yl-thio]-phenyl}-urea 1-{4-[4-(5-acetyl-2H-pyrazole-3-amino)-6-methyl-pyrimidin-2-yl-thio]-3-methyl-phenyl}-3-benzol[1,3]dioxolan-5-yl-urea 5-{6-methyl-2-[2-methyl-4-(3-pyrid-4-yl-ureido)-phenyl-thio]-pyrimidine-4-amino}-1H-pyrazole-3-formamide 1-(3-chloro-4-fluoro-phenyl)-3-{3-methyl-4-[4-methyl-6-(5-nitro-2H-pyrazole-3-amino)-pyrimidin-2-yl-thio]-phenyl}-urea 1-{3-methyl-4-[4-methyl-6-(5-phenyl-2H-pyrazole-3-amino)-pyrimidin-2-yl-thio]-phenyl}-3-pyrimidin-5-yl-urea 1-(3-hydroxy-phenyl)-3-{3-methyl-4-[4-methyl-6-(5-methyl-thio-2H-pyrazole-3-amino)-pyrimidin-2-yl-thio]-phenyl}-urea 4 (3-{4-[4-(5-methoxy-2H-pyrazole-3-amino)-6-methyl-pyrimidin-2-yl-thio]-3-methyl-phenyl}-ureido)-benzoic acid 1-{4-[4-(5-bromo-2H-pyrazole-3-amino)-6-methyl-pyrimidin-2-yl-thio]-3-methyl-phenyl}-3-(3,5-dihydroxy-phenyl)-urea 1-{4-[4-(5-amino-2H-pyrazole-3-amino)-6-methyl-pyrimidin-2-yl-thio]-3-methyl-phenyl}-3-(6-oxo-1,6-dihydro-pyrid-3-yl)-urea Cyclohexyl-3-{4-[4-(5-furan-2-yl-2H-pyrazole-3-amino)-6-methyl-pyrimidin-2-yl-thio]-3-methyl-phenyl}-urea 1-tertbutyl-3-{4-[4 (5-tertbutyl-2H-pyrazole-3-amino)-6-methyl-pyrimidin-2-yl-thio]-3-methyl-phenyl}-urea 1-{4-[4-(5-cyclopropyl-2H-pyrazole-3-amino)-6-methyl-pyrimidin-2-yl-thio]-3-methyl-phenyl}-3-(tetrahydropyran-4-yl)-urea {4-[4-(5-cyclobutyl-2H-pyrazole-3-amino)-6-methyl-pyrimidin-2-yl-thio]-3-methyl-phenyl}-urea 1-(3H-imidazol-4-yl)-3-{3-methyl-4-[4-methyl-6-(5-thien-2-yl-2H-pyrazole-3-amino)-pyrimidin-2-yl-thio]-phenyl}-urea 1-(3-methyl-4-{4-methyl-6-[5-(1H-pyrrol-2-yl)-2H-pyrazole-3-amino]-pyrimidin-2-yl-thio}-phenyl)-3-thiazol-5-yl-urea 1-{4-[4-(5-cyano-2H-pyrazole-3-amino)-6-methyl-pyrimidin-2-yl-thio]-3-methyl-phenyl}-3-(3-nitro-phenyl)-urea 5-(6-methyl-2-[2-methyl-4-(3-quinolin-8-yl-ureido)-phenyl-thio]-pyrimidine-4-amino)-1H-pyrazole-3-carboximidic acid methyl ester Methyl-3-{3-methyl-4-[4-methyl-6-(2H-pyrazole-3-amino)-pyrimidin-2-yl-thio]-phenyl}-urea 1-{4-[4-(5-fluoro-2H-pyrazole-3-amino)-6-methyl-pyrimidin-2-yl-thio]-3-methyl-phenyl-3-(3-methyl-thio-phenyl}-urea 1-{4-[4-(5-ethoxy-2H-pyrazole-3-amino)-6-methyl-pyrimidin-2-yl-thio]-3-methyl-phenyl}-3-piperid-4-yl-urea 1-{4-[4-(5-hydroxy-2H-pyrazole-3-amino)-6-methyl-pyrimidin-2-yl-thio]-3-methyl-phenyl}-3-(1-methyl-piperid-4-yl)-urea 5-(2-{4-[3-(1-acetyl-piperid-4-yl)-ureido]-2-methyl-phenyl-thio}-6-methyl-pyrimidine-4-amino)-1H-pyrazol-3-yl acetate Ethyl 5-{2-[4-(3-butyl-ureido)-2-methyl-phenyl-thio]-6-methyl-pyrimidine-4-amino}-H-pyrazole-3-formate N-[5-(2-(4-[3-(1H-benzoimidazol-5-yl)-ureido]-2-methyl-phenyl-thio)-6-methyl-pyrimidine-4-amino)-1H-pyrazol-3-yl]-acetamide 2-benzyl-3-(3-{4-[4-(5-formamidinyl-2H-pyrazole-3-amino)-6-methyl-pyrimidin-2-yl-thio]-3-methyl-phenyl}-ureido)-3-oxo-propionic acid 1-(4-{4-[5-(1-hydroxy-ethyl)-2H-pyrazole-3-amino]-6-methyl-pyrimidin-2-yl-thio}-3-methyl-phenyl)-3-thien-2-yl-urea Furan-2-yl-3-{3-methyl-4-[4-methyl-6-(5-morpholin-4-yl-2H-pyrazole-3-amino)-pyrimidin-2-yl-thio]-phenyl}-urea 1-{4-[4-(5-dimethylamino-2H-pyrazole-3-amino)-6-methyl-pyrimidin-2-yl-thio]-3-methyl-phenyl}-3-(1-methyl-1H-pyrrol-2-yl)-urea Benzofuran-2-yl-3-{4-[4-(5-ethynyl-2H-pyrazole-3-amino)-6-methyl-pyrimidin-2-yl-thio]-3-methyl-phenyl}-urea Benzo[b]thien-2-yl-3-{3-methyl-4-[4-methyl-6-(5-vinyl-2H-pyrazole-3-amino)-pyrimidin-2-yl-thio]-phenyl}-urea Cyclopentyl-3-{3-methyl-4-[4-methyl-6-(5-piperazin-1-yl-2H-pyrazole-3-amino)-pyrimidin-2-yl-thio]-phenyl}-urea 1-cyclobutyl-3-{3-methyl-4-[4-methyl-6-(5'-methyl-1H,2'H-[3,3']-dipyrazolyl-5-amino)-pyrimidin-2-yl-thio]-phenyl}-urea When $R_2=CH_3$, $R_3=CF_3$, $K=X=O$, and A is phenyl, the compounds derived from varying $R_1$ and $R_4$ are:

1-(4-chloro-3-trifluoromethyl-phenyl)-3-{4-[4 (5-isoprpyl-2H-pyrazole-3-amino)-6-methyl-pyrimidin-2-yl-oxy]-3-trifluoromethyl-phenyl}-urea 1-(4-chloro-phenyl)-3-{4-[4 (5-chloro-2H-pyrazole-3-amino)-6-methyl-pyrimidin-2-yl-oxy]-3-trifluoromethyl-phenyl}-urea 1-{4-[4-(5-ethyl-2H-pyrazole-3-amino)-6-methyl-pyrimidin-2-yl-oxy]-3-trifluoromethyl-phenyl}-3-m-tolyl-urea 5-(2-{4-[3-(3,4-dichloro-phenyl)-ureido]-2-trifluoromethyl-phenoxy}-6-methyl-pyrimidine-4-amino)-1H-pyrazole-3-formic acid 1-(4-isopropyl-phenyl)-3-{4-[4-methyl-6-(5-oxo-5H-pyrazole-3-amino)-pyrimidin-2-yl-oxy]-3-trifluoromethyl-phenyl}-urea 1-{4-[4-(5-acetyl-2H-pyrazole-3-amino)-6-methyl-pyrimidin-2-yl-oxy]-3-trifluoromethyl-phenyl}-3-benzol[1,3]dioxolan-5-yl-urea 5-{6-methyl-2-[4-(3-pyrid-4-yl-ureido)-2-trifluoromethyl-phenoxy]-pyrimidine-4-amino}-1H-pyrazole-3-formamide 1-(3-chloro-4-fluoro-phenyl)-3-{4-[4-methyl-6-(5-nitro-2H-pyrazole-3-amino)-pyrimidin-2-yl-oxy]-3-trifluoromethyl-phenyl}-urea 1-{4-[4-methyl-6-(5-phenyl-2H-pyrazole-3-amino)-pyrimidin-2-yl-oxy]-3-trifluoromethyl-phenyl}-3-pyrimidin-5-yl-urea 1-(3-hydroxy-phenyl)-3-{4-[4-methyl-6-(5-methyl-thio-2H-pyrazole-3-amino)-pyrimidin-2-yl-oxy]-3-trifluoromethyl-phenyl}-urea 4 (3-[4-[4-(5-methoxy-2H-pyrazole-3-amino)-6-methyl-pyrimidin-2-yl-oxy]-3-trifluorometh yl-phenyl]-ureido)-benzoic acid 1-{4-[4-(5-bromo-2H-pyrazole-3-amino)-6-methyl-pyrimidin-2-yl-oxy]-3-trifluoromethyl-phenyl}-3-{3,5-dihydroxy-phenyl}-urea 1-{4-[4-(5-amino-2H-pyrazole-3-amino)-6-methyl-pyrimidin-2-yl-oxy]-3-trifluoromethyl-phenyl}-3-(6-oxo-1,6-dihydro-pyrid-3-yl)-urea 1-cyclohexyl-3-{4-[4-(5-furan-2-yl-2H-pyrazole-3-amino)-6-methyl-pyrimidin-2-yl-oxy]-3-trifluormmethyl-phenyl}-urea Tertbutyl-3-{4-[4-(5-tertbutyl-2H-pyrazole-3-amino)-6-methyl-pyrimidin-2-yl-oxy]-3-trifluoromethyl-phenyl}-urea 1-{4-[4-(5-cyclopropyl-2H-pyrazole-3-amino)-6-methyl-pyrimidin-2-yl-oxy]-3-trifluoromethyl-phenyl}-3-(tetrahydro-pyran-4-yl)-urea {4-[4-(5-cyclobutyl-2H-pyrazole-3-amino)-6-methyl-pyrimidin-2-yl-oxy]-3-trifluoromethyl-phenyl}-urea 1-(3H-imidazol-4-yl)-3-{4-[4-methyl-6-(5-thien-2-yl-2H-pyrazole-3-amino)-pyrimidin-2-yl-oxy]-3-trifluormmethyl-phenyl}-urea 1-(4-{4-methyl-6-[5-(1H-pyrrol-2-yl)-2H-pyrazole-3-amino]-pyrimidin-2-yl-oxy}-3-trifluoromethyl-phenyl)-3-thiazol-5-yl-urea 1-{4-[4-(5-cyano-2H-pyrazole-3-amino)-6-methyl-pyrimidin-2-yl-oxy]-3-trifluoromethyl-phenyl}-3-{3-nitro-phenyl}-urea 5-{6-methyl-2-[4-(3-quinolin-8-yl-ureido)-2-trifluoromethyl-phenoxy]-pyrimidine-4-amino}-1H-pyrazole-3-carboximidic acid methyl ester 1-methyl-3-{4-[4-methyl-6-(2H-pyrazole-3-amino)-pyrimidin-2-yl-oxy]-3-trifluoromethyl-phenyl}-urea 1-{4-[4-(5-fluoro-2H-pyrazole-3-amino)-6-methyl-pyrimidin-2-yl-oxy]-3-trifluoromethyl-phenyl}-3-(3-methyl-thio-phenyl)-urea 1-{4-[4-(5-ethoxy-2H-pyrazole-3-amino)-6-methyl-pyrimidin-2-yl-oxy]-3-trifluoromethyl-phenyl}-3-piperid-4-yl-urea 1-{4-[4-(5-hydroxy-2H-pyrazole-3-amino)-6-methyl-pyrimidin-2-yl-oxy]-3-trifluoromethyl-phenyl}-3-(1-methyl-piperid-4-yl)-urea 5-(2-{4-[3-(1-acetyl-piperid-4-yl)-ureido]-2-trifluoromethyl-phenoxy}-6-methyl-pyrimidin-4-amino)-1H-pyrazol-3-yl acetate Ethyl 5-{2-[4-(3-butyl-ureido)-2-trifluoromethyl-phenoxy]-6-methyl-pyrimidin-4-amino}-1H-pyrazole-3-formate N-[5-(2-{4-[3-(1 H-benzoimidazol-5-yl)-ureido]-2-trifluoromethyl-phenoxy}-6-methyl-pyrimidine-4-amino)-1H-pyrazol-3-yl]-acetamide 2-benzyl-3-(3-{4-[4-(5-formamidinyl-2H-pyrazole-3-amino)-6-methyl-pyrimidin-2-yl-oxy]-3-trifluoromethyl-phenyl}-ureido)-3-oxo-propionic acid 1-(4-{4-[5-(1-hydroxy-ethyl)-2H-pyrazole-3-amino]-6-methyl-pyrimidin-2-yl-oxy}-3-trifluoromethyl-phenyl)-3-thien-2-yl-urea 1-furan-2-yl-3-{4-[4-methyl-6-(5-morpholin-4-yl-2H-pyrazole-3-amino)-pyrimidin-2-yl-oxy]-3-trifluoromethyl-phenyl}-urea 1-{4-[4-(5-dimethylamino-2H-pyrazol-3-amino)-6-methyl-pyrimidin-2-yl-oxy]-3-trifluoromethyl-phenyl}-3-(1-methyl-1H-pyrrol-2-yl)-urea 1-benzofuran-2-yl-3-{4-[4-(5-ethynyl-2H-pyrazole-3-amino)-6-methyl-pyrimidin-2-yl-oxy]-3-trifluoromethyl-phenyl}-urea 1-benzol[b]thien-2-yl-3-{4-[4-methyl-6-(5-vinyl-2H-pyrazole-3-amino)-pyrimidin-2-yl-oxy]-3-trifluoromethyl-phenyl}-urea 1-cyclopentyl-3-{4-[4-methyl-6-(5-piperazin-1-yl-2H-pyrazole-3-amino)-pyrimidin-2-yl-oxy]-3-trifluoromethyl-phenyl}-urea 1-cyclobutyl-3-{4-[4-methyl-6-(5'-methyl-1H,2'H-[3,3']-dipyrazolyl-5-amino)-pyrimidin-2-yl-oxy]-3-trifluoromethyl-phenyl}-urea When $R_2$=CH$_3$, $R_3$=Cl, K=X=O, and A is phenyl, the compounds derived from varying $R_1$ and $R_4$ are:

1-{3-chloro-4-[4-(5-isopropyl-2H-pyrazole-3-amino)-6-methyl-pyrimidin-2-yl-oxy]-phenyl}-3-(4-chloro-3-trifluoromethyl-phenyl)-urea 1-{3-chloro-4-[4-(5-chloro-2H-pyrazole-3-amino)-6-methyl-pyrimidin-2-yl-oxy]-phenyl-3-(4-chloro-phenyl}-urea 1-{3-chloro-4-[4-(5-ethyl-2H-pyrazole-3-amino)-6-methyl-pyrimidin-2-yl-oxy]-phenyl}-3-m-tolyl-urea 5-(2-{2-chloro-4-[3-(3,4-dichloro-phenyl)-ureido]-phenoxy}-6-methyl-pyrimidine-4-amino)-1H-pyrazole-3-formic acid 1-{3-chloro-4-[4-methyl-6-(5-oxo-5H-pyrazole-3-amino)-pyrimidin-2-yl-oxy]-phenyl}-3-(4-isopropyl-phenyl)-urea 1-{4-[4-(5-acetyl-2H-pyrazole-3-amino)-6-methyl-pyrimidin-2-yl-oxy]-3-chloro-phenyl}-3-benzol[,3]dioxolan-5-yl-urea 5-{2-[2-chloro-4-(3-pyrid-4-yl-ureido)-phenoxy]-6-methyl-pyrimidine-4-amino}-1H-pyrazole-3-formamide 1-(3-chloro-4-fluoro-phenyl)-3-{3-chloro-4-[4-methyl-6-(5-nitro-2H-pyrazole-3-amino)-pyrimidin-2-yl-oxy]-phenyl}-urea 1-{3-chloro-4-[4-methyl-6-(5-phenyl-2H-pyrazole-3-amino)-pyrimidin-2-yl-oxy]-phenyl}-3-pyrimidin-5-yl-urea 1-(3-chloro-4-[4-methyl-6-(5-methyl-thio-2H-pyrazole-3-amino)-pyrimidin-2-yloxy-phenyl]-3-{3-hydroxy-phenyl}-urea 4-(3-{3-chloro-4-[4-(5-methoxy-2H-pyrazole-3-amino)-6-methyl-pyrimidin-2-yl-oxy]-phenyl}-ureido)-benzoic acid 1-{4-[4-(5-bromo-2H-pyrazole-3-amino)-6-methyl-pyrimidin-2-yl-oxy]-3-chloro-phenyl}-3-(3,5-dihydroxy-phenyl)-urea 1-{4-[4-(5-amino-2H-pyrazole-3-amino)-6-methyl-pyrimidin-2-yl-oxy]-3-chloro-phenyl}-3-(6-oxo-1,6-dihydro-pyrid-3-yl)-urea 1-{3-chloro-4-[4-(5-furan-2-yl-2H-pyrazole-3-amino)-6-methyl-pyrimidin-2-yl-oxy]-phenyl}-3-cyclohexyl-urea 1-tertbutyl-3-{4-[4-(5-tertbutyl-2H-pyrazole-3-amino)-6-methyl-pyrimidin-2-yl-oxy]-3-chloro-phenyl}-urea 1-(3-chloro-4-[4-(5-cyclopropyl-2H-pyrazole-3-amino)-6-methyl-pyrimidin-2-yl-oxy-phenyl]-3-(tetrahydropyran-4-yl)-urea {3-chloro-4-[4 (5-cyclobutyl-2H-pyrazole-3-amino)-6-methy-pyrimidin-2-yl-oxy]-phenyl}-urea 1-{3-chloro-4-[4-methyl-6-(5-thien-2-yl-2H-pyrazole-3-amino)-pyrimidin-2-yl-oxy]-phenyl}-3-(3H-imidazol-4-yl)-urea 1-(4-{4-methyl-6-[5-(1H-pyrrol-2-yl)-2H-pyrazole-3-amino]-pyrimidin-2-yl-oxy}-3-trifluoromethyl-phenyl)-3-thiazol-5-yl-urea 1-{3-chloro-4-[4-(5-cyano-2H-pyrazole-3-amino)-6-methyl-pyrimidin-2-yl-oxy]-phenyl}-3-(3-nitro-phenyl)-urea
5-(2-[2-chloro-4-(3-quinolin-8-yl-ureido)-phenoxy]-6-methyl-pyrimidine-4-amino)-1H-pyrazole-3-carboximidic acid methyl ester
1-{3-chloro-4-[4-methyl-6-(2H-pyrazole-3-amino)-pyrimidin-2-yl-oxy]-phenyl}-3-methyl-urea
1-{3-chloro-4-[4-(5-fluoro-2H-pyrazole-3-amino)-6-methyl-pyrimidin-2-yl-oxy]-phenyl}-3-(3-methyl-thio-phenyl)-urea
1-{3-chloro-4-[4-(5-ethoxy-2H-pyrazole-3-amino)-6-methyl-pyrimidin-2-yl-oxy]-phenyl}-3-piperid-4-yl-urea
1-{3-chloro-4-[4-(5-hydroxy-2H-pyrazole-3-amino)-6-methyl-pyrimidin-2-yl-oxy]-phenyl}-3-(1-methyl-piperid-4-yl)-urea
5-(2-{4-[3-(1-acetyl-piperid-4-yl)-ureido]-2-chloro-phenoxy}-6-methyl-pyrimidine-4-amino)-1H-pyrazol-3-yl acetate
Ethyl 5-{2-[4-(3-butyl-ureido)-2-chloro-phenoxy]-6-methyl-pyrimidine-4-amino}-1H-pyrazole-3-formate
N-[5-(2-{4-[3-(1H-benzoimidazol-5-yl)-ureido]-2-chloro-phenoxy}-6-methyl-pyrimidine-4-amino)-1H-pyrazol-3-yl]-acetamide
3-(3-{4-[4-(5-formamidinyl-2H-pyrazole-3-amino)-6-methyl-pyrimidin-2-yl-oxy]-3-chloro-phenyl}-ureido)-3-oxy-2-pyrid-4-yl-methyl-propionic acid
1-{3-chloro-4-(4-[5-(1-hydroxy-ethyl)-2H-pyrazole-3-amino]-6-methyl-pyrimidin-2-yl-oxy}-phenyl)-3-thien-2-yl-urea
1-{3-chloro-4-[4-methyl-6-(5-morpholin-4-yl-2H-pyrazole-3-amino)-pyrimidin-2-yl-oxy]-phenyl}-3-furan-2-yl-urea
1-{3-chloro-4-[4-(5-dimethylamino-2H-pyrazole-3-amino)-6-methyl-pyrimidin-2-yl-oxy]-3-phenyl}-3-(1-methyl-1H-pyrrol-2-yl)-urea
1-benzofuran-2-yl-3-{3-chloro-4-[4-(5-ethynyl-2H-pyrazole-3-amino)-6-methyl-pyrimidin-2-yl-oxy]-phenyl}-urea
1-benzol[b]thien-2-yl-3-{3-chloro-4-[4-methyl-6-(5-vinyl-2H-pyrazole-3-amino)-pyrimidin-2-yl-oxy]-phenyl}-urea
1-{3-chloro-4-[4-methyl-6-(5-piperazin-1-yl-2H-pyrazole-3-amino)-pyrimidin-2-yl-oxy]-phenyl}-3-cyclopentyl-urea
1-{3-chloro-4-[4-methyl-6-(5'-trifluoromethyl-1H,2'H-[3,3']-dipyrazolyl-5-amino)-pyrimidin-2-yl-oxy]-phenyl}-3-cyclobutyl-urea When $R_2$=CH$_3$, $R_3$=OMe, K=X=O, and A is phenyl, the compounds derived from varying $R_1$ and $R_4$ are:
1-(4-chloro-3-trifluoromethyl-phenyl-4-{4-[4 (5-isopropyl-2H-pyrazole-3-amino)-6-methyl-pyrimidin-2-yl-oxy]-3-methoxy-phenyl}-urea
1-(4-chlor-phenyl)-3-{4-[4 (5-chloro-2H-pyrazole-3-amino)-6-methyl-pyrimidin-2-yl-oxy]-3-methoxy-phenyl}-urea
1-{4-[4-(5-ethyl-2H-pyrazole-3-amino)-6-methyl-pyrimidin-2-yl-oxy]-3-methoxy-phenyl}-3-m-tolyl-urea
5-(2-(4-[3-{3,4-dichloro-phenyl)-ureido]-2-methoxy-phenoxy}-6-methyl-pyrimidine-4-amino)-1H-pyrazole-3-formic acid
1-(4-isopropyl-phenyl)-3-{3-methoxy-4-[4-methyl-6-(5-oxo-5H-pyrazole-3-amino)-pyrimidin-2-yl-oxy]-phenyl}-urea
1-{4-[4-(5-acetyl-2H-pyrazole-3-amino)-6-methyl-pyrimidin-2-yl-oxy]-3-methoxy-phenyl}-3-benzo[1,3]dioxolan-5-yl-urea
5-{2-[2-methoxy-4-(3-pyrid-4-yl-ureido)-phenoxy]-6-methyl-pyrimidine-4-amino}-1H-pyrazole-3-formamide
(3-chloro-4-fluoro-phenyl)-3-{-3-methoxy-4-[methyl-6-(5-nitro-2H-pyrazole-3-amino)-pyrimidin-2-yl-oxy]-phenyl}-urea
1-{3-methoxy-4-[4-methyl-6-(5-phenyl-2H-pyrazole-3-amino)-pyrimidin-2-yl-oxy]-phenyl}-3-pyrimidin-5-yl-urea
1-(3-hydroxy-phenyl)-3-{3-methoxy-4-[4-methyl-6-(5-methyl-thio-2H-pyrazole-3-amino)-pyrimidin-2-yl-oxy]-phenyl}-urea
4 (3-{3-methoxy-4-[4-(5-methoxy-2H-pyrazole-3-amino)-6-methyl-pyrimidin-2-yl-oxy-phenyl}-ureido)-benzoic acid
1-{4-[4-(5-bromo-2H-pyrazole-3-amino)-6-methyl-pyrimidin-2-yl-oxy]-3-methoxy-phenyl}-3-{3,5-dihydroxy-phenyl}-urea
1-{4-[4-(5-amino-2H-pyrazole-3-amino)-6-methyl-pyrimidin-2-yl-oxy]-3-methoxy-phenyl}-3-(6-oxo-1,6-dihydro-pyrid-3-yl)-urea
1-cyclohexyl-3-{4-[4-(5-furan-2-yl-2H-pyrazole-3-amino)-6-methyl-pyrimidin-2-yl-oxy]-3-methoxy-phenyl}-urea
Tertbutyl-3-{4-[4-(5-tertbutyl-2H-pyrazole-3-amino)-6-methyl-pyrimidin-2-yl-oxy]-3-methoxy-phenyl}-urea
1-{4-[4-(5-cyclopropyl-2H-pyrazole-3-amino)-6-methyl-pyrimidin-2-yl-oxy-3-methoxy-phenyl]-3-(tetrahydropyran-4-yl}-urea
{4-[4-(5-cyclobutyl-2H-pyrazole-3-amino)-6-methyl-pyrimidin-2-yl-oxy]-3-methoxy-phenyl}-urea
1-(3H-imidazol-4-yl)-3-{3-methoxy-4-[4-methyl-6-(5-thien-2-yl-2H-pyrazole-3-amino)-pyrimidin-2-yl-oxy]-phenyl}-urea
1-(3-methoxy-4-{4-methyl-6-[5-(1H-pyrrol-2-yl)-2H-pyrazole-3-amino]-pyrimidin-2-yl-oxy}-phenyl)-3-thiazol-5-yl-urea
1-{4-[4-(5-cyano-2H-pyrazole-3-amino)-6-methyl-pyrimidin-2-yl-oxy]-3-methoxy-phenyl}-3-(3-nitro-phenyl)-urea
5-{2-[2-methoxy-4-(3-quinolin-8-yl-ureido)-phenoxy]-6-methyl-pyrimidine-4-amino}-1H-pyrazole-3-carboximidic acid methyl ester
1-{3-methoxy-4-[4-methyl-6-(2H-pyrazole-3-amino)-pyrimidin-2-yl-oxy]-phenyl}-3-methyl-urea
1-{4-[4-(5-fluoro-2H-pyrazole-3-amino)-6-methyl-pyrimidin-2-yl-oxy]-3-methoxy-phenyl}-3-(3-methyl-thio-phenyl)-urea
1-{4-[4-(5-ethoxy-2H-pyrazole-3-amino)-6-methyl-pyrimidin-2-yl-oxy]-3-methoxy-phenyl}-3-piperid-4-yl-urea
1-{4-[4-(5-hydroxy-2H-pyrazole-3-amino)-6-methyl-pyrimidin-2-yl-oxy]-3-methoxy-phenyl}-3-(1-methyl-piperid-4-yl)-urea
5-(2-{4-[3-(1-acetyl-piperid-4-yl)-ureido]-2-methoxy-phenoxy}-6-methyl-pyrimidine-4-amino)-1H-pyrazol-3-yl acetate
Ethyl 5-{2-[4-(3-butyl-ureido)-2-methoxy-phenoxy]-6-methyl-pyrimidine-4-amino}-1H-pyrazole-3-formate
N-[5-(2-{4-[3-(1H-benzoimidazol-5-yl)-ureido]-2-methoxy-phenoxy}-6-methyl-pyrimidine-4-amino)-1H-pyrazol-3-yl]-acetamide
3-(3-{4-[4-(5-formamidinyl-2H-pyrazole-3-amino)-6-methyl-pyrimidin-2-yl-oxy]-3-methoxy-phenyl}-ureido-3-oxo-2-pyrid-4-yl-methyl-propionic acid
1-(4-{4-[5-(1-hydroxy-ethyl)-2H-pyrazole-3-amino]-6-methyl-pyrimidin-2-yl-oxy}-3-methoxy-phenyl)-3-thien-2-yl-urea 1-furan-2-yl-3-{3-methoxy-4-[4-methyl-6-(5-morpholin-4-yl-2H-pyrazole-3-amino)-pyrimidin-2-yl-oxy]-phenyl}-urea 1-{4-[4-(5-dimethylamino-2H-pyrazole-3-amino)-6-methyl-pyrimidin-2-yl-oxy]-3-methoxy-phenyl}-3-(1-methyl-1H-pyrrol-2-yl)-urea 1-benzofuran-2-yl-3-{4-[4-(5-ethynyl-2H-pyrazole-3-amino)-6-methyl-pyrimidin-2-yl-oxy]-3-methoxy-phenyl}-urea 1-benzo[b]thien-2-yl-3-{3-methoxy-4-[4-methyl-6-(5-vinyl-2H-pyrazole-3-amino)-pyrimidin-2-yl-oxy]-phenyl}-urea Cyclopentyl-3-{3-methoxy-4-[4-methyl-6-(5-piperazin-1-yl-2H-pyrazole-3-amino)-pyrimidin-2-yl-oxy]-phenyl}-urea 1-cyclobutyl-3-{3-methoxy-4-[4-(5'-trifluoromethyl-1H,2'H-[3,3']-dipyrazolyl-5-amino)-pyrimidin-2-yl-oxy]-phenyl}-urea When $R_2$=CH$_3$, $R_3$=H, $R_4$=4-chloro-3-trifluoromethyl-phenyl, K=CH$_2$, X=O, and A is pyridyl, the compounds derived from varying $R_1$ are:

1-(4-chloro-3-trifluoromethyl-phenyl)-3-{5-[4 (5-isopropyl-2H-pyrazole-3-amino)-6-methyl-pyrimidin-2-yl-methyl]-pyrid-2-yl}-urea 1-{5-[4-(5-chloro-2H-pyrazole-3-amino)-6-methyl-pyrimidin-2-yl-methyl]-pyrid-2-yl}-3-(4-chloro-trifluoromethyl-phenyl)-urea 1-(4-chloro-3-trifluoromethyl-phenyl)-3-{5-[4-(5-ethyl-2H-pyrazole-3-amino)-6-methyl-pyrimidin-2-yl-methyl]-pyrid-2-yl}-urea 5-(2-{6-[3-(4-chloro-3-trifluoromethyl-phenyl)-ureido]-pyrid-3-yl-methyl}-6-methy-pyrimidine-4-amino)-1H-pyrazole-3-formic acid 1-(4-chloro-3-trifluoromethyl-phenyl)-3-{5-[4-methyl-6-(5-oxo-5H-pyrazole-3-amino)-pyrimidin-2-yl-methyl]-pyrid-2-yl}-urea 1-{5-[4-(5-acetyl-2H-pyrazole-3-amino)-6-methyl-pyrimidin-2-yl-methyl]-pyrid-2-yl}-3-(4-chloro-3-trifluoromethyl-phenyl)-urea 5-(2-{6-[3-(4-chloro-3-trifluoromethyl-phenyl)-ureido]-pyrid-3-yl-methyl}-6-methy-pyrimidine-4-amino)-1H-pyrazole-3-formamide 1-(4-chloro-3-trifluoromethyl-phenyl)-3-{5-[4-methyl-6-(5-nitro-2H-pyrazole-3-amino)-pyrimidin-2-yl-methyl]-pyrid-2-yl}-urea 1-(4-chloro-3-trifluoromethyl-phenyl)-3-{5-[4-methyl-6-(5-phenyl-2H-pyrazole-3-amino)-pyrimidin-2-yl-methyl]-pyrid-2-yl}-urea 1-(4-chloro-3-trifluoromethyl-phenyl)-3-{5-[4-methyl-6-(5-methyl-thio-2H-pyrazole-3-amino)-pyrimidin-2-yl-methyl]-pyrid-2-yl}-urea 1-(4-chloro-3-trifluoromethyl-phenyl)-3-{5-[4-(5-methoxy-2H-pyrazole-3-amino)-6-methyl-pyrimidin-2-yl-methyl]-pyrid-2-yl}-urea 1-{5-[4-(5-bromo-2H-pyrazole-3-amino)-6-methyl-pyrimidin-2-yl-methyl]-pyrid-2-yl}-3-(4-chloro-3-trifluoromethyl-phenyl)-urea 1-{5-[4-(5-amino-2H-pyrazole-3-amino)-6-methyl-pyrimidin-2-yl-methyl]-pyrid-2-yl}-3-(4-chloro-3-trifluoromethyl-phenyl)-urea 1-(4-chloro-3-trifluoromethyl-phenyl)-3-{5-[4-(5-furan-2-yl-2H-pyrazole-3-amino)-6-methyl-pyrimidin-2-yl-methyl]-pyrid-2-yl}-urea 1-{5-[4-(5-tertbutyl-2H-pyrazole-3-amino)-6-methyl-pyrimidin-2-yl-methyl]-pyrid-2-yl}-3-(4-chloro-3-trifluoromethyl-phenyl)-urea 1-(4-chloro-3-trifluoromethyl-phenyl)-3-{5-[4-(5-cyclopropyl-2H-pyrazole-3-amino)-6-methyl-pyrimidin-2-yl-methyl]-pyrid-2-yl}-urea 1-(4-chloro-3-trifluoromethyl-phenyl)-3-{5-[4-(5-cyclobutyl-2H-pyrazole-3-amino)-6-methyl-pyrimidin-2-yl-methyl]-pyrid-2-yl}-urea 1-(4-chloro-3-trifluoromethyl-phenyl)-3-{5-[4-methyl-6-(5-thien-2-yl-2H-pyrazole-3-amino)-pyrimidin-2-yl-methyl]-pyrid-2-yl}-urea 1-(4-chloro-3-trifluoromethyl-phenyl)-3-(5-{4-methyl-6-[5-(1H-pyrrol-2-yl)-2H-pyrazole-3-amino]-pyrimidin-2-yl-methyl}-pyrid-2-yl)-urea 1-(4-chloro-3-trifluoromethyl-phenyl)-3-{5-[4-(5-cyano-2H-pyrazole-3-amino)-6-methyl-pyrimidin-2-yl-methyl]-pyrid-2-yl}-urea 5-(2-{6-[3-(4-chloro-3-trifluoromethyl-phenyl)-ureido]-pyrid-3-yl-methyl}-6-methyl-pyrimidine-4-amino)-1H-pyrazole-3-carboximidic acid methyl ester 1-(4-chloro-3-trifluoromethyl-phenyl)-3-{4-methyl-5-[4-methyl-6-(2H-pyrazole-3-amino)-pyrimidin-2-yl-methyl]-pyrid-2-yl}-urea 1-(4-chloro-3-trifluoromethyl-phenyl)-3-{5-[4-(5-fluoro-2H-pyrazole-3-amino)-6-methyl-pyrimidin-2-yl-methyl]-pyrid-2-yl}-urea 1-(4-chloro-3-trifluoromethyl-phenyl)-3-{5-[4-(5-ethoxy-2H-pyrazole-3-amino)-6-methyl-pyrimidin-2-yl-methyl]-pyrid-2-yl}-urea 1-(4-chloro-3-trifluoromethyl-phenyl)-3-{5-[4-(5-hydroxy-2H-pyrazol 3-yl-methyl)-6-methyl-pyrimidin-2-yl-methyl]-pyrid-2-yl}-urea 5-(2-{6-[3-(4-chloro-3-trifluoromethyl-phenyl)-ureido]-pyridin-3-yl-methyl}-6-methyl-pyrimidin-4-yl-methyl)-1H-pyrazol-3-yl acetate Ethyl 5-(2-{6-[3-(4-chloro-3-trifluoromethyl-phenyl)-ureido]-pyridin-3-yl-methyl}-6-methyl-pyrimidin-4-yl-methyl)-1H-pyrazole-3-formate N-[5-(2-{6-[3-(4-chloro-3-trifluoromethyl-phenyl)-ureido]-pyridin-3-yl-methyl]-6-methyl-pyrimidine-4-amino)-1H-pyrazol-3-yl]-acetamide 5-(2-{6-[3-(4-chloro-3-trifluoromethyl-phenyl)-ureido]-pyridin-3-yl-methyl}-6-methyl-pyrimidine-4-amino)-1H-pyrazol-3-formamidine 1-(4-chloro-3-trifluoromethyl-phenyl)-3-(5-{4-[5-(l-hydroxy-ethyl)-2H-pyrazole-3-amino]-6-methyl-pyrimidin-2-yl-methyl}-pyrid-2-yl)-urea 1-(4-chloro-3-trifluoromethyl-phenyl)-3-{5-[4-methyl-6-(5-morpholin-4-yl-2H-pyrazole-3-amino)-pyrimidin-2-yl-methyl]-pyrid-2-yl}-urea 1-(4-chloro-3-trifluoromethyl-phenyl)-3-{5-[4-(5-dimethylamino-2H-pyrazole-3-amino)-6-methyl-pyrimidin-2-yl-methyl]-pyrid-2-yl}-urea 1-(4-chloro-3-trifluoromethyl-phenyl)-3-{5-[4-(5-ethynyl-2H-pyrazole-3-amino)-6-methyl-pyrimidin-2-yl-methyl]-pyrid-2-yl}-urea 1-(4-chloro-3-trifluoromethyl-phenyl)-3-{5-[4-methyl-6-(5-vinyl-2H-pyrazole-3-amino)-pyrimidin-2-yl-methyl]-pyrid-2-yl}-urea 1-(4-chloro-3-trifluoromethyl-phenyl)-3-{5-[4-methyl-6-(5-piperazin-1-yl-2H-pyrazole-3-amino)-pyrimidin-2-yl-methyl]-pyrid-2-yl}-urea 1-(4-chloro-3-trifluoromethyl-phenyl)-3-{5-[4-methyl-6-(5'-methyl-1H,2'H-[3,3']-dipyrazolyl-5-amino)-pyrimidin-2-yl-methyl]-pyrid-2-yl}-urea When $R_2$=H, $R_3$=CH$_3$, $R_4$=4-chloro-3-trimethyl-phenyl, K=CH$_2$, X=O, and A is phenyl, the compounds derived from varying R, are:

1-(4-chloro-3-trifluoromethyl-phenyl)-3-{4-[4 (5-isopropyl-2H-pyrazole-3-amino)-pyrimidin-2-yl-methyl]-3-methyl-phenyl}-urea 1-{4-[4-(5-chloro-2H-pyrazole-3-amino)-pyrimidin-2-yl-methyl]-3-methyl-phenyl}-3-(4-chloro-3-trifluoromethyl-phenyl)-urea 1-(4-chloro-3-trifluoromethyl-phenyl)-3-{4-[4-(5-ethyl-2H-pyrazole-3-amino)-pyrimidin-2-yl-methyl]-3-methyl-phenyl}-urea 5-(2-{4-[3-(4-chloro-3-trifluoromethyl-phenyl)-ureido]-2-methyl-benzyl}-pyrimidine-4-amino)-1H-pyrazole-3-formic acid 1-(4-chloro-3-trifluoromethyl-phenyl)-3-{3-methyl-4-[4-(5-oxo-5H-pyrazole-3-amino)-pyrimidin-2-yl-methyl]-phenyl}-urea 1-{4-[4-(5-acetyl-2H-pyrazole-3-amino)-pyrimidin-2-yl-methyl]-3-methyl-phenyl}-3-(4-chlor-3-trifluoromethyl-phenyl)-urea 5-(2-{4-[3-(4-chloro-3-trifluoromethyl-phenyl)-ureido]-2-methyl-benzyl}-pyrimidine-4-amino)-1H-pyrazole-3-formamide 1-(4-chloro-3-trifluoromethyl-phenyl)-3-{4-methyl-5-[4-(5-nitro-2H-pyrazole-3-amino)-pyrimidin-2-yl-methyl]-pyrid-2-yl}-urea 1-(4-chloro-3-trifluoromethyl-phenyl)-3-{3-methyl-4-[4 (5-phenyl-2H-pyrazole-3-amino)-pyrimidin-2-yl-methyl]-phenyl}-urea 1-(4-chloro-3-trifluoromethyl-phenyl)-3-{3-methyl-4 [445-methyl-thio-2H-pyrazole-3-amino)-pyrimidin-2-yl-methyl]-phenyl}-urea 1-(4-chloro-3-trifluoromethyl-phenyl)-3-{4-[4-(5-methoxy-2H-pyrazole-3-amino)-pyrimidin-2-yl-methyl]-3-methyl-phenyl}-urea 1-{4-[4-(5-bromo-2H-pyrazole-3-amino)-pyrimidin-2-yl-methyl]-3-methyl-phenyl}-3-(4-chloro-3-trifluoromethyl-phenyl)-urea 1-{4-[4-(5-amino-2H-pyrazole-3-amino)-pyrimidin-2-yl-methyl]-3-methyl-phenyl}-3-(4-chloro-3-trifluoromethyl-phenyl)-urea 1-(4-chloro-3-trifluoromethyl-phenyl)-3-{4-[4-(5-furan-2-yl-2H-pyrazole-3-amino)-pyrimidin-2-yl-methyl]-3-methyl-phenyl}-urea 1-{4-[4-(5-tertbutyl-2H-pyrazole-3-amino)-pyrimidin-2-yl-methyl]-3-methyl-phenyl}3-(4-chloro-3-trifluoromethyl-phenyl)-urea 1-(4-chloro-3-trifluoromethyl-phenyl)-3-{4-[4-(5-cyclopropyl-2H-pyrazole-3-amino)-pyrimidin-2-yl-methyl]-3-methyl-phenyl}-urea 1-(4-chloro-3-trifluoromethyl-phenyl)-3-{4-[4-(5-cyclobutyl-2H-pyrazole-3-amino)-pyrimidin-2-yl-methyl]-3-methyl-phenyl}-urea 1-(4-chloro-3-trifluoromethyl-phenyl)-3-{3-methyl-4-[4-(5-thien-2-yl-2H-pyrazole-3-amino)-pyrimidin-2-yl-methyl]-phenyl}-urea 1-(4-chloro-3-trifluoromethyl-phenyl)-3-(3-methyl-4-{4-[5-(1H-pyrrol-2-yl)-2H-pyrazole-3-amino]-pyridine-2-yl-methyl}-phenyl)-urea 1-(4-chloro-3-trifluoromethyl-phenyl)-3-{4-[4-(5-cyano-2H-pyrazole-3-amino)-pyrimidin-2-yl-methyl]-3-methyl-phenyl}-urea 5-(2-{4-[3-(4-chloro-3-trifluoromethyl-phenyl)-ureido]-2-methyl-benzyl}-pyrimidine-4-amino)-1H-pyrazole-3-carboximidic acid methyl ester 1-(4-chloro-3-trifluoromethyl-phenyl)-3-{4-methyl-5-[4-(2H-pyrazole-3-amino)-pyrimidin-2-yl-methyl]-pyrid-2-yl}-urea 1-(4-chloro-3-trifluoromethyl-phenyl)-3-{5-[4-(5-fluoro-2H-pyrazole-3-amino)-pyrimidin-2-yl-methyl]-pyrid-2-yl}-urea 1-(4-chloro-3-trifluoromethyl-phenyl)-3-{5-[4-(5-ethoxy-2H-pyrazole-3-amino)-b-methyl-pyrimidin-2-yl-methyl]-pyrid-2-yl}-urea 1-(4-chloro-3-trifluoromethyl-phenyl)-3-{5-[4-(5-hydroxy-2H-pyrazole-3-yl-methyl)-pyridin-2-yl-methyl]-pyrid-2-yl}-urea 5-(2-{6-[3-(4-chloro-3-trifluoromethyl-phenyl)-ureido]-pyrimidin-3-yl-methyl}-pyrimidin-4-yl-methyl)-1H-pyrazol-3-yl acetate Ethyl 5-(2-{4-[3-(4-chloro-3-trifluoromethyl-phenyl)-ureido]-benzyl}-pyrimidin-4-yl-methyl)-1 H-pyrazole-3-formate N-[5-(2-{4-[3-(4-chloro-3-trifluoromethyl-phenyl)-ureido]-2-methyl-benzyl}-pyrimidine-4-amino)-1H-pyrazol-3-yl]-acetamide 5-(2-{4-[3-(4-chloro-3-trifluoromethyl-phenyl)-ureido]-2-methyl-benzyl}-pyrimidine-4-amino)-1H-pyrazol-3-formamidine 1-(4-chloro-3-trifluoromethyl-phenyl)-3-{4-(4-[5-(l-hydroxy-ethyl)-2H-pyrazole-3-amino)-pyrimidin-2-yl-methyl]-3-methyl-phenyl}-urea 1-(4-chloro-3-trifluoromethyl-phenyl)-3-{3-methyl-4-[4-(5-morpholin-4-yl-2H-pyrazole-3-amino)-pyrimidin-2-yl-methyl]-phenyl}-urea 1-(4-chloro-3-trifluoromethyl-phenyl)-3-{4-[4-(5-dimethylamino-2H-pyrazole-3-amino)-pyrimidin-2-yl-methyl]-3-methyl-phenyl}-urea 1-(4-chloro-3-trifluoromethyl-phenyl)-3-{4-[4-(5-ethynyl-2H-pyrazole-3-amino)-pyrimidin-2-yl-methyl]-3-methyl-phenyl}-urea 1-(4-chloro-3-trifluoromethyl-phenyl)-3-{3-methyl-4-[4-(5-vinyl-2H-pyrazole-3-amino)-pyrimidin-2-yl-methyl]-phenyl}-urea 1-(4-chloro-3-trifluoromethyl-phenyl)-3-{3-methyl-4-[4-(5-piperazin-1-yl-2H-pyrazole-3-amino)-pyrimidin-2-yl-methyl]-phenyl}-urea 1-(4-chloro-3-trifluoromethyl-phenyl)-3-{3-methyl-4-[4-(5'-methyl-1H,2'H-[3,3']-dipyrazolyl-5-amino)-pyrimidin-2-yl-methyl]-phenyl}-urea Assay for the Inhibiting Activity of Kinase Experimental Reagents: a buffer solution of 25 mM HEPES, 10 mM $MgCl_2$, 0.01% Triton X-100, 100 µg/mL BSA, 2.5 mM DTT, pH=7.4; ATP was available from U.S. Sigma (cat. A7699); Glo Plus Kinase Reagent was available from U.S. Promega (cat. V3773); ADP Glo Reagent was available from U.S. Promega (cat. V9102).

Procedures of the detection experiment for Glo Plus and ADP Glo kinases: the kinase(s), substrate, ATP and the compound(s) to be tested were mixed on a 384-well culture plate, with a total volume of 10 µL of the mixture, reading the values from a plate reader, and then the culture plate was incubated at 30° C. for 1 hour. Test for Glo Plus kinase activity: add 10 µL of Glo Plus kinase per well to the mixture and then incubate at 27° C. for 20 minutes. Test for ADP Glo kinase activity: add 10 µL of ADP Glo per well to the culture plate, and then incubate at 27° C. for 40 minutes. Then a kinase detection reagent (10 µL per well) was added to the culture plate which was incubated at 27° C. for 30 minutes. Read the values from the plate reader to determine inhibition data.

Biologic testing procedures of Caliper kinase: the kinase, substrate, ATP and the compound to be tested were mixed in a 96-well culture plate, with a total volume of 50 µL of the mixture, and then the culture plate was incubated at 30° C. for 1 hour. Add 20 µL of 35 mM EDTA to the culture plate. A solution of 26 μL of the reaction mixture was transferred to a 384-well culture plate, and read the values on a plate reader to determine inhibition data.

Certain compounds has showed preferable activities of inhibiting Aurora A kinase and Raf-1 kinase, please refer to the following table:

TABLE 1

The Inhibiting Activities of Compounds 2, 6, 8, and 9 to Aurora A kinase and Raf-1 kinase

| Compounds | $IC_{50}$ (μM) | |
| --- | --- | --- |
| | Aurora A | Raf-1 |
| 2 | 0.78 | 0.38 |
| 3 | NA | 1.53 |
| 4 | 2.68 | NA |
| 6 | 0.14 | 0.25 |
| 8 | 2.10 | 0.41 |
| 9 | 0.34 | 0.24 |
| 11 | NA | 2.14 |

NA: Not Available

Test for Activity of Inhibiting Tumor Cells

Cytotoxicity is a simple cell killing event caused by cells or chemical substances, and does not depend on the mechanism of cell death of apoptosis or necrosis. Such mechanism can be used to detect the toxicity of certain substance to certain cell (such as the tumor cell), and is thus an important research means in research and development of biopharmaceuticals. The ultimate goal of non-clinical drug research is to predict the clinical efficacy and safety of test materials to determine its accessibility into clinical trials, and to provide a reference for the design of clinical trials and clinically reasonable administration. Therefore, the cytotoxicity test provides sufficient scientific evidences for the research and development of new drugs in the following aspects: 1. estimating starting dose in clinical trials; 2. predicting the clinical indications or target tissues of the test materials; 3. predicting the nature, extent and reversibility of toxicity reactions of the test materials; 4. providing a reference for formulation of the clinical trial programs.

Reagents and consumables: 1. Tumor cells were available from HD Biosciences (Shanghai) Co., Ltd. and detected mycoplasma-free; 2. RPMI 1640 Culture Medium, available from U.S. Invitrogen, Code No.: 31800-022; 3. F12K Culture Medium, available from U.S. Invitrogen, Code No.: 21127-022; 4. DMEM Culture Medium, available from U.S. Invitrogen, Code No.: 12100-046; 5. Fetal bovine serum, available from U.S. Hyclone, Code No.: CH30160.03; 6. Penicillin-Streptomycin liquid, available from U.S. Invitrogen, Code No.: 15140-122; 7. Gemcitabine, available from U.K. Tocris, Code No.: 3259; 8. DMSO, available from U.S. Sigma, Code No.: D4540; 9. 96-well cell culture plate, available from U.S. Corning, Code No.: 3610; 10. CellTiter-Glo Luminescent Cell Viability Assay, available from U.S. Promega, Code No.: G7571; 11. Plate Reader, available from U.S. Perkin Elmer, EnVision Multilabel Plate Reader.

The cell culture mediums: 1. RPMI 1640 whole cell culture medium: a RPMI 1640 culture medium containing 10% fetal bovine serum and 100 U penicillin and 100 μg/mL streptomycin. 2. F12K whole cell culture medium: a F12K culture medium containing 10% fetal bovine serum and 100 U penicillin and 100 μg/mL streptomycin. 3. DMEM whole cell culture medium: a DMEM culture medium containing 10% fetal bovine serum and 100 U penicillin and 100 μg/mL streptomycin.

Preparation of the compounds: 1. A test compound was formulated into a mother liquor in a concentration of 30 mM, and the mother liquor was divided into aliquots and stored in a refrigerator at −80° C. 2. The mother liquors of the test compounds in a concentration of 30 mM were diluted with DMSO to a series of solutions in gradient concentrations, wherein these gradient concentrations included 25 mM, 5 mM, 1 mM, 200 μM, 40 μM, 8 μM, 1.6 μM, 0.32 μM. Then the formulated solutions in gradient concentrations were diluted five times with the whole cell culture mediums, and then the gradient concentrations of the test compounds included 5 mM, 1 mM, 200 μM, 40 μM, 8 μM, 1.6 μM, 0.32 μM, 0.064 μM dissolved in 20% DMSO. 3. Only before the experiments began, the prepared solutions of the test compounds in series of gradient concentrations were diluted one hundred times with the whole cell culture mediums under sterile conditions, wherein these gradient concentrations of the test compounds included 50 μM, 10 μM, 2 μM, 0.4 μM, 0.08 μM, 16 nM, 3.2 nM, 0.64 nM; which were 2× the compound solutions and they could be used to treat the cells. 4. Gemcitabine solutions were subpackaged from 50 mM formulated mother liquors. Use deionized water to formulate a series of solutions in gradient concentrations first, and then use the whole cell mediums to prepare 2× solutions under sterile conditions and they could be used to treat the cells.

Procedures: 1. The tumor cells were inoculated in a 96-well cell culture plate at the day before treating the compounds. The inoculation density was 2000 cell/50 μL/well or 4000 cell/50 μL/well. 2. The second day, the prepared 2× compound solutions were added to the cell culture plate in a concentration of 50 μL per well. 3. The cell plate was gently shaken and placed in an incubator of 37° C. to continue incubating for 72 hours. 4. After finishing incubation, a formulated reagent was added into the cell plate in accordance with the requirements of CellTiter Glo Reagent Instructions and mixed sufficiently before a dark incubation at room temperature for 10 minutes. 5. The cell plate was placed into the plate reader for analysis. Set to read chemiluminescence and record the data.

Data Process: The data read in each well were required to be converted into cell viability. The cell viability could be calculated by using formulae. The treated data would be used to make non-linear regression analysis, to obtain the dose-response curves, and to calculate half growth inhibition concentration ($EC_{50}$) of the test compounds to each cell.

Certain compounds has shown preferable activities as for inhibiting tumor at the cellular level, which are listed in the following table:

TABLE 2

Activities of Compounds 2, and 6 of inhibiting tumor at the cellular level

| Compounds | $EC_{50}$ (μM) | | |
| --- | --- | --- | --- |
| | HepG2 | K562 | A549 |
| 2 | 3.82 | 4.00 | ND |
| 6 | 6.98 | 4.87 | ND |
| 8 | ND | 11.9 | ND |
| 9 | 17.7 | 4.8 | 13.3 |

ND: Not Determined

The invention claimed is:

1. A compound of formula I or a pharmaceutical acceptable salt thereof, a hydrate thereof, or a solvate thereof:

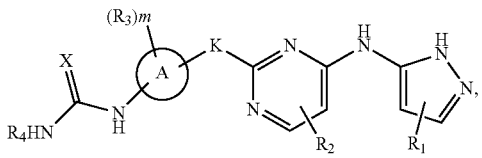

I wherein:
K is NH, O, S, SO, $SO_2$, $CH_2$, C=O or absent;
A is aryl, heterocycloalkyl, cycloalkyl or heteroaryl;
m is an integer of 0 to 4;
X is O, S;
$R_1$ is hydrogen, halogen, —CN, —NO, —$NO_2$, —$NR_9R_{10}$, —$OR_{11}$, —$CO_2R_{12}$, —$SR_{13}$, —$COR_{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein the groups of alkyl, heteroalkyl, cycloalkyl, heterocycloalkyl, aryl, heteroaryl are optionally substituted by $R_{32}$;
$R_{32}$ is halogen, —CN, —$CF_3$, —OH, —$NH_2$, —$SO_2$, —$CO_2H$, alkyl unsubstituted or substituted by $R_{33}$, heteroalkyl unsubstituted or substituted by $R_{33}$, cycloalkyl unsubstituted or substituted by $R_{33}$, heterocycloalkyl unsubstituted or substituted by $R_{33}$, aryl unsubstituted or substituted by $R_{33}$, heteroaryl unsubstituted or substituted by $R_{33}$;
$R_9$, $R_{10}$, $R_{11}$, $R_{12}$, $R_{13}$ and $R_{14}$ are each independently selected from hydrogen, alkyl unsubstituted or substituted by $R_{34}$, heteroalkyl unsubstituted or substituted by $R_{34}$, cycloalkyl unsubstituted or substituted by $R_{34}$, heterocycloalkyl unsubstituted or substituted by $R_{34}$, aryl unsubstituted or substituted by $R_{34}$, heteroaryl unsubstituted or substituted by $R_{34}$;
$R_{34}$ is selected from halogen, —CN, —$CF_3$, —OH, —$NH_2$, —$SO_2$, —$CO_2H$, alkyl unsubstituted or substituted by $R_{35}$, heteroalkyl unsubstituted or substituted by $R_{35}$, cycloalkyl unsubstituted or substituted by $R_{35}$, heterocycloalkyl unsubstituted or substituted by $R_{35}$, aryl unsubstituted or substituted by $R_{35}$, heteroaryl unsubstituted or substituted by $R_{35}$;
$R_{33}$ and $R_{35}$ are each independently selected from halogen, —CN, —$CF_3$, —OH, —$NH_2$, —$SO_2$, —$CO_2H$, unsubstituted alkyl, unsubstituted heteroalkyl, unsubstituted cycloalkyl, unsubstituted heterocycloalkyl, unsubstituted aryl, or unsubstituted heteroaryl;
$R_2$ is amino, alkylamino, arylamino, heteroarylamino, thioalkyl, sulfoxide, sulfone, sulfamoyl, mercapto, halogen, alkoxy, alkanoyl, alkoxycarbonyl, C1-C6 alkyl, C2-C6 alkenyl, cycloalkyl, C2-C6 alkynyl, C5-C7 cycloalkenyl, aryl, heteroaryl, C1-C6 trifluoroalkyl, cyano, wherein each of the substituents is independently substituted by any of 0 to 3 groups selected from halogen, amino, hydroxy, mercapto, nitro or cyano;
$R_2$ is optionally H: (1) when $R_3$ is H, $R_4$ is 4-chloro-3-trifluoromethyl-phenyl, K is NH, X is O or S, and A is pyridyl; (2) when $R_3$ is $CH_3$, $R_4$ is 4-chloro-3-trifluoromethyl-phenyl, K is absent, X is O or S, and A is phenyl; and (3) when $R_3$ is $CH_3$, $R_4$ is 4-chloro-3-triemthyl-phenyl, K is $CH_2$, X is O, and A is phenyl;

$R_3$ is selected from the following substituents:
(i) aryloxy, amino, —NH-alkyl, —N—($R_9$)($R_{10}$), —NH-aryl, —N-(aryl)$_2$, —$NHCOR_9$, —$CO_2H$, —$CO_2$-alkyl, —$CO_2$-aryl, —CONH—$R_9$, —CON—($R_9$)($R_{10}$), —CONH-alkyl, —CON-(alkyl)$_2$, —$SO_3H$, —$SO_2NH_2$, —$CF_3$, —CO—$R_9$ or —CO-aryl, wherein the groups of alkyl, aryl, aryl-substituted alkyl and heterocyclic group are each respectively further substituted by 0 to 3 groups which are selected from halogen, $NO_2$, CN, OH, methoxy, $NH_2$, $CO_2H$, N—($R_9$)($R_{10}$), $CONH_2$, $CHF_2$ and $CF_3$;
(ii) hydrogen, halogen, —CN, —NO, —$NO_2$, —$SO_2NHR_9$, —$CF_2H$, —$OR_{11}$, —$SR_{13}$, —$CH_2CN$, —$CH_2CH_2OH$, —$NHCOCH_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein the groups of alkyl, aryl, heterocycloalkyl and heteroaryl are optionally substituted by 0 to 3 groups which are independently selected from halogen, $NO_2$, CN, OH, methoxy, $NH_2$, $CO_2H$, N—($R_9$)($R_{10}$), $R_{25}$, $CONH_2$ and $CF_3$;
$R_{25}$ is halogen, —CN, —$CF_3$, —OH, —$NH_2$, —$SO_2$, —COOH, —NO, —SH, —$NO_2$, oxo group, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R_4$ is hydrogen, alkyl, heteroalkyl, substituted alkyl, cycloalkyl, aryl, heteroaryl, cycloalkyl, heterocycloalkyl, arylalkyl, heteroarylalkyl, or $COR_5$; wherein the groups of cycloalkyl, aryl, heteroaryl, cycloalkyl-substituted alkyl, heterocycloalkyl, arylalkyl or heteroarylalkyl are independently of each other substituted by 0 to 3 groups which are selected from alkyl, halogen, CN, $NO_2$, $NH_2$, $NHR_5$, $N(R_5)_2$, $SR_5$, heteroalkyl, alkoxy, hydroxy, heteroalkoxy, $CHF_2$, $CF_3$, $OCF_3$, $OCF_2H$; and
$R_5$ is alkyl, heteroalkyl, substituted alkyl, cycloalkyl, aryl, heteroaryl, cycloalkyl, heterocycloalkyl, arylalkyl, heteroarylalkyl, wherein the groups of cycloalkyl, aryl, heteroaryl, cycloalkyl-substituted alkyl, heterocycloalkyl, arylalkyl or heteroarylalkyl are independently of each other substituted by 1 to 3 groups which are selected from aryl, halogen, heteroalkyl, alkoxy, heteroalkoxy.

2. The compound according to claim 1, wherein A is selected from phenyl, naphthyl, and pyrazolyl.

3. The compound according to claim 1, wherein $R_1$ is selected from C1-C10 alkyl unsubstituted or substituted by $R_{32}$, 2-10 membered heteroalkyl unsubstituted or substituted by $R_{32}$, C3-C8 cycloalkyl unsubstituted or substituted by $R_{32}$, and 3-8 membered heterocycloalkyl unsubstituted or substituted by $R_{32}$.

4. The compound according to claim 1, wherein $R_2$ is selected from fluoro, chloro, bromo, methyl, ethyl, trifluoromethyl, trifluoroethyl, and trifluoropropyl.

5. The compound according to claim 1, wherein $R_3$ is selected from alkyl unsubstituted or substituted by $R_{25}$, heteroalkyl unsubstituted or substituted by $R_{25}$, cycloalkyl unsubstituted or substituted by $R_{25}$, heterocycloalkyl unsubstituted or substituted by $R_{25}$, aryl unsubstituted or substituted by $R_{25}$, and heteroaryl unsubstituted or substituted by $R_{25}$.

6. The compound according to claim 1, wherein $R_4$ is aryl substituted by 0 to 3 groups which are selected from alkyl, halogen, CN, $NO_2$, $CHF_2$, $CF_3$, $OCF_3$, $OCF_2H$.

7. The compound according to claim 1, wherein the compound is selected from the following compounds:

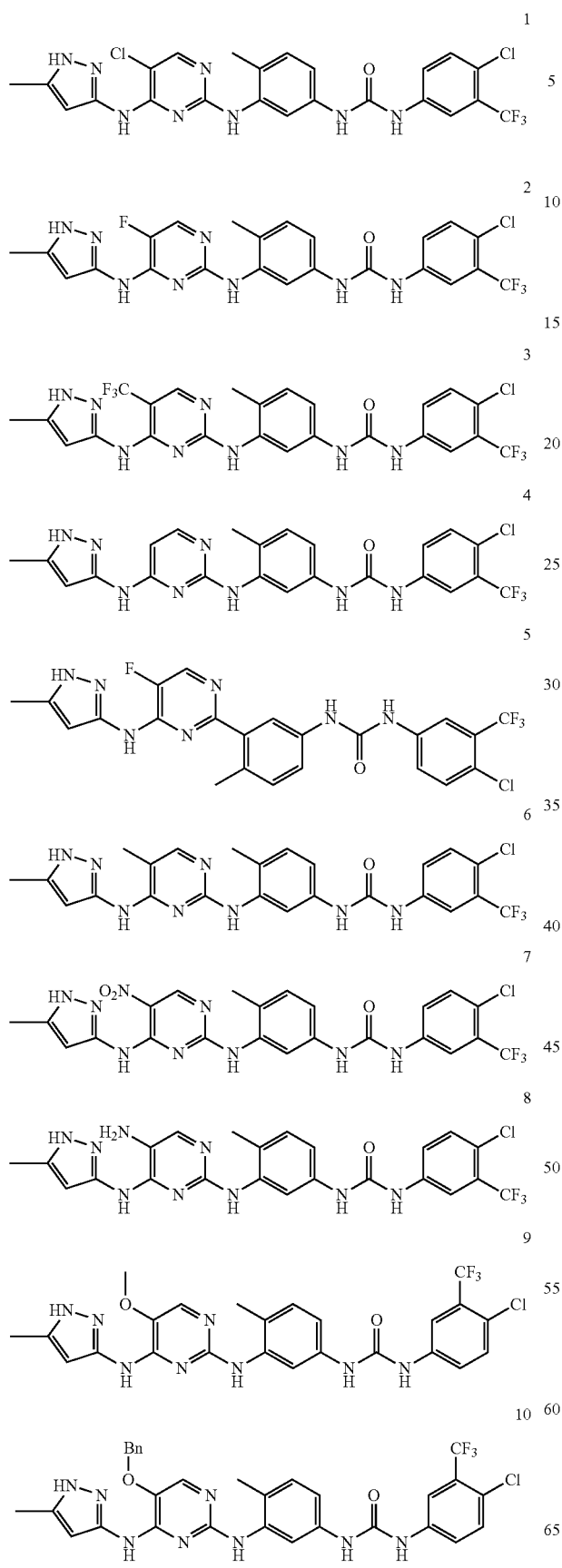

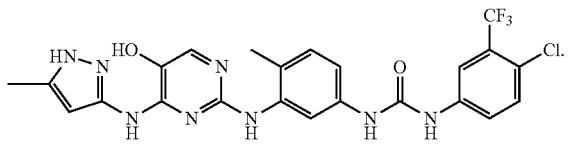

8. A pharmaceutical composition comprising a therapeutically effective amount of compound of claim 1, a pharmaceutical acceptable salt thereof, a hydrate thereof, a solvate thereof.

9. The pharmaceutical composition according to claim 8, wherein the composition is in any acceptable oral-dosed preparation or injectable preparation form.

10. A method for preparing the compound according to claim 1, comprising the following reaction steps:

(a) reacting a dichloropyrimidine derivative having the following structure (a compound of formula II):

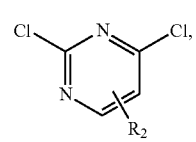

with a heterocyclic amine having the following structure (a compound of formula III):

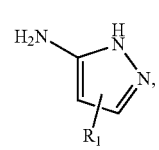

to undergo a substitution reaction to obtain a pyrimidine derivative having the following structure (a compound of formula IV):

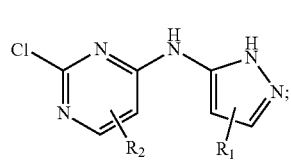

(b) optionally, reacting the pyrimidine derivative (the compound of formula IV) with an amino-protecting agent to obtain a compound of formula V having the following structure:

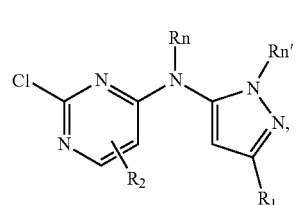

wherein Rn and Rn' are independently of each other H or Boc;

(c) reacting the compound of formula V with a compound of formula VI having the following structure, wherein $R_1'$ is nitro or protected amino, m is an integer of 0 to 4; M is selected from —B(OH)$_2$ or —B(OR)$_2$, R' represents alkyl,

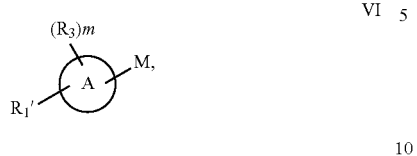

to obtain a compound of formula Vii having the following structure:

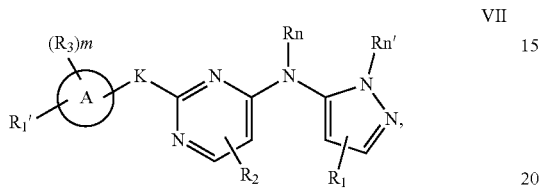

wherein K is NH, O, S, SO, SO$_2$, CH$_2$, C=O or absent;
(d) when $R_1'$ is nitro, the compound of formula VII is subjected to a reduction reaction; alternatively, when $R_1'$ is protected amino, removing the protecting group therein to obtain a compound of formula VIII having the following structure:

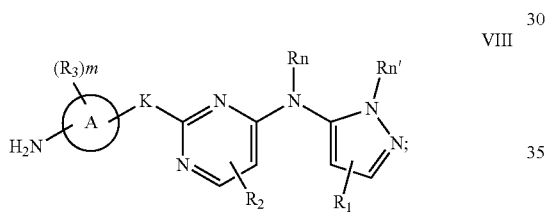

(e) reacting the compound of formula VIII with isocyanate or isothiocyanate to obtain a compound of formula IX having the following structure:

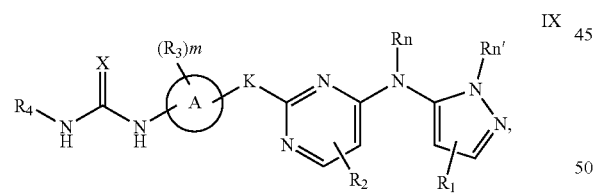

wherein X is O, S;
(f) optionally, the compound of formula (IX) is deprotected under acidic conditions to obtain a compound of formula (I) having the following structure:

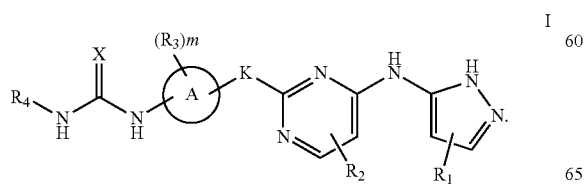

11. A compound of formula IX having the following structure:

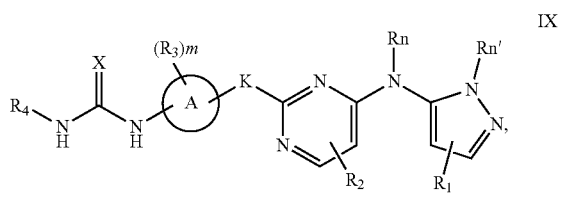

wherein,
K is NH, O, S, SO, SO$_2$, CH$_2$, C=O or absent;
R″ and R‴ are independently H or Boc;
A is aryl, heterocycloalkyl, cycloalkyl or heteroaryl;
m is an integer of 0 to 4;
X is O, S;
$R_1$ is substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
$R_2$ is amino, alkylamino, arylamino, heteroarylamino, thioalkyl, mercapto, halogen, alkoxy, alkanoyl, alkoxycarbonyl, C1-C6 alkyl, C2-C6 alkenyl, cycloalkyl, C2-C6 alkynyl, C5-C7 cycloalkenyl, C1-C6 trifluoroalkyl, cyano, wherein each of the substituents is independently of each other substituted by any of 0 to 3 groups selected from halogen, amino, hydroxy, mercapto, nitro or cyano;
$R_2$ is optionally H when $R_1$ is CH$_3$, R″ is Boc, R‴ is H, K is NH, X is O, A is phenyl, $R_3$ is CH$_3$, M is 1, and $R_4$ is 4-chloro-3-trifluoromethyl-1-phenyl;
$R_3$ is selected from the following substituents:
(i) aryloxy, amino, —NH-alkyl, —NH-aryl, —N-(aryl)$_2$, —CO$_2$H, —CO$_2$-alkyl, —CO$_2$-aryl, —CONH-alkyl, —CON-(alkyl)$_2$, —SO$_3$H, —CF$_3$, —CO—R$_9$ or —CO-aryl, wherein the groups of alkyl, aryl, aryl-substituted alkyl and heterocyclic group are each respectively further substituted by 0 to 3 groups which are preferably selected from halogen, NO$_2$, CN, OH, methoxy, NH$_2$, CO$_2$H, N—(R$_9$)(R$_{10}$), CONH$_2$, CHF$_2$ and CF$_3$;
(ii) hydrogen, halogen, —CN, —NO, —NO$_2$, —SO$_2$NHR$_9$, CF$_2$H, CH$_2$CN, CH$_2$CH$_2$OH, NHCOCH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein the groups of alkyl, aryl, alkyl-substituted aryl and heterocyclic group are optionally substituted by 0 to 3 groups which are independently selected from halogen, NO$_2$, CN, OH, methoxy, NH$_2$, CO$_2$H, N—(R$_9$)(R$_{10}$), R$_{25}$, CONH$_2$ and CF$_3$;
$R_4$ is hydrogen, alkyl, heteroalkyl, substituted alkyl, cycloalkyl, aryl, heteroaryl, cycloalkyl, heterocycloalkyl, arylalkyl, heteroarylalkyl or COR$_5$; wherein the groups of cycloalkyl, aryl, heteroaryl, cycloalkyl-substituted alkyl, heterocycloalkyl, arylalkyl or heteroarylalkyl are independently of each other substituted by 0 to 3 groups which are selected from alkyl, halogen, CN, NO$_2$, NH$_2$, NHR$_5$, N(R$_5$)$_2$, SR$_5$, heteroalkyl, alkoxy, hydroxy, heteroalkoxy, CHF$_2$, CF$_3$, OCF$_3$, OCF$_2$H.

12. The compound according to claim 11, wherein the compound is selected from the following compounds:

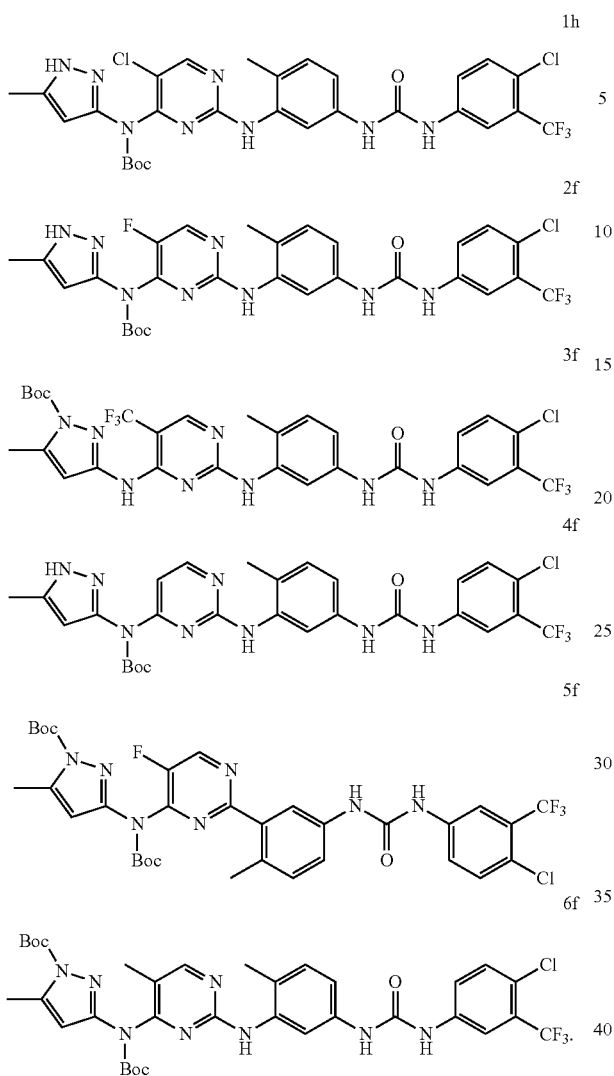

13. A compound of formula VIII having the following structure:

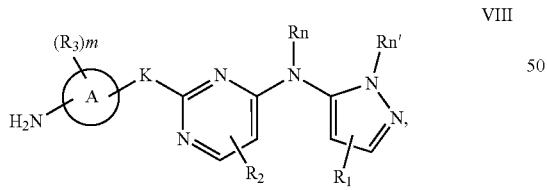

wherein,

K is NH, O, S, SO, SO$_2$, CH$_2$, C=O or absent;

R″ and R″′ are independently H or Boc;

A is aryl, heterocycloalkyl, cycloalkyl or heteroaryl;

m is an integer of 0 to 4;

R$_1$ is substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$_2$ is amino, alkylamino, arylamino, heteroarylamino, thioalkyl, mercapto, halogen, alkoxy, alkanoyl, alkoxycarbonyl, C1-C6 alkyl, C2-C6 alkenyl, cycloalkyl, C2-C6 alkynyl, C5-C7 cycloalkenyl, C1-C6 trifluoroalkyl, cyano, wherein each of the substituents is independently of each other substituted by any of 0 to 3 groups selected from halogen, amino, hydroxy, mercapto, nitro or cyano;

R$_2$ is optionally H when R$_1$ is CH$_3$, R″ is Boc, R″′ is H, K is NH, A is phenyl, R$_3$ is CH$_3$, and m is 1;

R$_3$ is selected from the following substituents:

(i) aryloxy, amino, —NH-alkyl, —NH-aryl, —N-(aryl)$_2$, —CO$_2$H, —CO$_2$-alkyl, —CO$_2$-aryl, —CONH-alkyl, —CON-(alkyl)$_2$, —SO$_3$H, —CF$_3$, —CO—R$_9$ or —CO-aryl, wherein the groups of alkyl, aryl, aryl-substituted alkyl and heterocyclic group are each respectively further substituted by 0 to 3 groups which are preferably selected from halogen, NO$_2$, CN, OH, methoxy, NH$_2$, CO$_2$H, N—(R$_9$)(R$_{10}$), CONH$_2$, CHF$_2$ and CF$_3$;

(ii) hydrogen, halogen, —CN, —NO, —NO$_2$, —SO$_2$NHR$_9$, —CF$_2$H, —CH$_2$CN, —CH$_2$CH$_2$OH, —NHCOCH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein the groups of alkyl, aryl, alkyl-substituted aryl and heterocyclic group are optionally substituted by 0 to 3 groups which are independently selected from halogen, NO$_2$, CN, OH, methoxy, NH$_2$, CO$_2$H, N—(R$_9$)(R$_{10}$), R$_{25}$, CONH$_2$ and CF$_3$.

14. The compound according to claim 13, wherein the compound is selected from the following compounds:

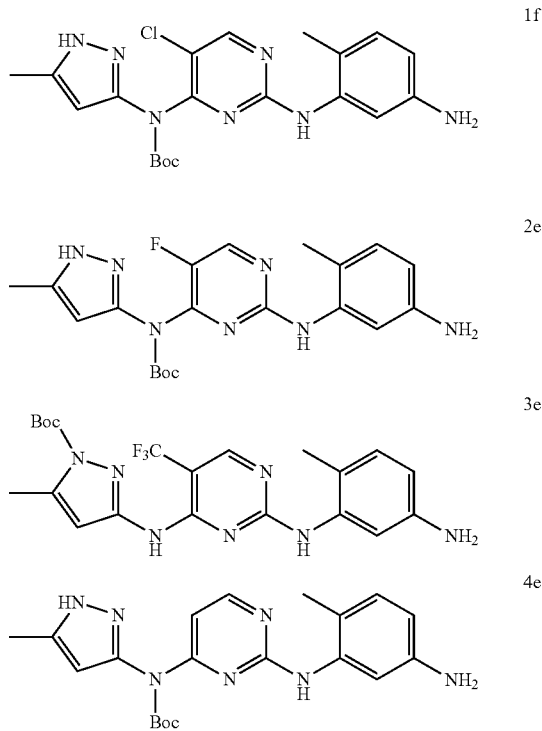

-continued

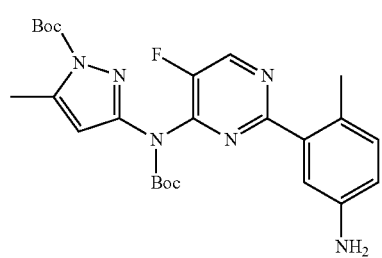
5e

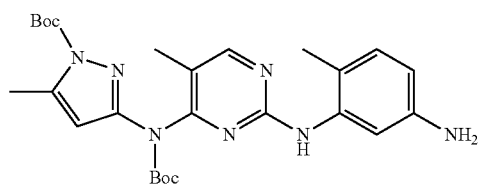
6e

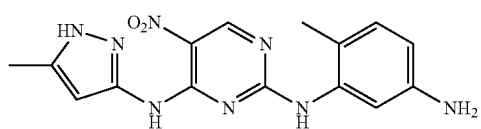
7g

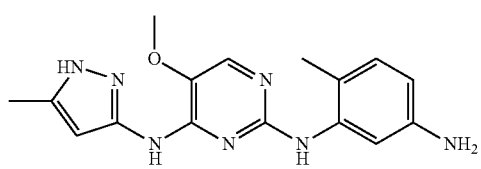
9d

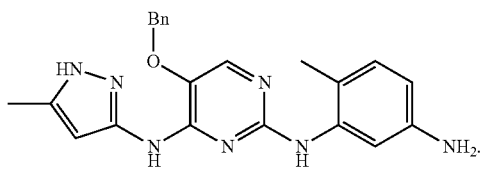
10g

15. A compound of formula VII having the following structure:

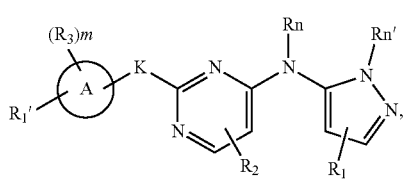
VII wherein,
K is NH, O, S, SO, SO$_2$, CH$_2$, C=O or absent;
R″ and R‴ are independently H or Boc;
R$_1$′ is nitro or protected amino;
A is aryl, heterocycloalkyl, cycloalkyl or heteroaryl;
m is an integer of 0 to 4;
R$_1$ is substituted or unsubstituted alkyl, substituted or unsubstituted heteroalkyl, substituted or unsubstituted cycloalkyl, substituted or unsubstituted heterocycloalkyl, substituted or unsubstituted aryl;

R$_2$ is amino, alkylamino, arylamino, heteroarylamino, thioalkyl, mercapto, halogen, alkoxy, alkanoyl, alkoxycarbonyl, C1-C6 alkyl, C2-C6 alkenyl, cycloalkyl, C2-C6 alkynyl, C5-C7 cycloalkenyl, C1-C6 trifluoroalkyl, cyano, wherein each of the substituents is independently of each other substituted by any of 0 to 3 groups selected from halogen, amino, hydroxy, mercapto, nitro or cyano;

R$_2$ is optionally H when R$_1$ is CH$_3$, R″ is Boc, R‴ is H, K is NH, A is phenyl, R$_3$ is CH$_3$, and m is 1;

R$_3$ is selected from the following substituents:

(i) aryloxy, amino, —NH-alkyl, —NH-aryl, —N-(aryl)$_2$, —CO$_2$H, —CO$_2$-alkyl, —CO$_2$-aryl, —CONH-alkyl, —CON-(alkyl)$_2$, —SO$_3$H, —CF$_3$, —CO—R$_9$ or —CO-aryl, wherein the groups of alkyl, aryl, aryl-substituted alkyl and heterocyclic group are each respectively further substituted by 0 to 3 groups which are preferably selected from halogen, NO$_2$, CN, OH, methoxy, NH$_2$, CO$_2$H, N—(R$_9$)(R$_{10}$), CONH$_2$, CHF$_2$ and CF$_3$;

(ii) hydrogen, halogen, —CN, —NO, —NO$_2$, —SO$_2$NHR$_9$, —CF$_2$H, —CH$_2$CN, —CH$_2$CH$_2$OH, —NHCOCH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein the groups of alkyl, aryl, alkyl-substituted aryl and heterocyclic group are optionally substituted by 0 to 3 groups which are independently selected from halogen, NO$_2$, CN, OH, methoxy, NH$_2$, CO$_2$H, N—(R$_9$)(R$_{10}$), R$_{25}$, CONH$_2$ and CF$_3$.

16. The compound according to claim 15, wherein the compound is selected from the following compounds:

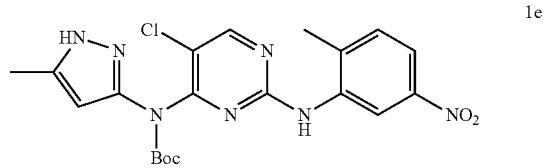
1e

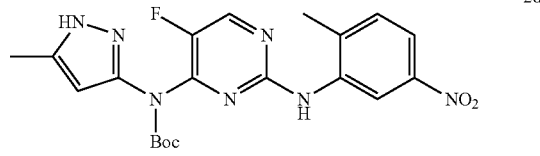
2d

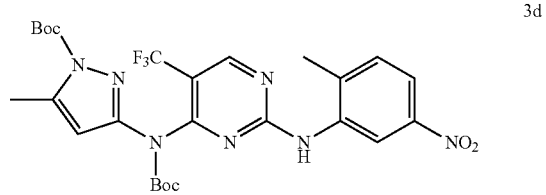
3d

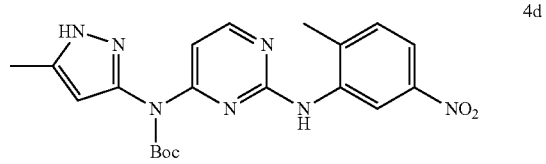
4d

-continued

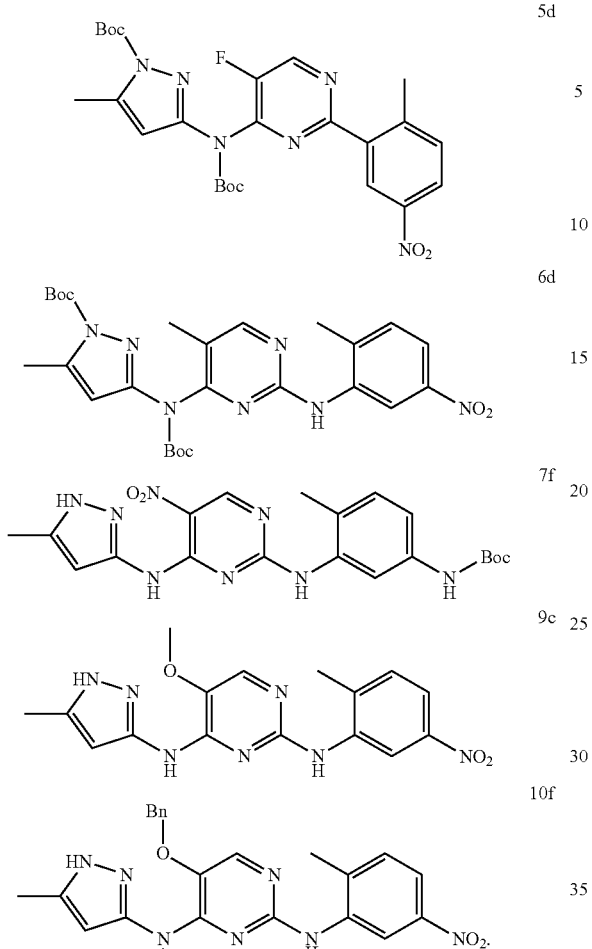

17. A compound of formula V having the following structure:

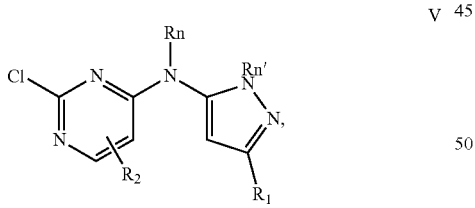

R" and R"' are independently H or Boc;
R₁ is substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
R₂ is amino, alkylamino, arylamino, heteroarylamino, thioalkyl, mercapto, alkanoyl, alkoxycarbonyl, C1-C6 alkyl, C2-C6 alkenyl, cycloalkyl, C2-C6 alkynyl, C5-C7 cycloalkenyl, C1-C6 trifluoroalkyl, cyano, wherein each of the substituents is independently of each other substituted by any of 0 to 3 groups selected from halogen, amino, hydroxy, mercapto, nitro or cyano.

18. The compound according to claim 17, wherein the compound is selected from the following compounds:

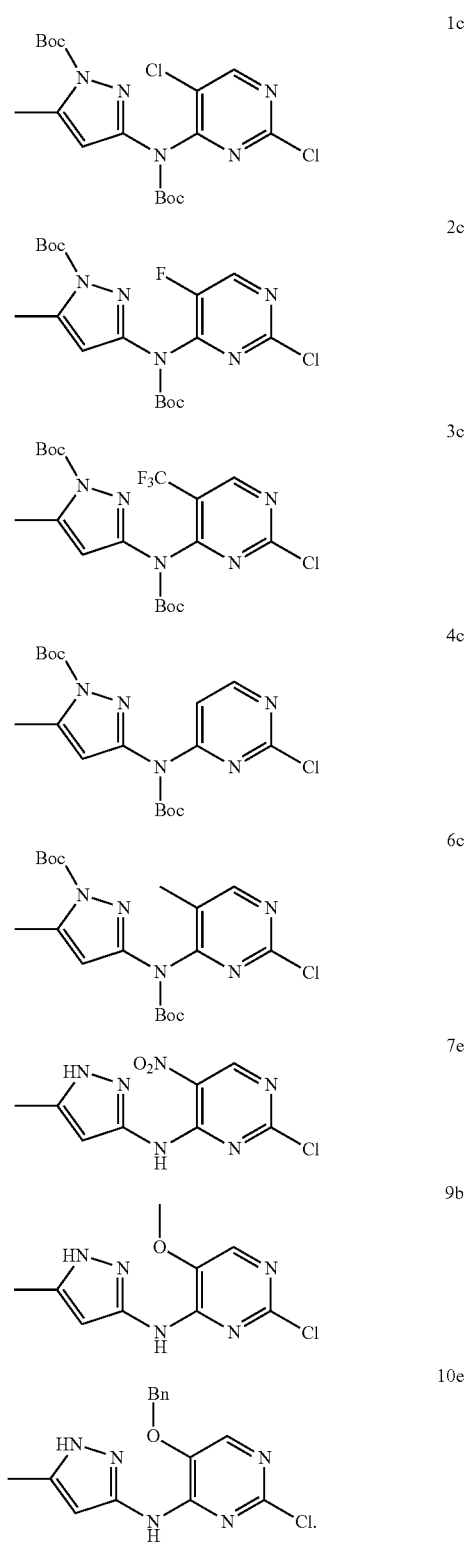

19. The compound of claim 8 wherein R₁ is selected from C1-C5 alkyl unsubstituted or substituted by R₃₂, 2-5 membered heteroalkyl unsubstituted or substituted by R₃₂, C3-C6 cycloalkyl unsubstituted or substituted by $R_{32}$ and 5- or 6-membered heterocycloalkyl unsubstituted or substituted by $R_{32}$.

20. The compound of claim 8 wherein $R_1$ is selected from unsubstituted C1-C5 alkyl, unsubstituted C3-C6 cycloalkyl and 5- or 6-membered heterocycloalkyl unsubstituted or substituted by $R_{32}$.

21. The compound of claim 8 wherein $R_1$ is selected from unsubstituted C1-C5 alkyl, unsubstituted thienyl and C1-C4 substituted thienyl.

22. The compound of claim 8 wherein $R_1$ is methyl.

23. The compound of claim 16 wherein $R_3$ is selected from C1-C10 alkyl and C2-C10 substituted or unsubstituted heteroalkyl.

24. The compound of claim 16 wherein $R_3$ is selected from methyl, ethyl, propyl and n-butyl.

25. The compound of claim 16 wherein $R_3$ is methyl.

26. The compound of claim 20 wherein $R_4$ is phenyl substituted by 0 to 3 groups which are selected from halogen and $CF_3$.

27. The compound of claim 20 wherein $R_4$ is 3-fluoromethyl-4-chlorophenyl.

28. The pharmaceutical composition of claim 24 wherein the oral-dosed preparation is selected from capsules, tablets, suppositories, suspensions, syrups, aqueous suspensions and solutions.

* * * * *